(12) United States Patent
Lang et al.

(10) Patent No.: US 7,995,822 B2
(45) Date of Patent: Aug. 9, 2011

(54) METHODS FOR THE COMPENSATION OF IMAGING TECHNIQUE IN THE PROCESSING OF RADIOGRAPHIC IMAGES

(75) Inventors: Philipp Lang, Lexington, MA (US); Daniel Steines, Lexington, MA (US); Siau-Way Liew, Pinole, CA (US); Rene Vargas-Voracek, Sunnyvale, CA (US)

(73) Assignee: ImaTx, Inc., Burlington, MA (US)

( * ) Notice: Subject to any disclaimer, the term of this patent is extended or adjusted under 35 U.S.C. 154(b) by 0 days.

(21) Appl. No.: 12/650,846

(22) Filed: Dec. 31, 2009

(65) Prior Publication Data
US 2010/0130832 A1    May 27, 2010

Related U.S. Application Data

(63) Continuation of application No. 10/809,578, filed on Mar. 25, 2004, now Pat. No. 7,664,298.

(60) Provisional application No. 60/457,599, filed on Mar. 25, 2003, provisional application No. 60/478,454, filed on Jun. 13, 2003.

(51) Int. Cl.
G06K 9/00    (2006.01)

(52) U.S. Cl. ........................ 382/128; 382/131; 382/132

(58) Field of Classification Search .................. 382/128, 382/131, 132; 600/442
See application file for complete search history.

(56) References Cited

U.S. PATENT DOCUMENTS

| | | | |
|---|---|---|---|
| 2,274,808 A | 3/1942 | Rinn | 250/69 |
| 3,924,133 A | 12/1975 | Reiss | 250/408 |
| 4,012,638 A | 3/1977 | Altschuler et al. | 250/491 |
| 4,126,789 A | 11/1978 | Vogl et al. | 250/505 |
| 4,233,507 A | 11/1980 | Volz | 250/252 |
| 4,251,732 A | 2/1981 | Fried | 250/479 |
| 4,298,800 A | 11/1981 | Goldman | 250/445 T |
| 4,356,400 A | 10/1982 | Polizzi et al. | 378/138 |
| 4,400,827 A | 8/1983 | Spears | 378/207 |
| 4,593,400 A | 6/1986 | Mouyen | 378/99 |
| 4,649,561 A | 3/1987 | Arnold | 378/207 |
| 4,686,695 A | 8/1987 | Macovski | 378/146 |
| 4,721,112 A | 1/1988 | Hirano et al. | 128/659 |
| 4,782,502 A | 11/1988 | Schulz | 378/18 |
| 4,922,915 A | 5/1990 | Arnold et al. | 128/653 R |
| 4,956,859 A | 9/1990 | Lanza et al. | 378/157 |
| 4,985,906 A | 1/1991 | Arnold | 378/18 |
| 5,001,738 A | 3/1991 | Brooks | 378/170 |

(Continued)

FOREIGN PATENT DOCUMENTS

CA    2342344    3/2000

(Continued)

OTHER PUBLICATIONS

Barker, "Case Method: Entity Relationship Modeling" (Computer Aided Systems Engineering), 1st Ed., Addison-Wesley Longman Pub. Co., Inc., publisher, 2 pages (Abstract Pages Only) (1990).

(Continued)

*Primary Examiner* — Tom Y Lu
(74) *Attorney, Agent, or Firm* — Sunstein Kann Murphy & Timbers LLP

(57) ABSTRACT

The present invention relates to methods and devices for analyzing x-ray images. In particular, devices, methods and algorithms are provided that allow for the accurate and reliable evaluation of bone structure and macro-anatomical parameters from x-ray images.

18 Claims, 17 Drawing Sheets

U.S. PATENT DOCUMENTS

| | | | |
|---|---|---|---|
| 5,090,040 A | 2/1992 | Lanza et al. | 378/62 |
| 5,122,664 A | 6/1992 | Ito et al. | 250/327.2 |
| 5,127,032 A | 6/1992 | Lam et al. | 378/189 |
| 5,150,394 A | 9/1992 | Karellas | 378/62 |
| 5,172,695 A | 12/1992 | Cann et al. | 128/653.1 |
| 5,187,731 A | 2/1993 | Shimura | 378/207 |
| 5,200,993 A | 4/1993 | Wheeler et al. | 379/96 |
| 5,222,021 A | 6/1993 | Feldman et al. | 364/413.14 |
| 5,228,445 A | 7/1993 | Pak et al. | 128/660.01 |
| 5,235,628 A | 8/1993 | Kalender | 378/207 |
| 5,247,934 A | 9/1993 | Wehrli et al. | 128/653.2 |
| 5,270,651 A | 12/1993 | Wehrli | 324/308 |
| 5,271,401 A | 12/1993 | Fishman | 128/654 |
| 5,320,102 A | 6/1994 | Paul et al. | 128/653.2 |
| 5,335,260 A | 8/1994 | Arnold | 378/207 |
| 5,384,643 A | 1/1995 | Inga et al. | 358/403 |
| 5,476,865 A | 12/1995 | Panetta et al. | 514/369 |
| 5,493,593 A | 2/1996 | Müller et al. | 378/19 |
| 5,493,601 A | 2/1996 | Fivez et al. | 378/207 |
| 5,513,240 A | 4/1996 | Hausmann et al. | 378/170 |
| 5,521,955 A | 5/1996 | Gohno et al. | 378/18 |
| 5,537,483 A | 7/1996 | Stapleton et al. | 382/309 |
| 5,562,448 A | 10/1996 | Mushabac | 433/215 |
| 5,565,678 A | 10/1996 | Manian | 250/252.1 |
| 5,592,943 A | 1/1997 | Buhler et al. | 128/661.03 |
| 5,600,574 A | 2/1997 | Reitan | 364/552 |
| 5,657,369 A | 8/1997 | Stein et al. | 378/208 |
| 5,673,298 A | 9/1997 | Mazess | 378/54 |
| 5,687,210 A | 11/1997 | Maitrejean et al. | 378/57 |
| 5,769,072 A | 6/1998 | Olsson et al. | 128/205.13 |
| 5,769,074 A | 6/1998 | Barnhill et al. | 128/630 |
| 5,772,592 A | 6/1998 | Cheng et al. | 600/407 |
| 5,852,647 A | 12/1998 | Schick et al. | 378/53 |
| 5,864,146 A | 1/1999 | Karellas | 250/581 |
| 5,886,353 A | 3/1999 | Spivey et al. | 250/370.09 |
| 5,915,036 A | 6/1999 | Grunkin et al. | 382/132 |
| 5,917,877 A | 6/1999 | Chiabrera et al. | 378/5.3 |
| 5,931,780 A | 8/1999 | Giger et al. | 600/407 |
| 5,945,412 A | 8/1999 | Fuh et al. | 514/176 |
| 5,948,692 A | 9/1999 | Miyauti et al. | 436/501 |
| 6,029,078 A | 2/2000 | Weinstein et al. | 600/407 |
| 6,064,716 A | 5/2000 | Siffert et al. | 378/53 |
| 6,077,224 A | 6/2000 | Lang et al. | 600/437 |
| 6,108,635 A | 8/2000 | Herren et al. | 705/2 |
| 6,156,799 A | 12/2000 | Hartke et al. | 514/573 |
| 6,178,225 B1 | 1/2001 | Zur et al. | 378/98.2 |
| 6,205,348 B1 | 3/2001 | Giger et al. | 600/407 |
| 6,215,846 B1 | 4/2001 | Mazess et al. | 378/62 |
| 6,226,393 B1 | 5/2001 | Grunkin et al. | 382/128 |
| 6,246,745 B1 | 6/2001 | Bi et al. | 378/54 |
| 6,248,063 B1 | 6/2001 | Barnhill et al. | 600/300 |
| 6,249,692 B1 | 6/2001 | Cowin | 600/407 |
| 6,252,928 B1 | 6/2001 | MacKenzie | 378/54 |
| 6,285,901 B1 | 9/2001 | Taicher et al. | 600/410 |
| 6,289,115 B1 | 9/2001 | Takeo | 382/130 |
| 6,302,582 B1 | 10/2001 | Nord et al. | 378/207 |
| 6,306,822 B1 | 10/2001 | Kumagai et al. | 514/7 |
| 6,315,553 B1 | 11/2001 | Sachdeva et al. | 433/24 |
| 6,320,931 B1 | 11/2001 | Arnold | 378/62 |
| 6,377,653 B1 | 4/2002 | Lee et al. | 378/54 |
| 6,411,729 B1 | 6/2002 | Grunkin | 382/132 |
| 6,430,427 B1 | 8/2002 | Lee et al. | 600/407 |
| 6,442,287 B1 | 8/2002 | Jiang et al. | 382/132 |
| 6,449,502 B1 | 9/2002 | Ohkubo | 600/407 |
| 6,463,344 B1 | 10/2002 | Pavloskaia et al. | 700/98 |
| 6,501,827 B1 | 12/2002 | Takasawa | 378/116 |
| 6,556,698 B1 | 4/2003 | Diano et al. | 382/132 |
| 6,690,761 B2 | 2/2004 | Lang et al. | 378/56 |
| 6,694,047 B1 | 2/2004 | Farrokhnia et al. | 382/132 |
| 6,717,174 B2 | 4/2004 | Karellas | 250/582 |
| 6,799,066 B2 | 9/2004 | Steines et al. | 600/407 |
| 6,807,249 B2 | 10/2004 | Dinten et al. | 378/54 |
| 6,811,310 B2 | 11/2004 | Lang et al. | 378/169 |
| 6,824,309 B2 | 11/2004 | Robert-Coutant et al. | 378/207 |
| 6,829,378 B2 | 12/2004 | DiFilippo et al. | 382/128 |
| 6,835,377 B2 | 12/2004 | Goldberg et al. | 424/93.7 |
| 6,836,557 B2 | 12/2004 | Tamez-Pena et al. | 382/128 |
| 6,895,077 B2 | 5/2005 | Karellas et al. | 378/98.3 |
| 6,904,123 B2 | 6/2005 | Lang | 378/54 |
| 6,934,590 B2 | 8/2005 | Ogawa | 700/19 |
| 6,975,894 B2 | 12/2005 | Wehrli et al. | 600/407 |
| 7,050,534 B2 | 5/2006 | Lang | 378/54 |
| 7,058,159 B2 | 6/2006 | Lang et al. | 378/54 |
| 7,120,225 B2 | 10/2006 | Lang et al. | 378/54 |
| 7,184,814 B2 | 2/2007 | Lang et al. | 600/416 |
| 7,239,908 B1 | 7/2007 | Alexander et al. | 600/427 |
| 7,245,697 B2 | 7/2007 | Lang | 378/54 |
| 7,283,857 B1 | 10/2007 | Fallon et al. | 600/407 |
| 7,292,674 B2 | 11/2007 | Lang | 378/54 |
| 7,379,529 B2 | 5/2008 | Lang | 378/54 |
| 7,467,892 B2 | 12/2008 | Lang et al. | 378/207 |
| 7,545,964 B2 | 6/2009 | Lang et al. | 382/128 |
| 7,580,504 B2 | 8/2009 | Lang et al. | 378/56 |
| 7,660,453 B2 | 2/2010 | Lang | 382/132 |
| 7,664,298 B2 | 2/2010 | Lang et al. | 382/128 |
| 7,676,023 B2 | 3/2010 | Lang | 378/54 |
| 7,840,247 B2 | 11/2010 | Liew et al. | 600/407 |
| 2002/0087274 A1 | 7/2002 | Alexander et al. | 702/19 |
| 2002/0159567 A1 | 10/2002 | Sako et al. | 378/117 |
| 2002/0186818 A1 | 12/2002 | Arnaud et al. | 378/165 |
| 2002/0194019 A1 | 12/2002 | Evertsz | 705/2 |
| 2002/0196966 A1 | 12/2002 | Jiang et al. | 382/132 |
| 2003/0015208 A1 | 1/2003 | Lang et al. | 128/922 |
| 2003/0198316 A1 | 10/2003 | Dewaele et al. | 378/54 |
| 2004/0106868 A1* | 6/2004 | Liew et al. | 600/442 |
| 2004/0247074 A1 | 12/2004 | Langton | 378/54 |
| 2005/0015002 A1 | 1/2005 | Dixon et al. | 600/407 |
| 2005/0148860 A1 | 7/2005 | Liew et al. | 600/410 |
| 2005/0240096 A1 | 10/2005 | Ackerman et al. | 600/410 |
| 2006/0062442 A1 | 3/2006 | Arnaud et al. | 382/128 |
| 2007/0047794 A1 | 3/2007 | Lang et al. | 382/132 |
| 2007/0274442 A1 | 11/2007 | Gregory et al. | 378/54 |
| 2008/0031412 A1 | 2/2008 | Lang et al. | 378/54 |
| 2008/0058613 A1 | 3/2008 | Lang et al. | 600/300 |
| 2008/0097794 A1 | 4/2008 | Arnaud et al. | 705/3 |
| 2008/0219412 A1 | 9/2008 | Lang | 378/207 |
| 2009/0207970 A1 | 8/2009 | Lang | 378/38 |
| 2009/0225958 A1 | 9/2009 | Lang | 378/207 |
| 2010/0014636 A1 | 1/2010 | Lang et al. | 378/56 |
| 2010/0098212 A1 | 4/2010 | Lang | 378/54 |
| 2010/0130832 A1 | 5/2010 | Lang et al. | 600/300 |
| 2010/0197639 A1 | 8/2010 | Lang et al. | 514/143 |

FOREIGN PATENT DOCUMENTS

| | | |
|---|---|---|
| DE | 19853965 | 5/2000 |
| EP | 0314506 | 5/1989 |
| EP | 0797952 | 10/1997 |
| EP | 0570936 | 8/2000 |
| EP | 0678191 | 2/2001 |
| EP | 1230896 | 8/2002 |
| EP | 1283492 | 2/2003 |
| EP | 1349098 | 10/2003 |
| EP | 1357480 | 10/2003 |
| EP | 1424650 | 6/2004 |
| EP | 1598778 | 11/2005 |
| EP | 1069395 | 7/2006 |
| GB | 2023920 | 1/1980 |
| JP | 62 266053 | 11/1987 |
| JP | 05 099829 | 4/1993 |
| JP | 08 186762 | 7/1996 |
| JP | 10 145396 | 5/1998 |
| JP | 10 262959 | 10/1998 |
| JP | 11 069136 | 3/1999 |
| JP | 11 112877 | 4/1999 |
| JP | 2002 045722 | 2/2000 |
| JP | 2000 126168 | 5/2000 |
| JP | 2000 139889 | 5/2000 |
| JP | 2003 230557 | 8/2003 |
| WO | WO 94/12855 | 6/1994 |
| WO | WO 95/14431 | 6/1995 |
| WO | WO 99/08597 | 2/1999 |
| WO | WO 99/45371 | 9/1999 |
| WO | WO 99/45845 | 9/1999 |
| WO | WO 99/52331 | 10/1999 |
| WO | WO 00/33157 | 6/2000 |
| WO | WO 00/72216 | 11/2000 |
| WO | WO 01/38824 | 5/2001 |

| WO | WO 01/63488 | 8/2001 |
| --- | --- | --- |
| WO | WO 01/65449 | 9/2001 |
| WO | WO 02/17789 | 3/2002 |
| WO | WO 02/22014 | 3/2002 |
| WO | WO 02/30283 | 4/2002 |
| WO | WO 02/096284 | 12/2002 |
| WO | WO 03/071934 | 9/2003 |
| WO | WO 03/073232 | 9/2003 |
| WO | WO 03/088085 | 10/2003 |
| WO | WO 2004/019256 | 3/2004 |
| WO | WO 2004/025541 | 3/2004 |
| WO | WO 2004/062495 | 7/2004 |
| WO | WO 2004/086972 | 10/2004 |
| WO | WO 2004/096048 | 11/2004 |
| WO | WO 2005/027732 | 3/2005 |
| WO | WO 2006/033712 | 3/2006 |
| WO | WO 2006/034018 | 3/2006 |
| WO | WO 2008/034101 | 3/2008 |

OTHER PUBLICATIONS

Bauer et al., "Biochemical Markers of Bone Turnover and Prediction of Hip Bone Loss in Older Women: The Study of Osteoporotic Fractures," *Journal of Bone and Mineral Research*, vol. 14, pp. 1404-1410 (1999).

Beck et al., "Experimental Testing of a DEXA-Derived Curved Beam Model of the Proximal Femur," Journal of Orthopaedic Research, vol. 16, No. 3, pp. 394-398 (1998).

Black et al., "An Assessment Tool for Predicting Fracture Risk in Postmenopausal Women" *Osteoporosis International*, vol. 12, pp. 519-528 (2001).

Blake et al., "Active Contours; The Application of Techniques from Graphics, Vision, Control Theory and Statistics to Visual Tracking of Shapes in Motion," Title page and Table of Contents pages only, 6 pages (1999).

Bushberg et al., "The Essential Physics of Medical Imaging," Lipincott, Williams & Wilkins, Title page and Table of Contents pages only, 3 pages (1994).

Cann, "Quantitative CT for Determination of Bone Mineral Density: A Review," Radiology, vol. 166, No. 2, pp. 509-522 (1988).

Castleman, "Digital Image Processing," Prentice Hall, Title page and Table of Contents pages only, 9 pages (1996).

Cheal et al., "Role of Loads & Prosthesis Material Properties on the Mechanics of the Proximal Femur After Total Hip Arthroplasty," *J. Orthop. Res.*, vol. 10, No. 3, pp. 405-422 (1992).

Cootes et al., "Anatomical statistical models and their role in feature extraction," *The British Journal of Radiology*, Special Issue, 7 pages [S133-S139] (2004).

Cootes et al., "Statistical models of appearance for medical image analysis and computer vision," *Proc. SPIE Medical Imaging*, 14 pages, (2001).

Cootes, "An Introduction to Active Shape Models," *Image Processing and Analysis*, Ch. 7, pp. 1-26 (2000).

Cortet et al., "Bone Microarchitecture and Mechanical Resistance," *Joint Bone Spine*, vol. 68, pp. 297-305 (2001).

Crabtree et al., "Improving Risk Assessment: Hip Geometry, Bone Mineral Distribution and Bone Strength in Hip Fracture Cases and Controls. The EPOS Study," *Osteoporos Int*, vol. 13, pp. 48-54 (2002).

Crawley, "In Vivo Tissue Characterization Using Quantitative Computed Tomography: A Review," *Journal of Medical Engineering & Technology*, vol. 14, No. 6, pp. 233-242 (1990).

Cummings et al., "Bone Density at Various Sites for Prediction of Hip Fractures," *The Lancet*, vol. 341, pp. 72-75 (1993).

Davies et al., "A Minimum Description Length Approach to Statistical Shape Modeling," IEEE Transaction on Medical Imaging, vol. 21, No. 5, pp. 525-537 (2002).

Duryea et al., "New radiographic-based surrogate outcome measures for osteoarthritis of the knee," *Osteoarthritis and Cartilage*, vol. 11, pp. 102-110 (2003).

Duryea et al., "Trainable rule-based algorithm for the measurement of joint space width in digital radiographic images of the knee," *Medical Physics*, vol. 27, No. 3, pp. 580-591 (2000).

Eastell, "Treatment of Postmenopausal Osteoporosis," *New Engl. J. of Med.*, vol. 338, No. 11, pp. 736-746 (1988).

Engelman et al., "Impact of Geographic Barriers on the Utilization of Mammograms by Older Rural Women," *Journal of the American Geriatrics Society*, vol. 50, No. 1, pp. 62-68 (2002).

Faulkner, "Bone Densitometry: Choosing the Proper Skeletal Site to Measure," *J. Clin. Densitometry*, vol. 1, No. 3, pp. 279-285 (1998).

Fleute et al., "Incorporating a statistically based shape model into a system for computer-assisted anterior cruciate ligament surgery," *Medical Image Analysis*, vol. 3, No. 3, pp. 209-222 (1999).

Fleute et al., "Statistical model registration for a C-arm CT system," Computer Science Department, The Johns Hopkins University, pp. 1667-1670 (2002).

Fleute et al., "Nonrigid 3-D/2-D Registration of Images Using Statistical Models," pp. 138-147 (1999).

Geraets et al., "A New Method for Automatic Recognition of the Radiographic Trabecular Pattern," *J. Bone and Min. Res.*, Department of Oral Radiology, Academic Center for Dentistry Amsterdam (ACTA), vol. 3, No. 3, pp. 227-233 (1990).

Gilliland et al., "Patterns of Mammography Use Among Hispanic, American Indian, and Non-Hispanic White Women in New Mexico, 1994-1997," *American Journal of Epidemiology*, vol. 152, No. 5, pp. 432-437 (2000).

Gluer et al., Peripheral Measurement Techniques for the Assessment of Osteoporosis, *Semin. Nucl. Med.*, vol. 27, No. 3, pp. 229-247 (1997).

Gluer, "Quantitative Ultrasound Techniques for the Assessment of Osteoporosis: Expert Agreement on Current Status," *J. Bone Miner. Res.*, vol. 12, No. 8, pp. 1280-1288 (1997).

Grisso et al., "Risk Factors for Falls as a Cause of Hip Fracture in Women. The Northeast Hip Fracture Study Group," *N. Engl. J. Med.*, (Abstract Pages Only), 1 page, vol. 324, No. 19 (1991).

Gudmundsdottir et al., "Vertebral Bone Density in Icelandic Women Using Quantitative Computed Tomography Without an External Reference Phantom," *Osteoporosis Int.*, vol. 3, pp. 84-89 (1993).

Hayes et al., "Biomechanics of Cortical and Trabecular Bone: Implications for Assessment of Fracture Risk," *Basic Orthopaedic Biomechanics*, 2nd Ed., Ch. 3, pp. 69-111, Lippincott-Raven, publishers (1997).

Hayes et al., "Biomechanics of Fracture Risk Prediction of the Hip and Spine by Quantitative Computed Tomography," *Radiologic Clinics of North America*, vol. 29, No. 1, pp. 1-18 (1991).

Hayes et al., "Impact Near the Hip Dominates Fracture Risk in Elderly Nursing Home Residents Who Fall," *Calcif. Tissue Int.* (Abstract Page Only), 1 page, vol. 52, No. 3 (1993).

Hedström et al., "Biochemical Bone Markers and Bone Density in Hip Fracture Patients," *Acta Orthop. Scand.*, vol. 71, No. 4, pp. 409-413 (2000).

Horn, "Closed-form solution of absolute orientation using unit quaternions," *J. Opt. Soc. of Am. A*, vol. 4, No. 4, pp. 629-642 (1987).

Hosking et al., "Prevention of Bone Loss with Alendronate in Postmenopausal Women Under 60 Years of Age," *N. Engl. J. Med.*, vol. 338, No. 8, pp. 485-492 (1998).

Ikuta et al., "Quantitative Analysis Using the Star Volume Method Applied to Skeleton Patterns Extracted with a Morphological Filter," *Journal of Bone and Mineral Metabolism*, vol. 18, pp. 271-277 (2000).

Jacobs et al., "Long-term Bone Mass Evaluation of Mandible and Lumbar Spine in a Group of Women Receiving Hormone Replacement Therapy," *European Journal Oral Sciences*, vol. 104, pp. 10-16 (1996).

Jazieh et al., "Mammography Utilization Pattern Throughout the State of Arkansas: A Challenge for the Future," *Journal of Community Health*, vol. 26, No. 4, pp. 249-255 (2001).

Jeffcoat et al., "Post-menopausal bone loss and its relationship to oral bone loss", *Periodontology*, vol. 23, pp. 94-102 (2000).

Klose, "Teleradiology—A Model for Remote Consultation," *Electromedica*, vol. 66, No. 1, pp. 37-41 (1998).

Kumasaka et al., "Initial Investigation of Mathematical Morphology for the Digital Extraction of the Skeletal Characteristics of Trabecular Bone," *Dept. of Oral Surgery and Oral and Maxillofacial Radiology*, Kanagawa Dental College, Japan, pp. 161-168 (1996).

Lam et al., "X-Ray Diagnosis: A Physician's Approach," Title/Copyright pages and Index pages only, 4 pages, Springer-Verlag, publisher (ISBN 9813083247) (1998).

Lang et al., "Osteoporosis—Current Techniques and Recent Developments in Quantitative Bone Densitometry" *Radiologic Clinics of North America*, vol. 29, No. 1, pp. 49-76 (1991).

Marshall et al., "Meta-Analysis of How Well Measures of Bone Mineral Density Predict Occurrence of Osteoporotic Fractures," *Br. Med. J.*, vol. 312, pp. 1254-1259 (1996).

Metrabio Website, "QUS-2 Calcaneal Ultrasonometer," What's New: Ultrasound, Retrieved from the Internet—http://www.metrabio.com/html/_prods/L3-ultrasound-r.ht, 2 pages (2001).

Mourtada et al., "Curved Beam Model of the Proximal Femur for Estimating Stress Using Dual-Energy X-Ray Absorptiometry Derived Structural Geometry," *J. Ortho. Res.*, vol. 14, No. 3, pp. 483-492 (1996).

Njeh et al., "The Role of Ultrasound in the Assessment of Osteoporosis: A Review," *Osteoporosis Int.*, vol. 7, pp. 7-22 (1997).

Njeh et al., "Quantitative Ultrasound: Assessment of Osteoporosis and Bone Status," Title page and Table of Contents pages only, 4 pages (1999).

Ouyang et al., "Morphometric Texture Analysis of Spinal Trabecular Bone Structure Assessed Using Orthogonal Radiographic Projections," *Med. Phys.*, vol. 25, No. 10, pp. 2037-2045 (1998).

Patel et al., "Radiation Dose to the Patient and Operator from a Peripheral Dual X-Ray Absorptiometry System," *Journal of Clinical Densitometry*, vol. 2, No. 4, pp. 397-401 (1999).

Pharoah, "X-Ray Film, Intensifying Screens, and Grids," Ch. 4, Section 4: Imaging Principles and Techniques, Oral Radiology, 4th ed., pp. 68-76 (2000).

Pinilla et al., "Impact Direction from a Fall Influences the Failure Load of the Proximal Femur as Much as Age-Related Bone Loss," *Calcified Tissue International*, vol. 58, pp. 231-235 (1996).

Riggs et al., "Changes in Bone Mineral Density of the Proximal Femur and Spine with Aging: Differences Between the Postmenopausal and Senile Osteoporosis Syndromes," *J. Clin. Invest.*, vol. 70, pp. 716-723 (1982).

Russ, "The Image Processing Handbook," 3rd Edition, North Carolina State Univ., Chapter 7: Processing Binary Images, pp. 494-501 (1998).

Ruttiman et al., "Fractal Dimension from Radiographs of Peridontal Alveolar Bone: A Possible Diagnostic Indicator of Osteoporosis," *Oral Surg, Oral Med, Oral Pathol.*, vol. 74, No. 1, pp. 98-110 (1992).

Sandler et al., "An Analysis of the Effect of Lower Extremity Strength on Impact Severity During a Backward Fall," *Journal of Biomechanical Engineering*, vol. 123, pp. 590-598 (2001).

Shrout et al., "Comparison of Morphological Measurements Extracted from Digitized Dental Radiographs with Lumbar and Femoral Bone Mineral Density Measurements in Postmenopausal Women," *J. Periondontal*, vol. 71, No. 3, pp. 335-340 (2000).

Slone et al., "Body CT: A Practical Approach," Title page and Table of Contents pages only, 4 pages, McGraw-Hill, publisher (ISBN 007058219) (1999).

Southard et al., "Quantitative Features of Digitized Radiographic Bone Profiles," *Oral Surgery, Oral Medicine, and Oral Pathology*, vol. 73, No. 6, pp. 751-759 (1992).

Southard et al., "The Relationship Between the Density of the Alveolar Processes and that of Post-Cranial Bone," *J. Dent. Res.*, vol. 79, No. 4, pp. 964-969 (2000).

Stout et al., "X-Ray Structure Determination: A Practical Guide," 2nd Ed., Title page and Table of Contents pages only, 4 pages, John Wiley & Sons, publisher (ISBN 0471607118) (1989).

Svendsen et al., "Impact of Soft Tissue on In-Vivo Accuracy of Bone Mineral Measurements in the Spine, Hip, and Forearm: A Human Cadaver Study," *J. Bone Miner. Res.*, vol. 10, No. 6, pp. 868-873 (1995).

Tothill et al., "Errors due to Non-Uniform Distribution of Fat in Dual X-Ray Absorptiometry of the Lumbar Spine," *Br. J. Radiol.*, vol. 65, pp. 807-813 (1992).

Van den Kroonenberg et al., "Dynamic Models for Sideways Falls from Standing Height," *Journal of Biomechanical Engineering*, vol. 117, pp. 309-318 (1995).

Verhoeven et al. "Densitometric Measurement of the Mandible: Accuracy and Validity of Intraoral Versus Extraoral Radiographic Techniques in an In Vitro Study," *Clin. Oral Impl. Res.*, vol. 9, pp. 333-342 (1998).

White et al., "Alterations of the Trabecular Pattern in the Jaws of Patients with Osteoporosis," *Oral Surg., Oral Med., Oral Pathol., Oral Radiol., and Endod.*, vol. 88, pp. 628-635 (1999).

Yoshikawa et al., "Geometric Structure of the Femoral Neck Measured Using Dual-Energy X-Ray Absorptiometry," *J. Bone Miner. Res.*, vol. 10, No. 3, p. 510 (Abstract Only) (1995).

International Searching Authority, International Preliminary Report on Patentability—Application No. PCT/US2004/009165, dated Oct. 1, 2005 (9 pages).

International Searching Authority, International Search Report and Written Opinion of the International Searching Authority—Application No. PCT/US2004/009165, dated Feb. 10, 2005 (13 pages).

Bromberg & Sunstein LLP Boston, MA, Preliminary Amendment—U.S. Appl. No. 10/809,578, filed Nov. 3, 2006 (4 pages).

United States Patent and Trademark Office, Non-Final Office Action—U.S. Appl. No. 10/809,578, dated Apr. 23, 2008 (10 pages).

Bromberg & Sunstein LLP Boston, MA, Amendment to Non-Final Office Action, dated Apr. 23, 2008—U.S. Appl. No. 10/809,578, filed Oct. 23, 2008 (11 pages).

United States Patent and Trademark Office, Non-Final Office Action—U.S. Appl. No. 10/809,578, dated Jan. 23, 2009 (5 pages).

Sunstein Kann Murphy & Timbers LLP Boston, MA, Amendment to Non-Final Office Action, dated Jan. 23, 2009—U.S. Appl. No. 10/809,578, filed Jul. 23, 2009 (11 pages).

United States Patent and Trademark Office, Notice of Allowance and Fees Due—U.S. Appl. No. 10/809,578, dated Sep. 10, 2009 (6 pages).

Sunstein Kann Murphy & Timbers LLP Boston, MA, Request for Continued Examination—U.S. Appl. No. 10/809,578, filed Dec. 10, 2009 (3 pages).

United States Patent and Trademark Office, Notice of Allowance and Fees Due—U.S. Appl. No. 10/809,578, dated Dec. 18, 2009 (14 pages).

* cited by examiner

An example of a regular interval sampling field for microarchitecture (+) and a higher density sampling field for macro-anatomical features(*) on a femur radiograph.

Watershed segmentation boundaries superimposed on a parameter map. The two white lines are the actual fracture paths resulted from an in-vitro mechanical loading test.

Process to determine fracture risk using overlapping window processing and fracture paths prediction.

(a)

(b)

METHODS FOR THE COMPENSATION OF IMAGING TECHNIQUE IN THE PROCESSING OF RADIOGRAPHIC IMAGES

CROSS-REFERENCE TO RELATED APPLICATIONS

This application is a continuation of U.S. Ser. No. 10/809,578 filed on Mar. 25, 2004, which in turn claims the benefit of U.S. Provisional Application Nos. 60/457,599, filed Mar. 25, 2003, and 60/478,454, filed Jun. 13, 2003, and the disclosures of all of the foregoing applications are incorporated by reference herein in their entirety.

FIELD OF THE INVENTION

The present invention is in the field of imaging and analysis thereof. In particular, methods and compositions for accurately analyzing images to determine bone mineral density and/or bone structure are described.

BACKGROUND OF THE INVENTION

Osteoporosis is a condition that affects millions of Americans. Osteoporosis refers to a condition characterized by low bone mass and microarchitectural deterioration of bone tissue, with a consequent increase of bone fragility and susceptibility to fracture. Osteoporosis presents commonly with vertebral fractures or hip fractures due to the decrease in bone mineral density and deterioration of structural properties and microarchitecture of bone.

Imaging techniques are important diagnostic tools, particularly for bone related conditions. Currently available techniques for the noninvasive assessment of the skeleton for the diagnosis of osteoporosis or the evaluation of an increased risk of fracture include dual x-ray absorptiometry (DXA) (Eastell et al. (1998) *New Engl J. Med* 338:736-746); quantitative computed tomography (QCT) (Cann (1988) *Radiology* 166:509-522); peripheral DXA (pDXA) (Patel et al. (1999) *J Clin Densitom* 2:397-401); peripheral QCT (pQCT) (Gluer et. al. (1997) *Semin Nucl Med* 27:229-247); x-ray image absorptiometry (RA) (Gluer et. al. (1997) *Semin Nucl Med* 27:229-247); and quantitative ultrasound (QUS) (Njeh et al. "Quantitative Ultrasound: Assessment of Osteoporosis and Bone Status" 1999, Martin-Dunitz, London England; U.S. Pat. No. 6,077,224, incorporated herein by reference in its entirety). (See, also, WO 9945845; WO 99/08597; and U.S. Pat. No. 6,246,745).

DXA of the spine and hip has established itself as the most widely used method of measuring BMD. Tothill, P. and D. W. Pye, (1992) *Br J Radiol* 65:807-813. The fundamental principle behind DXA is the measurement of the transmission through the body of x-rays of 2 different photon energy levels. Because of the dependence of the attenuation coefficient on the atomic number and photon energy, measurement of the transmission factors at 2 energy levels enables the area densities (i.e., the mass per unit projected area) of 2 different types of tissue to be inferred. In DXA scans, these are taken to be bone mineral (hydroxyapatite) and soft tissue, respectively. However, it is widely recognized that the accuracy of DXA scans is limited by the variable composition of soft tissue. Because of its higher hydrogen content, the attenuation coefficient of fat is different from that of lean tissue. Differences in the soft tissue composition in the path of the x-ray beam through bone compared with the adjacent soft tissue reference area cause errors in the BMD measurements, according to the results of several studies. Tothill, P. and D. W. Pye, (1992) *Br J Radiol,* 65:807-813; Svendsen, O. L., et al., (1995) *J Bone Min Res* 10:868-873. Moreover, DXA systems are large and expensive, ranging in price between $75,000 and $150,000.

Quantitative computed tomography (QCT) is usually applied to measure the trabecular bone in the vertebral bodies. Cann (1988) *Radiology* 166:509-522. QCT studies are generally performed using a single kV setting (single-energy QCT), when the principal source of error is the variable composition of the bone marrow. However, a dual-kV scan (dual-energy QCT) is also possible. This reduces the accuracy errors but at the price of poorer precision and higher radiation dose. Like DXA, however, QCT are very expensive and the use of such equipment is currently limited to few research centers.

Quantitative ultrasound (QUS) is a technique for measuring the peripheral skeleton. Njeh et al. (1997) *Osteoporosis Int* 7:7-22; Njeh et al. Quantitative Ultrasound: Assessment of Osteoporosis and Bone Status. 1999, London, England: Martin Dunitz. There is a wide variety of equipment available, with most devices using the heel as the measurement site. A sonographic pulse passing through bone is strongly attenuated as the signal is scattered and absorbed by trabeculae. Attenuation increases linearly with frequency, and the slope of the relationship is referred to as broadband ultrasonic attenuation (BUA; units: dB/MHz). BUA is reduced in patients with osteoporosis because there are fewer trabeculae in the calcaneus to attenuate the signal. In addition to BUA, most QUS systems also measure the speed of sound (SOS) in the heel by dividing the distance between the sonographic transducers by the propagation time (units: m/s). SOS values are reduced in patients with osteoporosis because with the loss of mineralized bone, the elastic modulus of the bone is decreased. There remain, however, several limitations to QUS measurements. The success of QUS in predicting fracture risk in younger patients remains uncertain. Another difficulty with QUS measurements is that they are not readily encompassed within the WHO definitions of osteoporosis and osteopenia. Moreover, no intervention thresholds have been developed. Thus, measurements cannot be used for therapeutic decision-making.

There are also several technical limitations to QUS. Many devices use a foot support that positions the patient's heel between fixed transducers. Thus, the measurement site is not readily adapted to different sizes and shapes of the calcaneus, and the exact anatomic site of the measurement varies from patient to patient. It is generally agreed that the relatively poor precision of QUS measurements makes most devices unsuitable for monitoring patients' response to treatment. Gluer (1997) *J Bone Min Res* 12:1280-1288.

Radiographic absorptiometry (RA) is a technique that was developed many years ago for assessing bone density in the hand, but the technique has recently attracted renewed interest. Gluer et al. (1997) *Semin Nucl Med* 27:229-247. With this technique, BMD is measured in the phalanges. The principal disadvantage of RA of the hand is the relative lack of high turnover trabecular bone. For this reason, RA of the hand has limited sensitivity in detecting osteoporosis and is not very useful for monitoring therapy-induced changes.

Peripheral x-ray absorptiometry methods such as those described above are substantially cheaper than DXA and QCT with system prices ranging between $15,000 and $35,000. However, epidemiologic studies have shown that the discriminatory ability of peripheral BMD measurements to predict spine and hip fractures is lower than when spine and hip BMD measurements are used. Cummings et al. (1993) *Lancet* 341:72-75; Marshall et al. (1996) *Br Med J* 312:1254-

1259. The main reason for this is the lack of trabecular bone at the measurement sites used with these techniques. In addition, changes in forearm or hand BMD in response to hormone replacement therapy, bisphosphonates, and selective estrogen receptor modulators are relatively small, making such measurements less suitable than measurements of principally trabecular bone for monitoring response to treatment. Faulkner (1998) *J Clin Densitom* 1:279-285; Hoskings et al. (1998) *N Engl J Med* 338:485-492. Although attempts to obtain information on bone mineral density from dental x-rays have been attempted (See, e.g., Shrout et al. (2000) *J. Periodonol.* 71:335-340; Verhoeven et al. (1998) *Clin Oral Implants Res* 9(5):333-342), these have not provided accurate and reliable results.

Furthermore, current methods and devices do not generally take into account bone structure analyses. See, e.g., Ruttimann et al. (1992) *Oral Surg Oral Med Oral Pathol* 74:98-110; Southard & Southard (1992) *Oral Surg Oral Med Oral Pathol* 73:751-9; White & Rudolph, (1999) *Oral Surg Oral Med Oral Pathol Oral Radiol Endod* 88:628-35.

Thus, although a number of devices and methods exist for evaluating bone, there are a number of limitations on such devices and methods. Consequently, the inventors have recognized the need, among other things, to provide methods and compositions that result in the ability to obtain accurate bone mineral density and bone structure information from images (e.g., radiographic images) and data.

SUMMARY OF THE INVENTION

In one aspect, the disclosure provides a method to derive information regarding one or more bone parameters from an image, the method comprising the steps of: (a) obtaining an image comprising bone from a subject; (b) defining two or more regions of interest (ROIs) in the image; and (c) analyzing a plurality of positions in the ROIs to determine one or more parameters selected from the group consisting of bone microarchitecture, bone macro-anatomy, biomechanical parameters and combinations thereof of the ROIs. In certain embodiments, the ROIs are overlapping. The positions analyzed in the ROIs may be at regular intervals relative to one another or, alternatively, may be irregularly spaced relative to each other. Thus, in certain embodiments, the methods involve determining bone micro-architecture, for example by analyzing positions at regular intervals. In other embodiments, the methods involve determining bone macro-anatomy, for example by analyzing positions at irregular intervals in the image.

In any of the methods described herein, the image can be two-dimensional (2D) or three-dimensional (3D). The images may be x-rays, MRI images, CAT scan images, or any other image including bone. In any of the methods, the image may be an electronic image.

In any of the methods described herein, the subject can be, for example, an osteoporosis subject.

In another aspect, this disclosure relates to a method of generating a map of one or more bone parameters, the method comprising the steps of (a) obtaining information on bone parameters according to the method of any of methods described herein; and (b) identifying regions of the image that exhibit similar parameter characteristics, thereby creating a parameter map of the image.

In yet another aspect, a method of predicting a fracture path in a subject is provided, the method comprising the steps of: (a) generating multiple parameter maps according to any of the methods of generating parameters maps described herein; (b) generating a composite parameter map from the multiple parameters maps of step (a); and (c) analyzing the composite parameter map to identify possible fracture paths.

In yet another aspect, the invention includes a method of predicting a fracture path in a subject, the method comprising the steps of: (a) analyzing of one or more parameter maps preparing according to any of the methods described herein, wherein the analysis is watershed segmentation analysis or Markov random field analysis; and (c) identifying possible fracture paths based on the analysis of step (a), thereby predicting a fracture path in the subject.

In another aspect, the invention includes a method of predicting the risk of fracture in a subject, the method comprising the steps of: (a) generating a finite element model from one or more parameter maps obtained according any of the methods described herein; (b) applying simulated force vectors that would occur during a fracture incident to the finite element model generated in step(s); and (c) determining the minimum forces required for fracture to occur, thereby estimating the risk of fracture.

In a still further aspect, the invention includes a method of determining the risk of fracture in a subject comprising: (a) predicting a fracture path according to any of the methods of predicting fracture path as described herein; (b) evaluating one or more selected bone parameters along the predicted fracture path, thereby estimating the risk of fracture.

In another aspect, the invention includes a method of treating a subject with bone disease comprising (a) obtaining an image from a subject; (b) analyzing the image obtained in step (a) using any of the methods described herein; (c) diagnosing a bone disease based on the analysis of step (b); and (d) selecting and administering a suitable treatment to said subject based on said diagnosis.

DETAILED DESCRIPTION OF THE INVENTION

Figure 1:
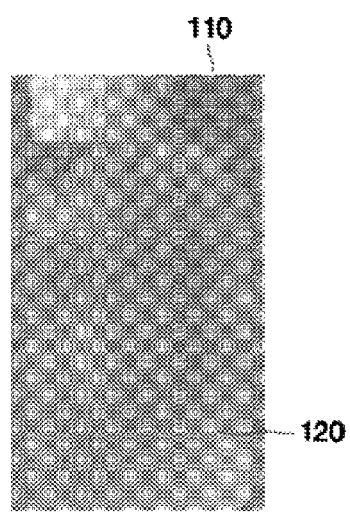
FIG. 1 shows an example of a dental x-ray. A calibration phantom 110 is seen. Regions of interest 120 have been placed for measurement of bone mineral density or structure.
Figure 2:
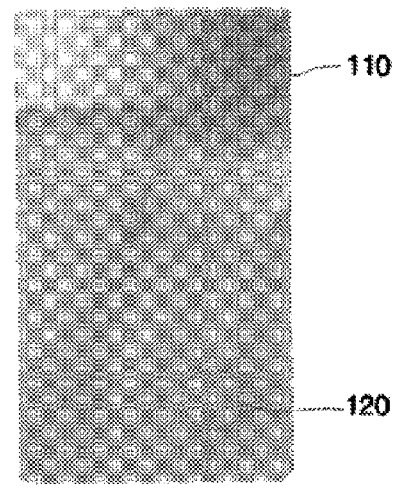
FIG. 2 shows another example of a dental x-ray. A calibration phantom 110 is seen. Regions of interest 120 have been placed for measurement of bone mineral density or structure.
Figure 3:
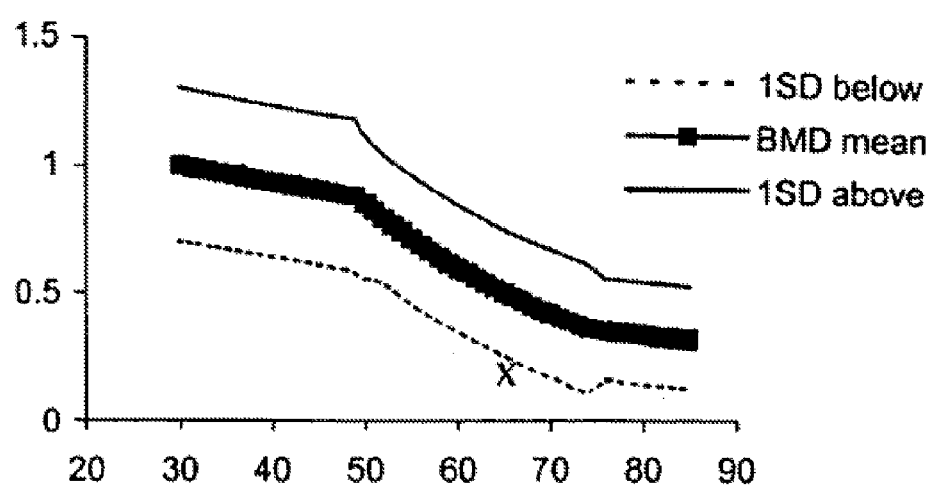
FIG. 3 shows an example of an analysis report resulting from a measurement of mandibular or maxillary bone mineral density. A subject (X) is more than one standard deviation below the mean of age-matched controls (x-axis age, y-axis arbitrary units BMD).

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention. Thus, the present invention is not intended to be limited to the embodiments shown, but is to be accorded the widest scope consistent with the principles and features disclosed and shown herein. To the extent necessary to achieve a complete understanding of the invention disclosed, the specification and drawings of all issued patents, patent publications, and patent applications cited in this application are incorporated herein by reference.

The practice of the present invention employs, unless otherwise indicated, conventional methods of imaging and image processing within the skill of the art. Such techniques are explained fully in the literature. See, e.g., WO 02/22014, incorporated herein in its entirety by reference; X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; The Essential Physics of Medical Imaging, editors Bushberg, Seibert, Leidholdt Jr & Boone, 2002, Lippincott, Williams & Wilkins; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher.

Methods and compositions useful in analyzing images are described. In particular, the invention includes methods of obtaining and/or deriving information about bone mineral density and/or bone structure from an image. Additionally, the present invention relates to the provision of accurate calibration phantoms for use in determining bone structure and methods of using these calibration phantoms. In particular, the present invention recognizes for the first time that errors arising from misplacement of interrogation sites in dental or hip x-rays of bone density and/or bone structure can be corrected by positioning the x-ray tube, the detector and/or the calibration reference with respect to an anatomical landmark (or anatomical region of interest).

Advantages of the present invention include, but are not limited to, (i) providing accessible and reliable means for analyzing x-rays; (ii) providing non-invasive measurements of bone structure and architecture and macro-anatomy; (iii) providing methods of diagnosing bone conditions (e.g., osteoporosis, fracture risk); (iv) providing methods of treating bone conditions; and (iv) providing these methods in cost-effective manner.

1.0. Obtaining Data from Images

An image can be acquired using well-known techniques from any local site. Non-limiting examples of imaging techniques suitable for acquiring images from which data can be obtained include, ultrasound, CAT scan, MRI and the like. See, also, "Primer of Diagnostic Imaging," 3rd edition, eds. Weissleder et al. (2002), Mosby Press; and International Publication WO 02/22014.

In certain aspects, 2D planar x-ray imaging techniques are used. 2D planar x-ray imaging is a method that generates an image by transmitting an x-ray beam through a body or structure or material and by measuring the x-ray attenuation on the other side of said body or said structure or said material. 2D planar x-ray imaging is distinguishable from cross-sectional imaging techniques such as computed tomography or magnetic resonance imaging. If the x-ray image was captured using conventional x-ray film, the x-ray can be digitized using any suitable scanning device. Digitized x-ray images can be transmitted over a networked system, e.g. the Internet, into a remote computer or server. It will be readily apparent that x-ray images can also be acquired using digital acquisition techniques, e.g. using photostimulable phosphor detector systems or selenium or silicon detector systems, the x-ray image information is already available in digital format which can be easily transmitted over a network. In other embodiments, 3D images are acquired, for example, using 3D imaging techniques and/or by creating 3D images from 2D images.

Any images can be used including, but not limited to, digital x-rays and conventional x-ray film (which can be digitized using commercially available flatbed scanners). In certain embodiments, the x-ray is of the hip region, for example performed using standard digital x-ray equipment (Kodak DirectView DR 9000, Kodak, Rochester, N.Y.). Patients are typically positioned on an x-ray table in supine position, parallel to the long axis of the table, with their arms alongside their body. The subject's feet may be placed in neutral position with the toes pointing up or in internal rotation or may be placed in a foot holder such that the foot in a neutral position (0° rotation) or in any desired angle of rotation (e.g., internal or external) relative to neutral (see, also Example 8 below). Foot holders suitable for such purposes may include, for example, a base plate extending from the foot, for example, from the mid to distal thigh to the heel. The base plate preferably sits on the x-ray table. The patients' foot is positioned so that the posterior aspect of the heel is located on top of the base plate. The medial aspect of the foot is placed against a medial guide connected rigidly to the base plate at a 90° angle by any suitable means (e.g., straps, velcro, plastic, tape, etc.). A second, lateral guide attached to the base plate at a 90° angle with a sliding mechanism can then be moved toward the lateral aspect of the foot and be locked in position, for example when it touches the lateral aspect of the foot. The use of a foot holder can help improve the reproducibility of measurements of bone structure parameters or macro-anatomical and/or biomechanical parameters.

As will be appreciated by those of skill in the art, the patient or subject can be any warm-blooded animal. Typically patients, or subjects, are chosen from the class Mammalia. Thus, for example, patients, or subjects, would include humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. To the extent desirable, other non-mammals can be subjected to the protocols described herein without departing from the scope of the invention.

Persons of skill in the art will appreciate that macro-anatomical parameters generally describe the shape, size or thickness of bone and/or surrounding structure. Oftentimes the typical parameters are, but need not be, greater than 0.5 mm in size in at least one dimension. Generally, in the hip joint, macro-anatomical parameters include thickness of the femoral shaft cortex, thickness of the femoral neck cortex, cortical width, hip axis length, CCD (caput-collum-diaphysis) angle, neck-shaft angle and width of the trochanteric region. In the spine, macro-anatomical parameters include thickness of the superior and inferior endplate, thickness of the anterior, lateral and posterior vertebral walls, diameter and height of the vertebral body, dimensions of the spinal canal and the posterior elements.

Generally, the ray is centered onto the hip joint medial and superior to the greater trochanter. A calibration phantom, such as an aluminum step wedge may also be included in the images to calibrate gray values before further image analysis.

In other embodiments, dental x-rays are preferred because of the relative ease and lack of expense in obtaining these images. Further, the mandible and maxilla are primarily composed of trabecular bone. Since the metabolic turnover of trabecular bone is approximately eight times greater than that of cortical bone, areas of predominantly trabecular bone such as the vertebral body are preferred sites for measuring bone mineral density. Lang et al. (1991) *Radiol Clin North Am* 29:49-76. Thus, trabecular bone is clearly visible on the dental x-ray image, thus facilitating quantitative analysis of bone mineral density and structure. Jeffcoat et al. (2000) *Periodontol* 23:94-102; Southard et al. (2000) *J Dent Res* 79:964-969. Further, the earliest bone loss in osteoporosis patients occurs in areas of trabecular bone. Multiple dental x-ray images are commonly made in most Americans throughout life. Indeed, there are approximately 750 million U.S. dental visits annually and 150 million of these patients result in more than 1 billion dental x-rays taken each year. Thus, the ability to diagnose osteoporosis on dental x-rays would be extremely valuable since it would create the opportunity for low-cost mass screening of the population.

Preferably, x-ray imaging is performed using standard x-ray equipment, for instance standard dental x-ray equipment (e.g. General Electric Medical Systems, Milwaukee, Wis.). X-rays of the incisor region and canine region are acquired using a standard x-ray imaging technique with 80 kVp and automatic exposure using a phototimer or using a manual technique with 10 mA tube current. X-ray images are acquired, for example, on Kodak Ultraspeed film (Kodak, Rochester, N.Y.). X-ray images may be digitized using a commercial flatbed scanner with transparency option (Acer ScanPremio ST). Similarly, other imaging techniques are typically performed using standard equipment, for instance, MRI or CAT equipment.

1.1. Calibration Phantoms

It is highly preferred that the images include accurate reference markers, for example calibration phantoms for assessing bone mineral density and/or bone structure and/or one or more macro-anatomical and/or biomechanical parameters on any given image. Calibration references (also known as calibration phantoms) for use in imaging technologies have been described. See, e.g., U.S. Pat. No. 5,493,601 and U.S. Pat. No. 5,235,628. U.S. Pat. No. 5,335,260 discloses a calibration phantom representative of human tissue containing variable concentrations of calcium that serves as reference for quantifying calcium, bone mass and bone mineral density in x-ray and CT imaging systems. However, currently available calibration phantoms are not always accurate. Because bone mineral density accounts for considerably less than 100% of fracture risk in osteoporosis (Ouyang et al. (1997) *Calif Tissue Int*, 60:139-147) some of the methods and devices described herein are designed to assess not only bone mineral density but also bone structure and, in addition, macro-anatomical and/or biomechanical parameters. By assessing two or more of these parameters, more accurate testing and screening can be provided for conditions such as osteoporosis.

Thus, in certain aspects, the current invention provides for methods and devices that allow accurate quantitative assessment of information contained in an x-ray such as density of an anatomic structure and/or morphology of an anatomic structure. Any suitable calibration phantom can be used, for example, one that comprises aluminum or other radio-opaque materials. U.S. Pat. No. 5,335,260 describes other calibration phantoms suitable for use in assessing bone mineral density in images. Examples of other suitable calibration reference materials can be fluid or fluid-like materials, for example, one or more chambers filled with varying concentrations of calcium chloride or the like.

Numerous calibration phantoms (or reference calibrations) can be used in the practice of the present invention. Typically, the system used to monitor bone mineral density and/or bone structure and/or one or more macro-anatomical and/or biomechanical parameters in a target organism comprises an image (e.g., a dental or hip radiograph), which provides information on the subject; an assembly including a calibration phantom, which acts as a reference for the data in the image; and at least one data processing system, which evaluates and processes the data from the image and/or from the calibration phantom assembly.

Figure 4:
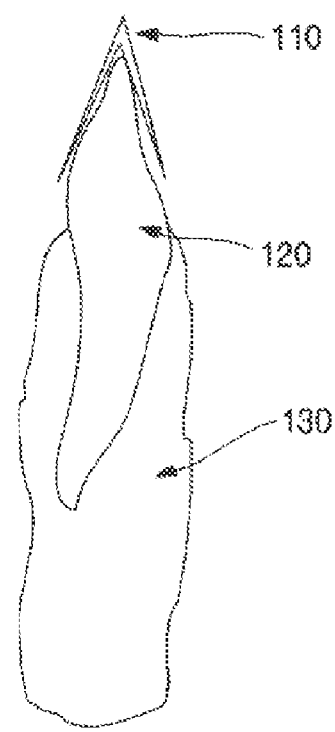
FIG. 4 shows an example of a V-shaped calibration phantom 110 mounted on a tooth 120. Gums are also shown 130.

It will be readily apparent that a calibration phantom can contain a single, known density or structure reference. Furthermore, a gradient in density can be achieved by varying the thickness or the geometry of the calibration phantom along the path of the x-ray beam, for example, by using a V-shape of the calibration phantom of varying thickness (FIG. 4). The calibration phantom can also include angles. For example, the calibration phantom can be "T"-shaped or "L"-shaped thereby including one or more 90 degree angles.

The calibration phantom can contain several different areas of different radio-opacity. For example, the calibration phantom can have a step-like design, whereby changes in local thickness of the wedge result in differences in radio-opacity. Stepwedges using material of varying thickness are frequently used in radiology for quality control testing of x-ray beam properties. By varying the thickness of the steps, the intensity and spectral content of the x-ray beam in the projection image can be varied. Stepwedges are commonly made of aluminum, copper and other convenient and homogeneous materials of known x-ray attenuation properties. Stepwedge-like phantoms can also contain calcium phosphate powder or calcium phosphate powder in molten paraffin.

Alternatively, continuous wedges may be used or the calibration reference may be designed such that the change in radio-opacity is from periphery to center (for example in a round, ellipsoid, rectangular, triangular of other shaped structure). As noted above, the calibration reference can also be constructed as plurality of separate chambers, for example fluid filled chambers, each including a specific concentration of a reference fluid (e.g., calcium chloride). In addition to one or more fluids, a calibration phantom can also contain metal powder, e.g. aluminum or steel powder, embedded within it (for example, embedded in a plastic).

In certain embodiments, the calibration phantom is specifically designed to serve as a reference for bone structure (e.g., trabecular spacing, thickness and the like). For example, the calibration wedge can contain one or more geometric patterns with known dimensions, e.g. a grid whereby the spacing of a grid, thickness of individual grid elements, etc. are known. This known geometric pattern of radio-opaque elements in the calibration phantom can be used to improve the accuracy of measurements of trabecular bone structure in an x-ray. Such measurements of trabecular bone structure can include, but are not limited to, trabecular spacing, trabecular length and trabecular thickness. Such measurements of trabecular spacing, trabecular length and trabecular thickness can, for example, be performed in a dental or spine or hip x-ray. These calibration phantoms can be made up of a variety of materials include, plastics, metals and combinations thereof. Further, the reference components can be solid, powdered, fluid or combinations thereof. Thus, the calibration wedge can also be used to improve measurements of bone structure.

In certain embodiments, the calibration phantom is specifically designed to serve as a reference for macro-anatomical parameters (e.g., in the hip joint, thickness of the femoral shaft cortex, thickness of the femoral neck cortex, cortical width, hip axis length, CCD (caput-collum-diaphysis) angle, neck-shaft angle and width of the trochanteric region; and in the spine, thickness of the superior and inferior endplate, thickness of the anterior, lateral and posterior vertebral walls, diameter and height of the vertebral body, dimensions of the spinal canal and the posterior elements). For example, the calibration wedge can contain one or more geometric patterns with known dimensions, e.g. a grid whereby the spacing of a grid, thickness of individual grid elements, etc. are known. This known geometric pattern of radio-opaque elements in the calibration phantom can be used to improve the accuracy of measurements of macro-anatomical and/or biomechanical parameters in an x-ray, for example by aiding in the correction of image magnification. Such measurements of macro-anatomical parameters can, for example, be performed in a dental or spine or hip x-ray. These calibration phantoms can be made up of a variety of materials include, plastics, metals and combinations thereof. Further, the reference components can be solid, powdered, fluid or combinations thereof. Thus, the calibration wedge can also be used to improve measurements of bone structure.

Since the present invention contemplates analysis of dental x-ray images for information on bone structure, bone mineral density or both structure and density, it will be apparent that calibration phantoms will be selected based on whether structure, density or both are being measured. Thus, one or more calibration phantoms may be present.

Whatever the overall shape or composition of the calibration phantom, when present, the at least one marker be positioned at a known density and/or structure in the phantom. Furthermore, it is preferred that at least one geometric shape or pattern is included in the calibration phantom. Any shape can be used including, but not limited to, squares, circles, ovals, rectangles, stars, crescents, multiple-sided objects (e.g., octagons), V- or U-shaped, inverted V- or U-shaped, irregular shapes or the like, so long as their position is known to correlate with a particular density of the calibration phantom. In preferred embodiments, the calibration phantoms described herein are used in 2D planar x-ray imaging.

The calibration phantoms can be imaged before or after the x-ray image is taken. Alternatively, the calibration phantom can be imaged at the same time as the x-ray image. The calibration phantom can be physically connected to an x-ray film and/or film holder. Such physical connection can be achieved using any suitable mechanical or other attachment mechanism, including but not limited to adhesive, a chemical bond, use of screws or nails, welding, a Velcro™ strap or Velcro™ material and the like. Similarly, a calibration phantom can be physically connected to a detector system or a storage plate for digital x-ray imaging using one or more attachment mechanisms (e.g., a mechanical connection device, a Velcro™ strap or other Velcro™ material, a chemical bond, use of screws or nails, welding and an adhesive). The external standard and the film can be connected with use of a holding device, for example using press fit for both film and external standard.

Additionally, the calibration phantom assembly can be attached to an anatomical structure, for example one or more teeth, mucus membranes, the mandible and/or maxilla. For instance, the calibration phantom can be attached (e.g., via adhesive attachment means) to the epithelium or mucous membrane inside overlying the mandible or the maxilla. Alternatively, the calibration phantom can be placed on or adjacent to a tooth, for example, a V- or U-shaped (in the case of the maxilla) or an inverted V- or U-shaped (in the case of the mandible) calibration phantom can be used. The opening of the V or U will be in contact with the free edge of at least one tooth or possibly several teeth (FIG. 4).

In preferred embodiments, when an x-ray of an anatomic structure or a non-living object is acquired a calibration phantom is included in the field of view. Any suitable calibration phantom can be used, for example, one that comprises aluminum or other radio-opaque materials. U.S. Pat. No. 5,335,260 describes other calibration phantoms suitable for use in assessing bone mineral density in images. Examples of other suitable calibration reference materials can be fluid or fluid-like materials, for example, one or more chambers filled with varying concentrations of calcium chloride or the like. In a preferred embodiment, the material of the phantom is stainless steel (e.g., AISI grade 316 comprising carbon (0.08%); manganese (2%); silicon (1%); phosphorus (0.045%); sulphur (0.03%); nickel (10-14%); chromium (16-18%); molybdenum (2-3%); plus iron to make up 100%). The relative percentages of the components may be with respect to weight or volume.

It will be apparent that calibration phantoms suitable for attachment to an anatomical structure can have different shapes depending on the shape of the anatomical structure (e.g., tooth or teeth) on which or adjacent to which it will be placed including, but not limited to, U-shaped, V-shaped, curved, flat or combinations thereof. For example, U-shaped (or inverted U-shaped) calibration phantoms can be positioned on top of molars while V-shaped (or inverted V-shaped) calibration phantoms can be positioned on top of incisors. Further, it will be apparent that in certain instances (e.g., teeth on the mandible), the calibration phantom can rest on top of the tooth just based on its gravity or it can be attached to the tooth (e.g., using adhesive). In the case of the teeth on the maxilla, the calibration phantom will typically be attached to the tooth, for example with use of an adhesive.

Any of these attachments may be permanent or temporary and the calibration phantom can be integral (e.g., built-in) to the film, film holder and/or detector system or can be attached or positioned permanently or temporarily appropriately after the film and/or film holder is produced. Thus, the calibration phantom can be designed for single-use (e.g., disposable) or for multiple uses with different x-ray images. Thus, in certain embodiments, the calibration phantom is reusable and, additionally, can be sterilized between uses. Integration of a calibration phantom can be achieved by including a material of known x-ray density between two of the physical layers of the x-ray film. Integration can also be achieved by including a material of known x-ray density within one of the physical layers of the x-ray film. Additionally, the calibration phantom can be integrated into the film cover. A calibration phantom or an external standard can also be integrated into a detector system or a storage plate for digital x-ray imaging. For example, integration can be achieved by including a material of known x-ray density between two of the physical layers of the detector system or the storage plate. Integration can also be achieved by including a material of know x-ray density within one of the physical layers of the detector system or the storage plate.

In certain embodiments, for example those embodiments in which the calibration phantom is temporarily attached to a component of the x-ray assembly system (e.g., x-ray film holder, x-ray film, detector system or the like), cross-hairs, lines or other markers may be placed on the apparatus as indicators for positioning of the calibration phantom. These indicators can help to ensure that the calibration phantom is positioned such that it doesn't project on materials that will alter the apparent density in the resulting image.

Any of the calibration phantom-containing assemblies described herein can be used in methods of analyzing and/or quantifying bone structure and/or one or more macro-anatomical and/or biomechanical parameters (or bone mineral density) in an x-ray image. The methods generally involve simultaneously imaging or scanning the calibration phantom and another material (e.g., bone tissue from a subject) for the purpose of quantifying the density of the imaged material (e.g., bone mass). In the case of dental radiographs, the calibration phantom, the x-ray tube or dental x-ray film is typically positioned in a manner to ensure inclusion of the calibration phantom and a portion of the mandible and/or maxilla on the dental x-ray image. Preferably, the calibration phantom, the x-ray tube and the dental x-ray film are positioned so that at least a portion of the section of the mandible or maxilla included on the image will contain predominantly trabecular bone rather than cortical bone.

Thus, under the method of the present invention, the calibration phantom is preferably imaged or scanned simultaneously with the individual subject, although the invention allows for non-simultaneous scanning of the phantom and the subject. Methods of scanning and imaging structures by x-ray imaging technique are well known. By placing the calibration phantom in the x-ray beam with the subject, reference calibration samples allow corrections and calibration of the absorption properties of bone. When the phantom is imaged or scanned simultaneously with each subject, the variation in x-ray beam energy and beam hardening are corrected since the phantom and the subject both see the same x-ray beam spectrum. Each subject, having a different size, thickness, muscle-to-fat ratio, and bone content, attenuate the beam differently and thus change the effective x-ray beam spectrum. It is necessary that the bone-equivalent calibration phantom be present in the same beam spectrum as the subject's bone to allow accurate calibration.

X-ray imaging assemblies that are currently in use do not take into account the position of the calibration phantom in relation to the structures being imaged. Thus, when included in known assemblies, calibration phantom(s) are often positioned such that they project on materials or structures (e.g., bone) that alter apparent density of the calibration phantom in the resulting x-ray image. Clearly, this alteration in apparent density will affect the accuracy of the calibration phantom as a reference for determining bone mineral density, structure or macro-anatomical parameters. Therefore, it is an object of the invention to provide methods in which the calibration phantom projects free of materials or structures that will alter the apparent density of the reference. In the context of dental x-rays, for instance, the methods described herein ensure that the calibration phantom projects free of bone (e.g., teeth, jaw) tissue. This can be accomplished in a variety of ways, for example, positioning the calibration phantom in the x-ray film or in the x-ray film holder such that it will appear between the teeth in the dental x-ray.

The calibration phantom materials and methods of the present invention are preferably configured to be small enough and thin enough to be placed inside the mouth, and the method of the present invention can be used to quantify bone mass using standard dental x-ray systems, for example by including temporary or permanent calibration phantoms in dental x-ray film holders. Further, it is highly desirable that the calibration phantom be positioned so that at least a portion doesn't project on structures or materials that will alter the apparent density or structural characteristics of the calibration phantoms. It is also preferable to position calibration phantom at a defined distance relative to at least one tooth or the mandible or the maxilla whereby a substantial portion of the calibration phantom projects free of said tooth, said mandible or said maxilla on the x-ray image. Any suitable distance can be used, for example between about 1 mm and 5 cm or any value therebetween.

A cross-calibration phantom can be used to optimize system performance, e.g. x-ray tube settings or film processor settings, or to improve the comparability of different machines or systems, typically located at different sites. For this purpose, a separate image may be obtained which does not include a patient or a body part. The image includes the primary calibration phantom used in patients, e.g. a stepwedge of known density, and the cross-calibration phantom. The apparent density of the primary calibration phantom is then calibrated against the density of the cross-calibration phantom. The resultant cross-calibration of the primary phantom can help to improve the accuracy of measurements of bone density, bone structure and macro-anatomical and/or biomechanical parameters. It can also help improve the overall reproducibility of the measurements. In one embodiment of the invention, an x-ray technologist or a dental hygienist will perform a cross-calibration test once a day, typically early in the morning, prior to the first patient scans. The results of the cross-calibration or the entire cross-calibration study can be transmitted via a network to a central computer. The central computer can then perform adjustments designed to maintain a high level of comparability between different systems.

1.2. Inherent Reference Markers

In certain embodiments of the invention, information inherent in the anatomic structure or the non-living object can be used to estimate the density and/or structure and/or macro-anatomy of selected bone regions of interest within the anatomic structure or the non-living object. For example, since the density of muscle, fat, water (e.g., soft tissue), metal (e.g., dental fillings) and air are typically known, the density of air surrounding an anatomic structure or non-living object, the density of subcutaneous fat, and the density of muscle tissue can be used to estimate the density of a selected region of bone, for example within the distal radius. For instance, a weighted mean can be determined between one or more of the internal standards (e.g., air, water, metal, and/or fat) and used as internal standards to determine bone density in the same x-ray image. Similarly, the density of a tooth or a portion of a tooth can be used to estimate the density of a selected region of bone, e.g. an area in the mandible.

The information inherent in said anatomic structure can also be combined with information provided by the calibration phantom and the combination can result in an improved accuracy of the calibration phantom.

1.3. Holders and Hygienic Covers

Figure 5:
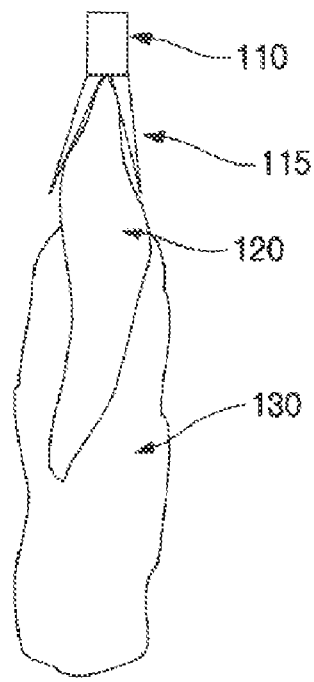
FIG. 5 shows an example of a holder 115 for a calibration phantom 110. The holder 115 is mounted on a tooth 120. Gums are also shown 130.
Figure 6A:
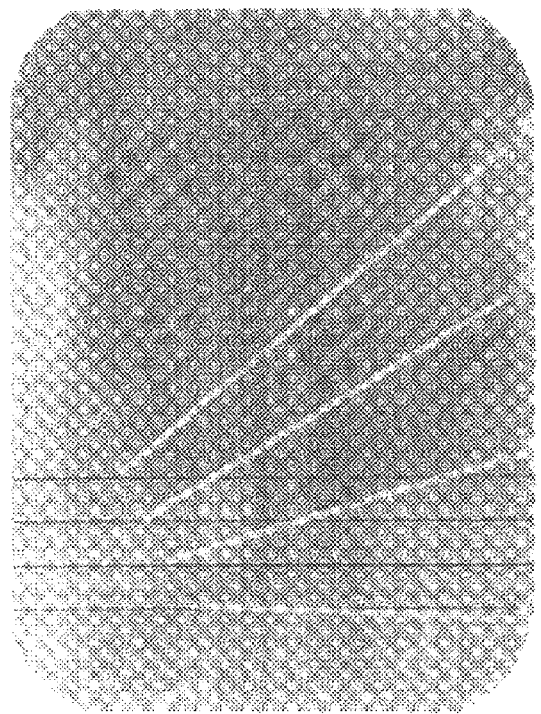
FIG. 6, panels B through E shows gray value profiles along different rows of pixels used for locating dental apices. From top to bottom, the characteristic peaks for the dental roots (shown in dental x-ray panel A) gradually disappear.
Figure 6B:
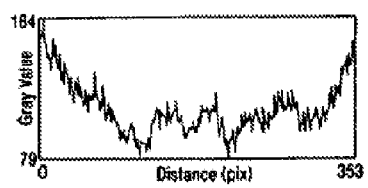
Figure 6C:
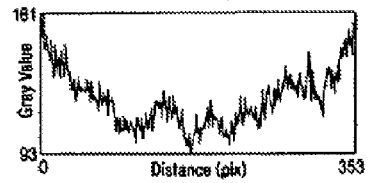
Figure 6D:
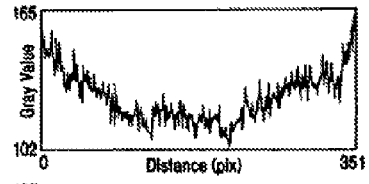
Figure 6E:
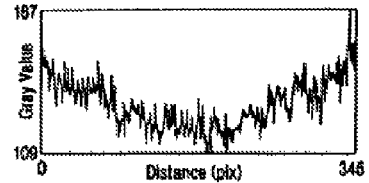

As noted above, in certain embodiments, a holder can be used to position the calibration phantom. The holder can be U-shaped or V-shaped (FIG. 5) for ease in attachment to a tooth. The attachment can be, for example, with an adhesive. The calibration phantom, in turn, can be attached to the holder. Similarly, the calibration phantom can be attached to holders comprising one or more molds of at least one or more teeth. Additionally, the holder can be used to position both the film and the calibration phantom relative to the osseous structure that will be included in the x-ray image. In another embodiment, a holding device that can hold the x-ray film is integrated in the calibration phantom. This holding device can hold the film in place prior to taking the x-ray. The holding device can be spring-loaded or use other means such as mechanical means of holding and stabilizing the x-ray film.

In certain embodiments, the holder may comprise a disposable or sterilizable hygienic cover. See, e.g., WO 99/08598, the disclosure of which is incorporated by reference herein in its entirety. Furthermore, the holder may comprise multiple components, for example, the calibration phantom and a integrated or insertable bolus back that can serve to enhance the accuracy of the calibration phantom by accounting for the effect of soft tissue that may project with the calibration phantom and/or with the bone.

In certain embodiments, the calibration phantom can be configured so that it stabilizes against the surrounding tissues on its own without the use of an additional holder. The calibration phantom can be protected with a hygienic cover.

The holder (e.g., hygienic cover) may be comprised of a rigid material, a flexible material or combinations thereof. Furthermore, the holder may include one or more pockets/compartments adapted to receive additional components such as the calibration phantom, a bolus back or the like. Additionally, one or more portions of the holder may be radiolucent.

2.0. Analysis and Manipulation of Data

The data obtained from images taken as described above is then preferably analyzed and manipulated. Thus, the systems and assemblies described herein can also include one or more computational units designed, for example, to analyze bone density or bone structure or macro-anatomical and/or biomechanical data in the image; to identify an anatomical landmark in an anatomical region; to correct for soft tissue measurements; and/or to evaluate bone density and structure and macro-anatomy of the image. As will be appreciated by those of skill in the art, the computational unit can include any software, chip or other device used for calculations. Additionally, the computational unit may be designed to control the imaging assembly or detector (as well as other parameters related to the detector(s)). Other applications of the computational unit to the methods and devices described herein will be recognized by those skilled in the art. The computational unit may be used for any other application related to this technology that may be facilitated with use of computer software or hardware. The computational unit can also further comprise a database comprising, for example, reference anatomical maps and the computational unit is further designed to compare the anatomical map with the reference anatomical map. The reference anatomical map may be historic (from the same or another patient, generated as part of an interrogation protocol), or theoretical or any other type of desired reference map.

Any image can be analyzed in order to obtain and manipulate data. Thus, data points, derived data, and data attributes database according to the present invention may comprise the following: (1) the collection of data points, said data points comprising information obtained from an image, for example, bone mineral density information or information on bone structure (architecture); and (2) the association of those data points with relevant data point attributes. The method may further comprise (3) determining derived data points from one or more direct data points and (4) associating those data points with relevant data point attributes. The method may also comprise (5) collection of data points using a remote computer whereby said remote computer operates in a network environment.

In certain preferred embodiments, the information is obtained from a dental x-ray image. As described herein, dental x-ray images can be acquired at a local site using known techniques. If the x-ray image was captured using conventional x-ray film, the data points (information) of the x-ray image can be digitized using a scanning device. The digitized x-ray image information can then be transmitted over the network, e.g. the Internet, into a remote computer or server. If the x-ray image was acquired using digital acquisition techniques, e.g. using phosphorus plate systems or selenium or silicon detector systems, the x-ray image information is already available in digital format. In this case the image can be transmitted directly over the network, e.g. the Internet. The information can also be compressed and/or encrypted prior to transmission. Transmission can also be by other methods such as fax, mail or the like.

2.1. Data Points

Thus, the methods of and compositions described herein make use of collections of data sets of measurement values, for example measurements of bone structure and/or bone mineral density from x-ray images. Records may be formulated in spreadsheet-like format, for example including data attributes such as date of x-ray, patient age, sex, weight, current medications, geographic location, etc. The database formulations may further comprise the calculation of derived or calculated data points from one or more acquired data points. A variety of derived data points may be useful in providing information about individuals or groups during subsequent database manipulation, and are therefore typically included during database formulation. Derived data points include, but are not limited to the following: (1) maximum bone mineral density, determined for a selected region of bone or in multiple samples from the same or different subjects; (2) minimum bone mineral density, determined for a selected region of bone or in multiple samples from the same or different subjects; (3) mean bone mineral density, determined for a selected region of bone or in multiple samples from the same or different subjects; (4) the number of measurements that are abnormally high or low, determined by comparing a given measurement data point with a selected value; and the like. Other derived data points include, but are not limited to the following: (1) maximum value of a selected bone structure parameter, determined for a selected region of bone or in multiple samples from the same or different subjects; (2) minimum value of a selected bone structure parameter, determined for a selected region of bone or in multiple samples from the same or different subjects; (3) mean value of a selected bone structure parameter, determined for a selected region of bone or in multiple samples from the same or different subjects; (4) the number of bone structure measurements that are abnormally high or low, determined by comparing a given measurement data point with a selected value; and the like. Other derived data points include, but are not limited to the following: (1) maximum value of a selected macro-anatomical and/or biomechanical parameter, determined for a selected region of bone or in multiple samples from the same or different subjects; (2) minimum value of a selected macro-anatomical and/or biomechanical parameter, determined for a selected region of bone or in multiple samples from the same or different subjects; (3) mean value of a selected macro-anatomical and/or biomechanical parameter, determined for a selected region of bone or in multiple samples from the same or different subjects; (4) the number of macro-anatomical and/or biomechanical measurements that are abnormally high or low, determined by comparing a given measurement data point with a selected value; and the like. Other derived data points will be apparent to persons of ordinary skill in the art in light of the teachings of the present specification. The amount of available data and data derived from (or arrived at through analysis of) the original data provide provides an unprecedented amount of information that is very relevant to management of bone related diseases such as osteoporosis. For example, by examining subjects over time, the efficacy of medications can be assessed.

Measurements and derived data points are collected and calculated, respectively, and may be associated with one or more data attributes to form a database. The amount of available data and data derived from (or arrived at through analysis of) the original data provide provides an unprecedented amount of information that is very relevant to management of bone related diseases such as osteoporosis. For example, by examining subjects over time, the efficacy of medications can be assessed.

Data attributes can be automatically input with the x-ray image and can include, for example, chronological information (e.g., DATE and TIME). Other such attributes may include, but are not limited to, the type of x-ray imager used, scanning information, digitizing information and the like. Alternatively, data attributes can be input by the subject and/or operator, for example subject identifiers, i.e. characteristics associated with a particular subject. These identifiers include but are not limited to the following: (1) a subject code (e.g., a numeric or alpha-numeric sequence); (2) demographic information such as race, gender and age; (3) physical characteristics such as weight, height and body mass index (BMI); (4) selected aspects of the subject's medical history (e.g., disease states or conditions, etc.); and (5) disease-associated characteristics such as the type of bone disorder, if any; the type of medication used by the subject. In the practice of the present invention, each data point would typically be identified with the particular subject, as well as the demographic, etc. characteristic of that subject.

Other data attributes will be apparent to persons of ordinary skill in the art in light of the teachings of the present specification.

2.2. Storage of Data Sets and Association of Data Points with Relevant Data Attributes A number of formats exist for storing data sets and simultaneously associating related attributes, including but not limited to (1) tabular, (2) relational, and (3) dimensional. In general the databases comprise data points, a numeric value which correspond to physical measurement (an "acquired" datum or data point) or to a single numeric result calculated or derived from one or more acquired data points that are obtained using the various methods disclosed herein. The databases can include raw data or can also include additional related information, for example data tags also referred to as "attributes" of a data point. The databases can take a number of different forms or be structured in a variety of ways.

The most familiar format is tabular, commonly referred to as a spreadsheet. A variety of spreadsheet programs are currently in existence, and are typically employed in the practice of the present invention, including but not limited to Microsoft Excel spreadsheet software and Corel Quattro spreadsheet software. In this format, association of data points with related attributes occurs by entering a data point and attributes related to that data point in a unique row at the time the measurement occurs.

Further, rational, relational (Database Design for Mere Mortals, by Michael J. Hernandez, 1997, Addison-Wesley Pub. Co., publisher; Database Design for Smarties, by Robert J. Muller, 1999, Morgan Kaufmann Publishers, publisher; Relational Database Design Clearly Explained, by Jan L. Harrington, 1998, Morgan Kaufmann Publishers, publisher) and dimensional (Data-Parallel Computing, by V. B. Muchnick, et al., 1996, International Thomson Publishing, publisher; Understanding Fourth Dimensions, by David Graves, 1993, Computerized Pricing Systems, publisher) database systems and management may be employed as well.

Relational databases typically support a set of operations defined by relational algebra. Such databases typically include tables composed of columns and rows for the data included in the database. Each table of the database has a primary key, which can be any column or set of columns, the values for which uniquely identify the rows in a table. The tables in the database can also include a foreign key that is a column or set of columns, the values of which match the primary key values of another table. Typically, relational databases also support a set of operations (e.g., select, join and combine) that form the basis of the relational algebra governing relations within the database.

Such relational databases can be implemented in various ways. For instance, in Sybase® (Sybase Systems, Emeryville, Calif.) databases, the tables can be physically segregated into different databases. With Oracle® (Oracle Inc., Redwood Shores, Calif.) databases, in contrast, the various tables are not physically separated, because there is one instance of work space with different ownership specified for different tables. In some configurations, databases are all located in a single database (e.g., a data warehouse) on a single computer. In other instances, various databases are split between different computers.

It should be understood, of course, that the databases are not limited to the foregoing arrangements or structures. A variety of other arrangements will be apparent to those of skill in the art.

2.3. Data Manipulation

Data obtained from x-ray images as described herein can be manipulated, for example, using a variety of statistical analyses, to produce useful information. The databases of the present invention may be generated, for example, from data collected for an individual or from a selected group of individuals over a defined period of time (e.g., days, months or years), from derived data, and from data attributes.

For example, data may be aggregated, sorted, selected, sifted, clustered and segregated by means of the attributes associated with the data points. A number of data mining software programs exist which may be used to perform the desired manipulations.

Relationships in various data can be directly queried and/or the data analyzed by statistical methods to evaluate the information obtained from manipulating the database.

For example, a distribution curve can be established for a selected data set, and the mean, median and mode calculated therefor. Further, data spread characteristics, e.g. variability, quartiles and standard deviations can be calculated.

The nature of the relationship between any variables of interest can be examined by calculating correlation coefficients. Useful methods for doing so include but are not limited to the following: Pearson Product Moment Correlation and Spearman Rank Order Correlation.

Analysis of variance permits testing of differences among sample groups to determine whether a selected variable has a discernible effect on the parameter being measured.

Non-parametric tests may be used as a means of testing whether variations between empirical data and experimental expectancies are attributable merely to chance or to the variable or variables being examined. These include the Chi Square test, the Chi Square Goodness of Fit, the 2×2 Contingency Table, the Sign Test, and the Phi Correlation Coefficient.

There are numerous tools and analyses available in standard data mining software that can be applied to the analysis of the databases of the present invention. Such tools and analyses include, but are not limited to, cluster analysis, factor analysis, decision trees, neural networks, rule induction, data driven modeling, and data visualization. Some of the more complex methods of data mining techniques are used to discover relationships that are more empirical and data-driven, as opposed to theory-driven, relationships.

Exemplary data mining software that can be used in analysis and/or generation of the databases of the present invention includes, but is not limited to: Link Analysis (e.g., Associations analysis, Sequential Patterns, Sequential time patterns and Bayes Networks); Classification (e.g., Neural Networks Classification, Bayesian Classification, k-nearest neighbors classification, linear discriminant analysis, Memory based Reasoning, and Classification by Associations); Clustering (e.g., k-Means Clustering, demographic clustering, relational analysis, and Neural Networks Clustering); Statistical methods (e.g., Means, Std dev, Frequencies, Linear Regression, non-linear regression, t-tests, F-test, Chi2 tests, Principal Component Analysis, and Factor Analysis); Prediction (e.g., Neural Networks Prediction Models, Radial Based Functions predictions, Fuzzy logic predictions, Times Series Analysis, and Memory based Reasoning); Operating Systems; and Others (e.g., Parallel Scalability, Simple Query Language functions, and C++ objects generated for applications). Companies that provide such software include, for example, the following: Adaptative Methods Group at UTS (UTS City Campus, Sydney, NSW 2000), CSI®, Inc., (Computer Science Innovations, Inc. Melbourne, Fla.), IBM® (International Business Machines Corporation, Armonk, N.Y.), Oracle (Oracle Inc., Redwood Shores, Calif.) and SAS® (SAS Institute Inc., Cary, N.C.).

These methods and processes may be applied to the data obtained using the methods described herein, for example, databases comprising, x-ray image data sets, derived data, and data attributes.

In certain embodiments, data (e.g., bone structural information or macro-anatomical and/or biomechanical information or bone mineral density information) is obtained from normal control subjects using the methods described herein. These databases are typically referred to as "reference databases" and can be used to aid analysis of any given subject's x-ray image, for example, by comparing the information obtained from the subject to the reference database. Generally, the information obtained from the normal control subjects will be averaged or otherwise statistically manipulated to provide a range of "normal" (reference) measurements. Suitable statistical manipulations and/or evaluations will be apparent to those of skill in the art in view of the teachings herein.

ADD z-score, T-scores here; other statistical measurements that you deem important. The comparison of the subject's x-ray information to the reference database can be used to determine if the subject's bone information falls outside the normal range found in the reference database or is statistically significantly different from a normal control. Data comparison and statistical significance can be readily determined by those of skill in the art using for example the z-test or t-test statistics for continuous variables, the chi-square test or Fisher's exact test for categorical data and the rank-sum test or Kruskal-Wallis test for ranked data. The use of reference databases in the analysis of x-ray images facilitates that diagnosis, treatment and monitoring of bone conditions such as osteoporosis.

For a general discussion of statistical methods applied to data analysis, see Applied Statistics for Science and Industry, by A. Romano, 1977, Allyn and Bacon, publisher.

The data is preferably stored and manipulated using one or more computer programs or computer systems. These systems will typically have data storage capability (e.g., disk drives, tape storage, CD-ROMs, etc.). Further, the computer systems may be networked or may be stand-alone systems. If networked, the computer system would be able to transfer data to any device connected to the networked computer system for example a medical doctor or medical care facility using standard e-mail software, a central database using database query and update software (e.g., a data warehouse of data points, derived data, and data attributes obtained from a large number of subjects). Alternatively, a user could access from a doctor's office or medical facility, using any computer system with Internet access, to review historical data that may be useful for determining treatment.

If the networked computer system includes a World Wide Web application, the application includes the executable code required to generate database language statements, for example, SQL statements. Such executables typically include embedded SQL statements. The application further includes a configuration file that contains pointers and addresses to the various software entities that are located on the database server in addition to the different external and internal databases that are accessed in response to a user request. The configuration file also directs requests for database server resources to the appropriate hardware, as may be necessary if the database server is distributed over two or more different computers.

Usually each networked computer system includes a World Wide Web browser that provides a user interface to the networked database server. The networked computer system is able to construct search requests for retrieving information from a database via a Web browser. With access to a Web browser users can typically point and click to user interface elements such as buttons, pull down menus, and other graphical user interface elements to prepare and submit a query that extracts the relevant information from the database. Requests formulated in this manner are subsequently transmitted to the Web application that formats the requests to produce a query that can be used to extract the relevant information from the database.

When Web-based applications are utilized, the Web application accesses data from a database by constructing a query in a database language such as Sybase or Oracle SQL which is then transferred to a relational database management system that in turn processes the query to obtain the pertinent information from the database.

Accordingly, in one aspect the present invention describes a method of providing data obtained from x-ray images on a network, for example the Internet, and methods of using this connection to provide real-time and delayed data analysis. The central network can also allow access by the physician to a subject's data. Similarly, an alert could be sent to the physician if a subject's readings are out of a predetermined range, etc. The physician can then send advice back to the patient via e-mail or a message on a web page interface. Further, access to the entire database of data from all subjects may be useful for statistical or research purposes. Appropriate network security features (e.g., for data transfer, inquiries, device updates, etc.) are of course employed.

Further, a remote computer can be used to analyze the x-ray that has been transmitted over the network automatically. For example, x-ray density information or structural information about an object can be generated in this fashion. X-ray density information can, for example, be bone mineral density. If used in this fashion, the test can be used to diagnose bone-related conditions such as osteoporosis.

2.4. Graphical User Interface

In certain of the computer systems, an interface such as an interface screen that includes a suite of functions is included to enable users to easily access the information they seek from the methods and databases of the invention. Such interfaces usually include a main menu page from which a user can initiate a variety of different types of analyses. For example, the main menu page for the databases generally include buttons for accessing certain types of information, including, but not limited to, project information, inter-project comparisons, times of day, events, dates, times, ranges of values, etc.

2.5. Computer Program Products

A variety of computer program products can be utilized for conducting the various methods and analyses disclosed herein. In general, the computer program products comprise a computer-readable medium and the code necessary to perform the methods set forth supra. The computer-readable medium on which the program instructions are encoded can be any of a variety of known medium types, including, but not limited to, microprocessors, floppy disks, hard drives, ZIP drives, WORM drives, magnetic tape and optical medium such as CD-ROMs.

For example, once an image or data from that image is transmitted via a local or long-distance computer network and the data received by a remote computer or a computer connected to the remote network computer, an analysis of the morphology and density of the bone can be performed, for example using suitable computer programs. This analysis of the object's morphology can occur in two-dimensions or three-dimensions. For example, in imaging osseous structures, such analysis of the transmitted x-ray image can be used to measure parameters that are indicative or suggestive of bone loss or metabolic bone disease. Such parameters include all current and future parameters that can be used to evaluate osseous structures. For example, such parameters include, but are not limited to, trabecular spacing, trabecular thickness, trabecular connectivity and intertrabecular space.

Information on the morphology or 2D or 3D structure of an anatomic object can be derived more accurately, when image acquisition parameters such as spatial resolution are known. Other parameters such as the degree of cone beam distortion can also be helpful in this setting.

As noted above, an image can be transmitted from a local site into a remote server and the remote server can perform an automated analysis of the image. Further, the remote server or a computer connected to the remote server can then generate a diagnostic report. Thus, in certain embodiments, a computer program (e.g., on the remote server or on a computer connected to the remote server) can generate charges for the diagnostic report. The remote server can then transmit the diagnostic report to a physician, typically the physician who ordered the test or who manages the patient. The diagnostic report can also be transmitted to third parties, e.g. health insurance companies. Such transmission of the diagnostic report can occur electronically (e.g. via e-mail), via mail, fax or other means of communication. All or some of the transmitted information (e.g., patient identifying information) can be encrypted to preserve confidentiality of medical records.

Thus, one exemplary system is described herein for analyzing bone morphology or structure in a subject system via a dental x-ray that includes at least a portion of the mandible and/or maxilla of a subject, followed by evaluation or the x-ray image. Dental x-rays are obtained in any conventional method. The x-ray produces an image that can be interpreted (for example, employing a selected algorithm and/or computer program) by an associated system controller to provide a bone mineral density or bone structure evaluation for display.

In a further aspect of the present invention, the monitoring system can comprise two or more components, in which a first component comprises an x-ray image and calibration phantom that are used to extract and detect bone-related data on the subject, and a second component that receives the data from the first component, conducts data processing on the data and then displays the processed data. Microprocessor functions can be found in one or both components. The second component of the monitoring system can assume many forms

3.0.0.0 Correction Factors

Although the presence of calibration phantoms greatly aids in increasing the accuracy of data obtained from images such as dental, hip or spine x-rays, the present inventors also recognize that, in certain instances, there may be a need to apply one or more correction factors to further enhance accuracy of the data obtained from any given x-ray image. Such correction factors will take into account one or more of a wide variety of influences (e.g., soft tissue thickness, region from which the data is extracted and the like) that can alter apparent density or structure information on the image.

In this regard, one or more reference databases can be used for calibration and normalization purposes. For example, image normalization or correction of soft-tissue attenuation can be performed using patient characteristic data such as patient weight, height and body mass index. In one example, a higher soft-tissue attenuation can be assumed in high weight and low height subjects; a lower soft-tissue attenuation will be assumed in low weight and high height subjects.

In another embodiment, a standard calibration curve is applied to x-ray images, whereby said calibration curve can be derived from reference x-rays obtained with use of calibration phantoms. For example, 100 patients can undergo dental x-rays with a calibration phantom and a standard calibration curve can be derived from these images. Similarly, 100 patients can undergo hip x-rays with a calibration phantom and a standard calibration curve can be derived from these images. Different calibration curves can be generated for different populations, for example, by generating different calibration curves for different ranges in body mass index, body height, sex, race etc.

3.1.0.0. Anatomical Landmarks

In one embodiment, identification of anatomic landmarks of the structure to be analyzed or identification of anatomical landmarks adjacent to the structure to be analyzed with subsequent positioning and computer analysis of the x-ray image relative to these anatomic landmarks or with subsequent positioning and computer analysis of anatomical region of interest (ROI) relative to these anatomic landmarks is performed. The present invention includes also positioning dental or other x-ray detectors, positioning the dental or other x-ray tube, and analyzing the resulting images using landmarks based on either 1) textural information, 2) structural information, 3) density information (e.g. density), or 4) 2 or 3 dimensional contour information 5) a combinations thereof of the tissue or structure to be measured and of tissues or structures adjacent to the measurement site. The invention also includes methods and devices that are not necessarily based solely on anatomical landmarks, but in some applications can be combined with anatomical landmark embodiments. Preferably, many of the embodiments described herein are designed for automated use with a minimum of operator intervene and preferably remote or computer control of such devices.

Figure 15:
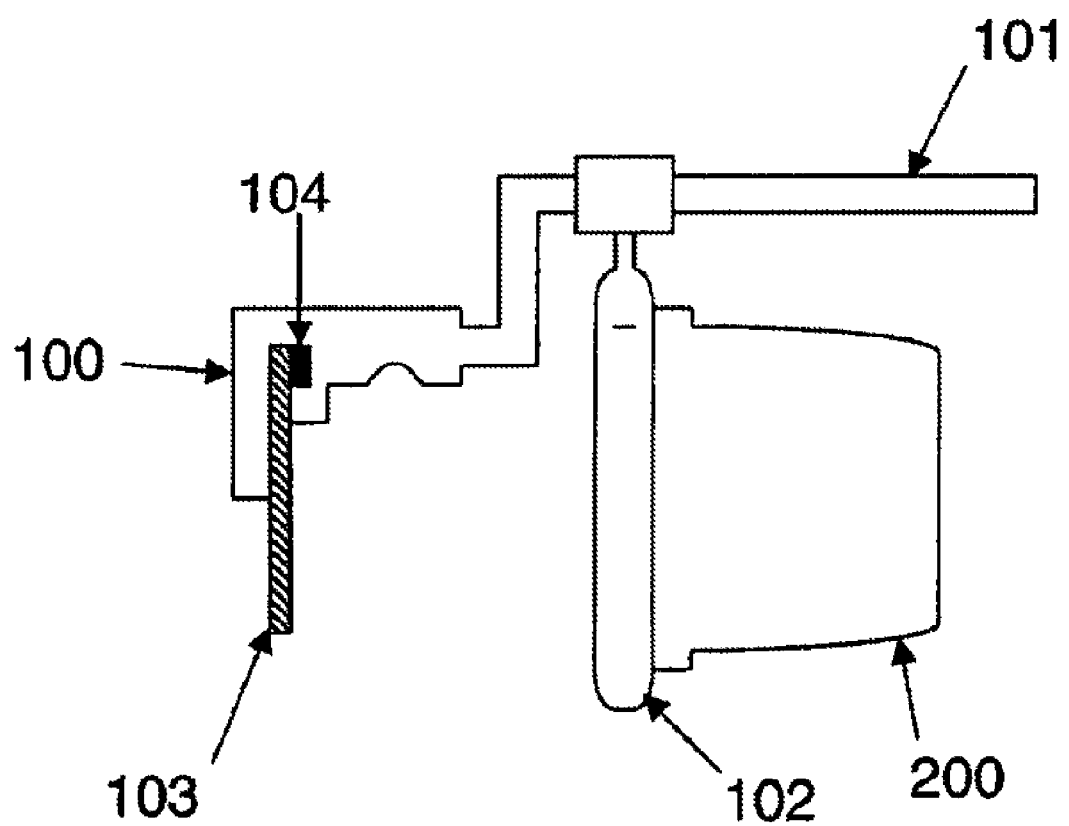
FIG. 15 is a side view of an exemplary system for minimizing tube angulation as described herein. In the Figure, the system is shown as a dental x-ray system. An extension tubing (200) is attached to a ring-shaped Rinn holder (102). The outer diameter of the extension tubing is slightly smaller than the inner diameter of the tube located in front of the dental x-ray system/dental x-ray tube. The extension tubing can then be inserted into the metal tube thereby reducing tube angulation and resultant errors in bone apparent density and bone structural measurements.

In one embodiment, an alignment device may be used to ensure perpendicular or near perpendicular alignment of the dental or other x-ray tube relative to the x-ray film, thereby decreasing geometric distortion resulting from tube angulation. For example, an x-ray film holder is positioned relative to an anatomical landmark, e.g. the posterior wall of the mandible in the incisor region. A side-view of an exemplary alignment system using a dental x-ray film holder is shown in FIG. 15. The system includes bite block (100), stainless steel rod (101), film (103), optional calibration phantom (104), Rinn holder (102) typically having a ring or donut shape, and extension tubing (200). The extension tubing is designed to fit within the Rinn holder and may be temporarily or permanently attached. The system can achieve high reproducibility of the film position relative to an anatomical landmark such as the alveolar ridge or the posterior wall of the mandible. The extension tubing allows for alignment of the x-ray tube so that it is near perpendicular to the Rinn instrument and, ultimately, the dental film.

Since manual alignment of the dental x-ray tube, namely the tube (e.g., metal) located in front of the dental x-ray tube for pointing and alignment purposes, is often not very accurate with alignment errors of 3, 5 or even more degrees, a mechanical or electromagnetic device is preferably used in order to achieve perpendicular or near perpendicular alignment between the metal tube anterior to the x-ray tube and the Rinn holder. For example, the metal tube can be physically attached to the Rinn holder with use of one or more Velcro™ straps or it can be aligned using optical aids such as levels, cross-hairs, light sources (points or areas), etc. Alternatively, such physical attachment can be achieved with use of one or more magnets rigidly attached to the dental x-ray system metal tube and the Rinn holder. In this embodiment, the magnets on the Rinn holder and the dental x-ray system metal tube will be aligned and brought into physical contact. In another embodiment, an extension tube is attached, for example with an adhesive, to the Rinn holder. The extension tubing can also be an integral part of the Rinn holder. The extension tubing can be designed so that its inner diameter is slightly greater than the outer diameter of the dental x-ray system metal tube. The dental x-ray system metal tube is then inserted into the extension tubing attached to the Rinn holder thereby greatly reducing alignment error of the x-ray tube relative to the x-ray film. Alternatively, the extension tubing can be designed so that its outer diameter is slightly smaller than the inner diameter of the dental x-ray system metal tube. The dental x-ray system metal tube is then advanced over the extension tubing attached to the Rinn holder thereby greatly reducing alignment error of the x-ray tube relative to the x-ray film. One of skill in the art will easily recognize in view of the teachings herein that many other attachment means can be used for properly aligning the dental x-ray tube with the dental x-ray film. Combinations of attachment mechanisms are also possible.

The anatomical landmark that is selected is part of an anatomical region. An anatomical region refers to a site on bone, tooth or other definable biomass that can be identified by an anatomical feature(s) or location. An anatomical region can include the biomass underlying the surface. Usually, such a region will be definable according to standard medical reference methodology, such as that found in Williams et al., Gray's Anatomy, 1980. The anatomical region can be selected from the group consisting of an edge of the mandible, an edge of the maxilla, an edge of a tooth, valleys or grooves in any of these structures or combinations thereof. The dental x-ray image can be readily taken so as to include the anatomical site. Other anatomical regions include but are not limited to the hip, the spine, the forearm, the foot, and the knee.

For example, the region of interest is placed between the dental apices and the inferior mandibular cortex. The apices can be found automatically in the following way: for each row of pixels, the gray value profile is examined. While a profile that intersects bone and dental roots in an alternating fashion has several distinct peaks and valleys, a profile that only covers trabecular bone shows irregular changes in the gray values (FIG. 6). The dental apices are located in the transitional region between these two patterns.

The measurement techniques to assess trabecular bone structure or macro-anatomical and/or biomechanical parameters are preferably designed to work without user intervention. In order to fully automate the process of analyzing dental x-rays, it is necessary to develop a technique to locate the regions of interest (ROIs) that are used for the calculation of the structural parameters of the trabecular bone. If the profile for a particular row of pixels contains distinct peaks, their number, width and height can be determined. Next, the rows below these lines can be evaluated until the peaks have disappeared. This line determines the boundary, 5 mm below which the ROI can be placed in the center between the longitudinal axes of the roots, which can also be determined from the row profiles (FIG. 6). At a pixel size of 0.042 mm×0.042 mm, which corresponds to a resolution of 600 dpi, the ROI has a size of 5.4 mm×5.4 mm (128×128 pixels). For other scanning resolutions, the pixel resolution of the ROI can be adjusted accordingly.

In the case of an edentulous patient, bone mineral density can be measured in all ROIs that are located on a line that is, for example, 8 mm inferior and parallel to the alveolar ridge. The ROIs can be moved from left to right on a pixel-by-pixel basis. Eventually, the ROI with the lowest BMD can be chosen for further evaluation of the structural bone parameters. This helps to avoid inclusion of regions on the x-ray where bone mineral density may be overestimated due to projection of the curved parts of the mandible near the canine teeth. Alternatively, the ROI with the median BMD can be used. Other statistical parameters can be employed for this purpose.

Thus, software or other computational unit can identify the selected anatomic landmark in an interrogated x-ray image and direct analysis of the image using various parameters and analytic functions. Further, such software or other computational analytical unit can be used to identify areas of particular density at a certain distance from the selected landmark. Similarly, manual or computer analysis can be used to identify areas of lowest, highest, median or average density (or structural characteristics) in relation to the selected landmark.

Further, the same landmark may be compared at different times (intra-landmark comparison) or one or more landmarks may be compared (inter-landmark comparison). For instance, an intra-landmark comparison can be used during a single interrogation protocol that entails multiple interrogations of the same region with reference to a particular anatomical landmark. Statistical analysis as described herein and known in the art can be performed.

Thus, the invention provides for means of assessing bone structure, i.e. the two-dimensional or three-dimensional architectural organization of the trabecular bone including, but not limited to, measurement of trabecular spacing, trabecular thickness, trabecular length and trabecular connectivity. Other examples of measurements of bone structure are provided in TABLE 1. These measurements can be used alone or enhanced with use of calibration phantoms or external standards that can allow a correction or normalization of image intensity and that can in certain embodiments also allow a correction of geometric distortions for example resulting from cone beam geometry of an x-ray beam.

The invention provides for means of assessing macro-anatomical and/or biomechanical parameters. These measurements can be used alone or enhanced with use of calibration phantoms or external standards that can allow a correction or normalization of image intensity and that can in certain embodiments also allow a correction of geometric distortions including magnification, for example resulting from cone beam geometry of an x-ray beam.

As described herein, one or more measurements of bone structure or macro-anatomical and/or biomechanical parameters can be used to select a therapy, for example the use of anabolic or antiresorptive agent in the case of bone loss or deterioration. In certain embodiments, measurements of bone structure and/or one or more macro-anatomical and/or biomechanical parameters are conducted over time to longitudinally monitor a subject's bone health longitudinally over time. Measurements can be performed at different time points T1, T2, . . . , Tn and changes in said bone structure and/or macro-anatomical and/or biomechanical parameters can be registered and used to track a patient's bone health. In either single or longitudinally measurements, a physician can be apprised of the measurements and can include a pre-determined cut-off value (e.g., when a bone structure or macro-anatomical and/or biomechanical parameter measured in a patient is more than one or two standard deviations different from a normal, healthy reference population) and use this information to select a therapy.

The data obtained and analyzed as described herein can be used to monitor a patient's response to therapy. For example, information regarding bone structural and/or macro-anatomical and/or biomechanical information in a patient receiving an anabolic or antiresorptive drug and be evaluated at different time intervals T1, T2, . . . , Tn and changes in said bone structure and/or macro-anatomical and/or biomechanical parameters can be used in order to assess therapeutic efficacy. A physician can use this information to adjust the dose of a drug administered (e.g., for treatment of osteoporosis) or to change the drug regimen.

Other techniques using x-ray information such as tomosynthesis can also be used for measuring bone structure and for selecting said therapy or monitoring said therapy.

Bone structure can be measured using a number of different technical approaches. These include but are not limited to the Hough Transform, analysis of density and size distribution of trabeculae, multidimensional classification schemes, mean pixel intensity, variance of pixel intensity, Fourier spectral analysis, fractal dimension and morphological parameters.

3.1.1.0. Hough Transform

The Hough transform (See, e.g., Hough "Machine analysis of bubble chamber pictures" in International Conference on High Energy Accelerators and Instrumentation. 1959. CERN) can be used to detect geometric objects in binary images. As an entirely new approach to assessing bone structure and/or macro-anatomical, the invention includes the use of such methods to analyze direction and length of structures in bone images. For this purpose, the region of interest (ROI) can be blurred with a Gaussian filter. The pixel values of the filtered ROI can then be subtracted from those in the original ROI, and the value 128 can be added at each pixel location. This results in an image with a mean gray value of 128, which is also used as a threshold to yield a binary image in which the trabeculae are represented by the white pixels.

Figure 7B:
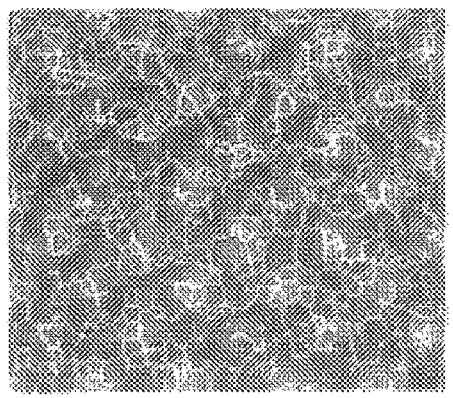
FIG. 7 shows a Hough transform (panel A) of a test image (panel B). All collinear points from the same line are transformed into sinusoidal curves that intersect in a single point (circles).
Figure 7A:
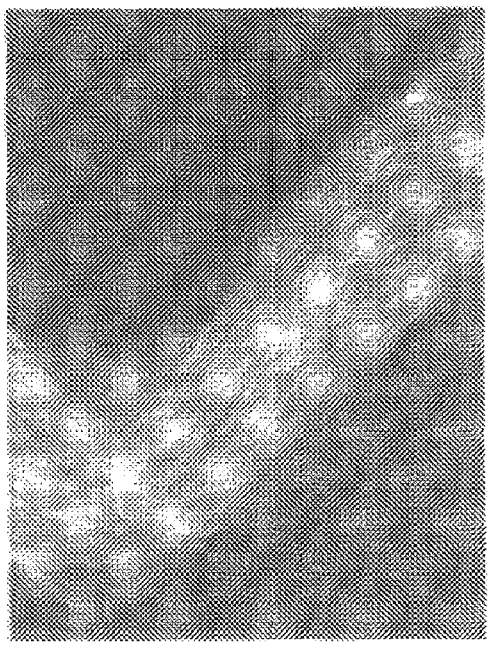
Figure 8B:
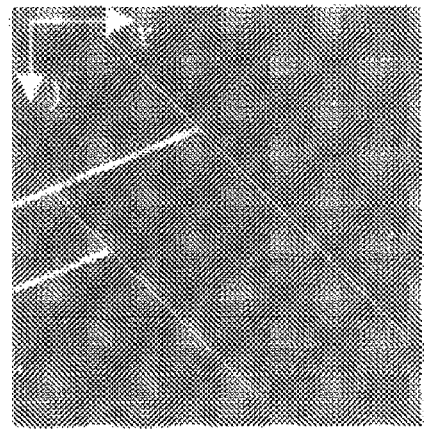
FIG. 8 shows a Hough transform (panel A) of a skeletonized trabecular bone x-ray image (panel B). The white regions in panel A indicate longer segments and predominant angles.
Figure 8A:
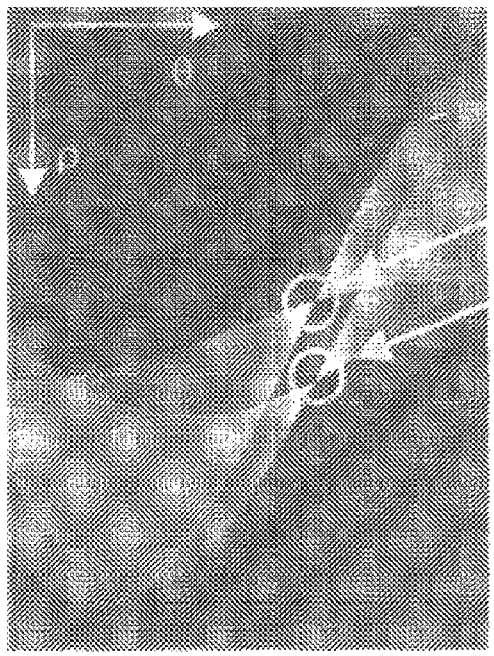

After a skeletonization step, a Hough transform with the line parameterization $\rho = x \cos \theta + y \sin \theta$ can be applied to the binary image in order to find straight line segments. Here $\rho$ is the perpendicular distance of the line from the origin and $\theta$ is the angle between the x-axis and the normal. Each point $(\hat{x}, \hat{y})$ in the original image is transformed into a sinusoidal curve $\rho = \hat{x} \cos \theta + \hat{y} \sin \theta$ in the $(\rho, \theta)$ plane of the transformed image (see FIG. 7)). Ideally, the curves from collinear points in the original image intersect in a single point in the transformed image. However, the $(\rho, \theta)$ plane can be divided into bins, where each bin counts the number of transformed curves that pass through it. This number corresponds to the number of collinear points on a line segment in the original image, and thus the length of this segment. Furthermore, the transformed image provides information on the predominant angles of the line segments in the original image (see FIG. 8).

The average length and the variance of the line segments, which are calculated for all bins with a count above a certain threshold, can be used as structural parameters for the shape of the bone trabeculae. Average length as well as the variability of the length to decrease in patients with osteoporosis. The threshold has the effect that only segments of a certain minimal length are included in the calculation. Choosing the threshold so that it provides the best discrimination between healthy and diseased individuals can be readily determined by one of skill in the art in view of the teachings herein.

The "center of mass" of the transformed image h, given as:

$$CM = \left(\sum_{(\rho,\theta)} (\rho, \theta)^T * H(\rho, \theta)\right) / \sum_{(\rho,\theta)} H(\rho, \theta),$$

in which each bin is interpreted as an element with a mass equivalent to its count, is a way to measure the predominant angles of the trabecular segments. The angle at cm is measured with respect to the alveolar rim to obtain a standardized value. More importantly, the variance of the segment angles (again measured after thresholding the bin counts) provides information on the anisotropy of the trabecular structure. Histomorphological studies of osteoporotic vertebrae have shown that the variability of trabecular orientations decreases with the disease.

3.1.2.0. Analysis of Density and Size Distribution of Trabeculae

Morphological operations such as variations of dilation and erosion and combinations thereof can also be used to detect the size of structures in gray scale or binary images. For example, a skeleton operator can be used to extract and quantify trabeculae of different sizes and directions, which results in a measure of the size distribution of trabecular structures. This skeleton operator is based on the work described in Kumasaka et al. (1997) *Dentomaxillofac Rad* 26:161-168 and works as follows:

Let a two-dimensional structuring element e be a function over the window $-m \leq i,j \leq m (m>0)$ with $E(i,j) \in \{0,1\}$. The dilation operator sets a pixel value f(x,y) in a gray scale image f to the maximum of those values within the window of size m, for which e(i,j)=1:

$$[f \oplus E](x, y) = \max_{-m \leq i,j \leq m} \{f(x+i, y+j) \mid E(i, j) = 1\}$$

The erosion operator is defined accordingly, using the minimum instead of the maximum:

$$[f \otimes E](x, y) = \min_{-m \leq i,j \leq m} \{f(x+i, y+j) \mid E(i, j) = 1\}$$

'Opening' is the operation of maximum search after minimum search:

$$f_E = (f \otimes E) \oplus E$$

Accordingly, the 'closing' operation is defined as the minimum search after maximum search:

$$f^E = (f \oplus E) \otimes E$$

If a fixed structuring element $E_1$ is given as $E_1(ij)=1$ for $-1 \leq i,j \leq 1$, the skeleton operation is then defined as $$S_{Trabeculae}(f) = (f \otimes E_2) - [(f \otimes E_2)_{E_1}] \quad (1)$$

$E_2$ is another structuring element that is of circular shape and can be varied in size, and therefore renders the skeleton operator sensitive to the size of the structures in the image. The erosion of f with $E_2$ erases the structures that are smaller than $E_2$ and extracts those trabeculae that are at least equal in size. Those structures that are exactly equal in size is reduced to a width of one pixel. The opening step with $E_1$ causes all structures that are one pixel wide to disappear (second term in (1)). After subtraction of this term from the first one, only those trabecular structures that exactly match the size of $E_2$ remain. Finally, the image is thresholded with a level of 1. The effect of this operator is illustrated in FIG. 9.

Figure 9:
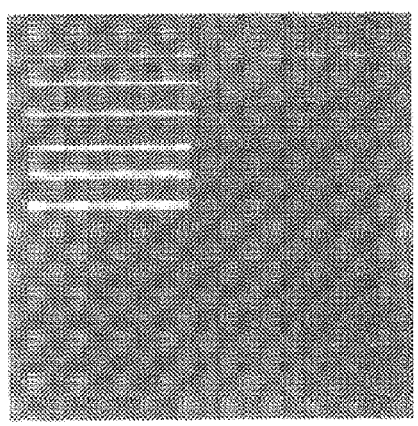
FIG. 9 shows the effect of varying size of structuring element $E_2$; calibration phantom image with lines of varying width (1, 3, 5, 7, 9, 11, 13 pix) (top left); skeleton operation performed using $E_2$ with a diameter of 3 pix (top right), 7 pix (bottom left), and 11 pix (bottom right), respectively.
Figure 10A:
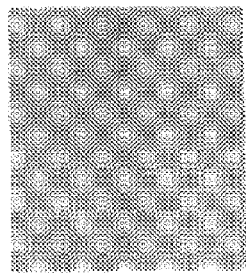
FIG. 10 shows the effect of varying size of structuring element $E_2$; gray scale image of trabecular bone (top left, panel A); skeleton operation performed using $E_2$ with a diameter of 3 pix (top right, panel B); 7 pix (bottom left, panel C) and 11 pix (bottom right, panel D), respectively.
Figure 10B:
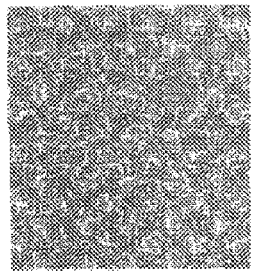
Figure 10C:
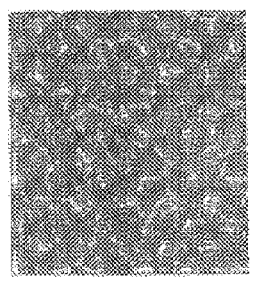
Figure 10D:
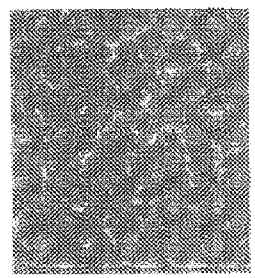

FIG. 10 demonstrates the use of the skeleton operator with the same structural element diameters as in FIG. 9 on a gray scale region of interest from a dental x-ray containing trabecular bone. The number of bright pixels in the binary images resulting from each skeleton operation corresponds to the portion of trabeculae of the particular size in the original image. If the percentage of the bright pixels with respect to the total number of pixels in each skeletonized image is plotted against the diameter of $E_2$, the "center of mass" of the curve, i.e. the predominant structure size, can be used as an index to discriminate between osteoporotic and healthy bone.

Furthermore, the skeleton operator is preferably optimized and extended to detect structures that are oriented only in a specific direction. This can be achieved by adding erosion operations to the skeleton operator with structural elements in which, for example, only the diagonal pixels are set to 1.

This can be used to calculate an anisotropy index, similar to the one derived from the Hough transform. Both anisotropy indices are tested with respect to their potential to distinguish healthy from osteoporotic bone.

In a similar manner the sizes of the marrow spaces can be examined. The skeleton operator is then defined as $$S_{Marrow}(f) = (f \oplus E_2) - [(f \oplus E_2)^{E_1}]$$

In addition, the watershed segmentation can be applied to background subtracted gray level structures on x-ray images to characterize the homogeneity of trabecular structures. This process takes into account the gray level contrast between structures to define marrow spaces. The watershed segmentation, when applied to background subtracted bone x-ray images, defines regions with lower gray levels (or basins) surrounded by higher gray level structures (or ridges), as marrow space, in accordance to the spatial extend and gray levels of ridges. Therefore, the size and orientation of marrow space segments defined by this procedure can be related to the spacing, relative density and orientation of adjacent trabecular structures. The segments of marrow space generated using the watershed segmentation can be measured for their area, eccentricity, orientation, and the average gray level on the x-ray image within the segment. The statistics (for example mean, standard deviation, minimum, maximum, and mode) for each of the segment characteristics can be measured. These statistics can be selected to reflect the homogeneity of marrow space and trabecular structures, and can be used to detect presence of abnormal distribution of marrow space and trabecular structures.

3.1.3.0. Multidimensional Classification Schemes

In certain embodiments, it is preferred to use multiple indices to measure bone structure and/or macro-anatomical parameters. Thus, novel approaches that integrate one or more suitable indices can be employed. The indices can be optimized and incorporated into a multi-dimensional classification scheme, for example using a nearest neighbor classification. Cover et al. (1967) *IEEE Trans Inform Theory* 13(1):21-7. (See, Example 3).

Table 1 provides examples of different analyses and anatomical/physiological correlates of the parameters that can be measured.

TABLE 1

| Analysis | Anatomical/Physiological Correlates |
|---|---|
| Hough transform | length and direction of trabeculae; anisotropy |
| Morphological operators | thickness and direction of trabeculae; anisotropy; thickness and length of marrow spaces |
| Mean pixel intensity | bone mineral density |
| Variance of pixel intensity | complexity of trabecular structure |
| Fourier spectral analysis | complexity of trabecular structure |
| Fractal dimension | complexity of trabecular structure |
| Morphological parameters | length, size of trabeculae; complexity of trabecular structure; length, size of marrow spaces; complexity of marrow space |

3.1.3.1 Mean Pixel Intensity

Mean pixel intensity is a general parameter for the bone mineral density. The degree to which x-rays passing through bone tissue are absorbed depends on the bone's mineral content. Bone with a higher mineral density absorbs a larger portion of x-rays, and therefore appears brighter on an x-ray image.

The mean pixel intensity $\overline{f(x,y)}$ in the ROI is calibrated against an aluminum calibration wedge that is included in the image. The log of the average pixel intensity for each thickness level of the calibration wedge is plotted against the thickness, which allows $\overline{f(x,y)}$ to be converted into a standardized aluminum thickness equivalent, which is used as the value for this parameter. The automatic recognition of the different thickness levels of the calibration wedge are made possible by different geometric patterns scribed into the wedge which are shown in the x-ray image and can be localized automatically.

3.1.3.2. Variance of Pixel Intensity

The variance of the pixel gray values in the ROI, var f(x,y), describes the variability of the pixel intensities and can therefore be a measure of the degree of trabeculation. A loss of trabecular bone is predicted to be reflected by a decreased var f(x,y). Southard & Southard (1992) *Oral Surg Oral Med Oral Pathol* 74:111-117.

3.1.3.3. Fourier Spectral Analysis

The spatial frequency spectrum of a texture provides information about its coarseness. Fine textural structures and edges in an image correspond to high frequencies in the frequency domain, while coarse textures are represented by lower frequencies. Applied to x-ray images of trabecular bone, this means that a region with coarse or little trabeculation should exhibit a Fourier spectral energy concentration at low spatial frequencies, whereas a region of fine trabecular structure should show a spectral energy concentration at high frequencies.

Typically, the 2-dimensional Fourier coefficients for the selected ROI. These 2-dimensional coefficients are used to determine a 1-dimensional power spectrum F(u) by averaging all coefficients over circles with radii that correspond to the discrete spatial frequencies u. The mean transform coefficient absolute value $\overline{|F(u)|}$ and the mean spatial first moment $$M_1 = \frac{\sum_{u=2}^{N} |F(u)| \cdot u}{N-1}$$

of the absolute coefficients are determined after exclusion of the first ("DC") coefficient. $M_1$ provides a measure for which frequencies contribute most to the energy of the spectrum, similar to the "center of mass" of a geometric object.

3.1.3.4. Fractal Dimension

Figure 11:
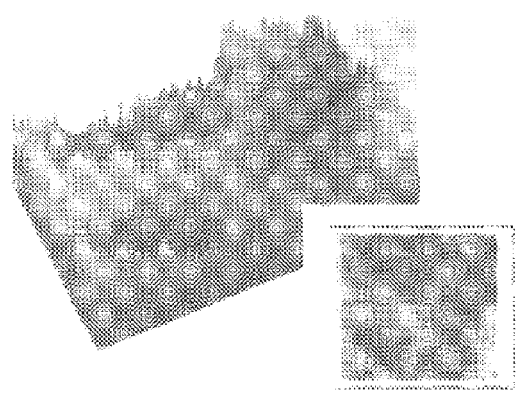
FIG. 11 shows gray value surface plot of an anatomical region of interest from a dental x-ray (inset) used for fractal analysis.

A different approach to analyze the texture in an image is by fractal analysis. Fractals are objects that exhibit certain statistical self-similar or self-affine properties, so that a portion of the object, scaled to its original size, has for example the same surface area (3-d) or the same perimeter (2-d) as the original object. In the context of fractal analysis, the gray values in a particular texture can be interpreted as an altitude, and the resulting 3-dimensional surface is analyzed (FIG. 11).

Fractal dimension (fd) is the rate at which the perimeter or surface area of an object increases as the measurement scale is reduced. Russ "The Image Processing Handbook," Third edition ed. 1999, Boca Raton: CRC press. It is a measure for the complexity of a boundary or surface and corresponds to the intuitive notion of an object's roughness. Without being bound by one theory, it is postulated that osteoporotic trabecular bone, in which trabeculae become thinner and lose their continuity, and therefore complexity is increased, should have a higher fractal dimension than healthy bone.

The results from the several ways in which FD can be measured are not comparable. Thus, various methods can be tested to determine which one (or combination) provides the best discrimination between normal and osteoporotic subjects.

The first method is applied in the frequency domain after calculation of the ROI's 2-D power spectrum using a fast Fourier transform (FFT). From the 2-D Fourier coefficients the 1-D power spectrum is produced as described above for the Fourier analysis. When this 1-D power spectrum is plotted as the logarithm of the power versus the logarithm of the frequency, it must have a negative slope of magnitude b with $1 < b < 3$ according to fractal theory. The FD value is then calculated as $FD_1 = 3.5 - b/2$.

Another approach, the Minkowski method, measures the difference (summed over the ROI) between an upper and lower envelope fitted to the surface as a function of the size of the neighborhood used. Peleg et al. (1984) *Anal Mach* Intell 6(4):518-523. If $\delta$ ($\delta=1, 2, 3, \ldots$) is the distance between the envelopes and the surface, then the upper envelope $u_\delta$ and the lower envelope $l_\delta$ are given by $$u_0(i,j) = l_0(i,j) = f(i,j)$$
$$u_{\delta+1}(i,j) = \max\{u_\delta(i,j)+1, \max_{\|(m,n)-(i,j)\| \le 1} \{u_\delta(m,n)\}\}$$
$$l_{\delta+1}(i,j) = \min\{l_\delta(i,j)-1, \min_{\|(m,n)-(i,j)\| \le 1} \{l_\delta(m,n)\}\}$$

where f(i,j) is the gray value of pixel (i,j) in the ROI. The log of the area $A(\delta)$, plotted against $\log(\delta)$, yields a line with a negative slope of magnitude b'. The fractal dimension is then given by $FD_2 = 2 - b'$. The area is calculated as $$A(\delta) = \frac{v_\delta - v_{\delta-1}}{2}$$

with $$v_\delta = \sum_{(i,j)\in ROI} (u_\delta(i,j) - l_\delta(i,j)).$$

3.1.3.5. Morphological Parameters

While the previous features and parameters provide rather general information on trabecular bone structure, the following examples describe more detailed aspects.

The gray scale region of interest is first binarized. As described in White et al. (1999) Oral Surg Oral Med Oral Patholo Oral Radiol Endod 88:628-635, this can be achieved in the following way: The ROI is blurred by means of a Gaussian filter. The blurred ROI is then subtracted from the original ROI, and the value 128 is added at each pixel location. This results in an image with a mean gray value of 128, which is also used as a threshold, resulting in an image, in which trabeculae are white and marrow space is black.

From this binary image, the total number of white pixels represents the trabecular area, which is calculated as a percentage of the total ROI area. The number of pixels on the outer trabecular border measures the peripheral length of the trabeculae. The same parameters can be measured for the marrow space by counting the black pixels.

After skeletonization of the binary image, the total length of the trabeculae is determined by the total number white pixels. Furthermore, counts of the terminal points and of the branch points are expressed as a proportion of trabecular length. An estimate of the average length of the trabeculae is calculated as the ratio of total trabecular length and the sum of terminal points and branch points.

3.1.3.5. Markov Random Fields

In certain embodiments, Markov random fields can be used as models for osteoporosis detection from radiographic images and for fracture risk prediction. As noted herein, osteoporosis is typically manifested in radiographic images by structural changes that can be used for computer-aided detection and characterization. Thus, the detection and/or characterization of osteoporosis from radiographic images relies on the measurement and analysis of a feature or set of features relating to the density of the bone or trabecular structures present in an image.

Figure 19:
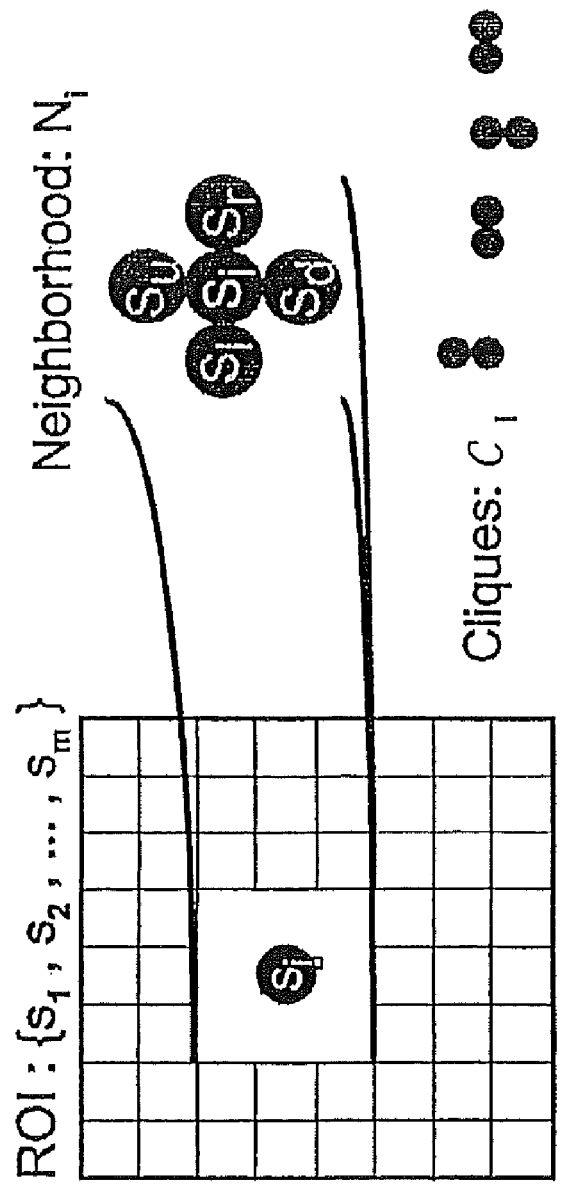
FIG. 19 depicts a Markov random field analysis by modeling particular joint feature distributions as they are estimated at each image element or image neighborhood.
Figure 20:
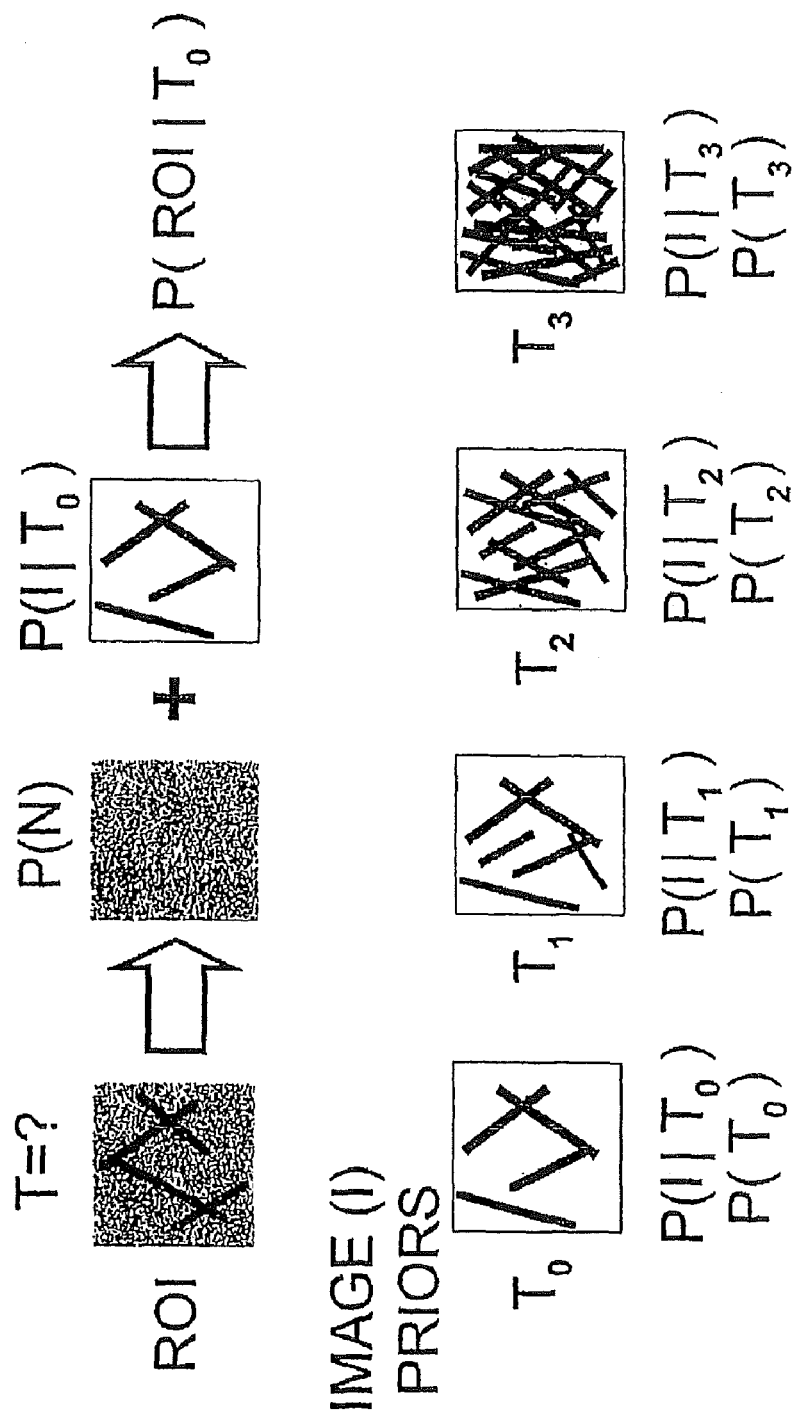
FIG. 20 depicts an exemplary model definition for trabecular pattern density characterization in a region of interest (ROI) with a noise model P(N) and characteristic structure pattern given a density level P(I|Ti).

Markov random fields can be used to analyze and detect structure density changes by either modeling particular joint feature distributions ({F1, F2, ..., Fn}) as they are estimated at each image element or image neighborhood (FIG. 19), or by modeling the actual radiographic manifestation of particular structural definitions (e.g. trabeculae) (FIG. 20).

In the first case of estimation at each image element or image neighborhood, the Markov random field framework is used for a context-based feature analysis/discrimination approach which takes into account local relationships between the features and effectively compensating for space-varying processes (e.g. variable soft tissue or missing or incomplete data due to boundaries) that can affect the relative values of the features taken into account. (Buntine (1994) "Operations for learning with graphical models," *J. Artificial Intelligence Res. December:* 159-225).

This approach can also be used for predicting most likely fracture paths based on the analysis of trabecular structure nodes and their related feature sets by defining the most likely chains of joint feature sets. The analysis framework can be a Likehood Ratio approach:

$$\lambda = \frac{P(ROI \mid \text{Normal})}{P(ROI \mid \text{Abnormal})},$$

where P(ROI|.) is given by the corresponding Markov random field model.

Another analysis approach is through the implementation and training of Bayesian networks, for example as described in Heckerman D (1996) "A tutorial on learning with Bayesian networks," *Microsoft Research Technical Report*, MSR-TR-95-06. based on available test case data.

Figure 21:
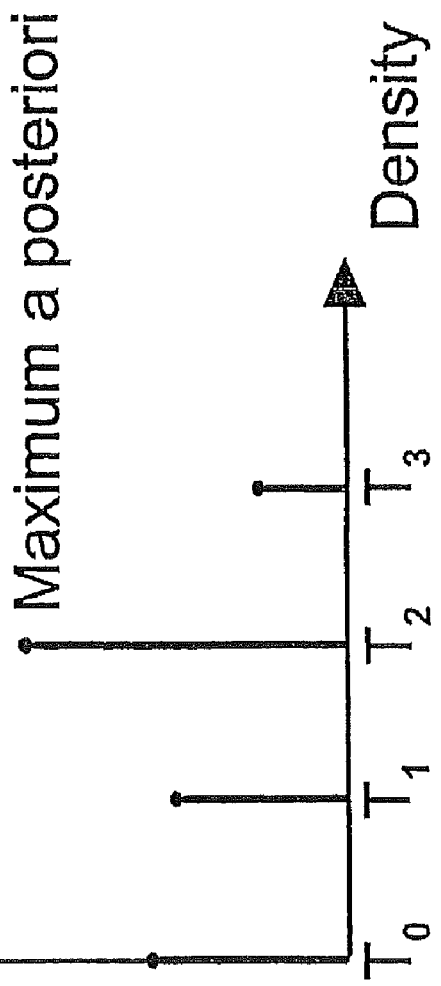
FIG. 21 depicts exemplary Bayes' Rule analysis.

Markov random fields can also be used to model the manifestations of the structures in an image in probabilistic terms. (Geman et al. (1984) "Stochastic relaxation, Gibbs distributions, and the Bayesian restoration of images," *IEEE Transactions on Pattern Analysis and Machine Intelligence* 6:721-741; Besag (1986) "On the statistical analysis of dirty pictures," *Journal of the Royal Statistical Society*, 48(3):259-302). As depicted in FIG. 20, each of the image components (noise and characteristic structure) has associated probabilistic models, P(N) and P(I|T) respectively, that describe the spatial distribution of the gray-level intensity. For example, a common assumption for the noise component in digital/digitized radiographs is to consider Normal or Poisson distributed pixels. The nomenclature for the distribution of the characteristic texture P(I|T) is such as to reflect that the corresponding probability distribution of the region I is conditional (expressed by the symbol |) on the characteristic structure present T. The analysis tools for such a probabilistic framework are provided by the laws of probability and specifically Bayes' Rule shown in FIG. 21. Bayes' rule can be described as the rule according to which our knowledge about the presence of a given characteristic structure in an ROI is updated (a-posteriori information represented by the probability distribution P(T|ROI)), based on experience of how often (or likely) each characteristic structure is present (a priori information represented by the probability distribution P(T)) and knowledge of how the sources of noise and variability change the manifestation of the corresponding characteristic structure (knowledge of the likelihood, thus also called the likelihood function P(ROI|T), of the ROI image given the possible characteristic structures and overlapping degrading components). FIG. 21 illustrates that simply selecting the structure with the maximum a-posteriori information can be used as a decision criterion.

To define the likelihood function P(ROI|T), Markov random field modeling may be employed. Markov random fields are specific multidimensional random processes that satisfy what is known as the Markov property. The Markov property simply states that in a random series of events, each event can be predicted and depends only on a limited set of events. This property is convenient and intuitive for the modeling and analysis of structures in images. It basically states that if the distribution of pixels in an ROI can be modeled as having the Markov property, then in order to determine if a pixel belongs to a given structure, only a limited number of neighboring pixels are necessary.

Random fields having the Markov property confer the additional benefit of having an associated Gibbs probability distribution given by the following equation:

$$P(ROI = s_1, s_2, \ldots, s_m) = \frac{e^{-U(s_1, s_2, \ldots)}}{z}$$

Where the function:

$$U(s_1, s_2, \ldots) = \Sigma V(s_i) + \Sigma V(s_i, s_j) + \Sigma V(s_i, s_j, s_k) + \ldots$$

depends on functions V (called potentials) of local neighboring elements called cliques:

$$\{s_i\}, \{s_i, s_j\}, \{s_i, s_j, s_k\}, \ldots \in C$$

The significance of cliques is that they are the fundamental elements that can be used to reflect specific spatial distribution properties of a structure of interest, such as for example vertical, horizontal and diagonal geometries. Furthermore, the Markov property is manifested very conveniently as each image pixel can be expressed in terms of the cliques in a local neighborhood:

$$P(s_i \mid s_k, s_k \in N_i) = \frac{e^{-V_{N_i}}}{\sum_{s_c} e^{-V_{N_i}(s_c)}}$$

The model parameterization for the families of images characteristic of a particular structural density grade and definition of a priori information can be done either by estimation from available patient data thus defining empirical priors or by implementing physical and stochastic models that are based on the image generation process.

3.1.4.0. Overlapping Windows Processing

Figure 16:
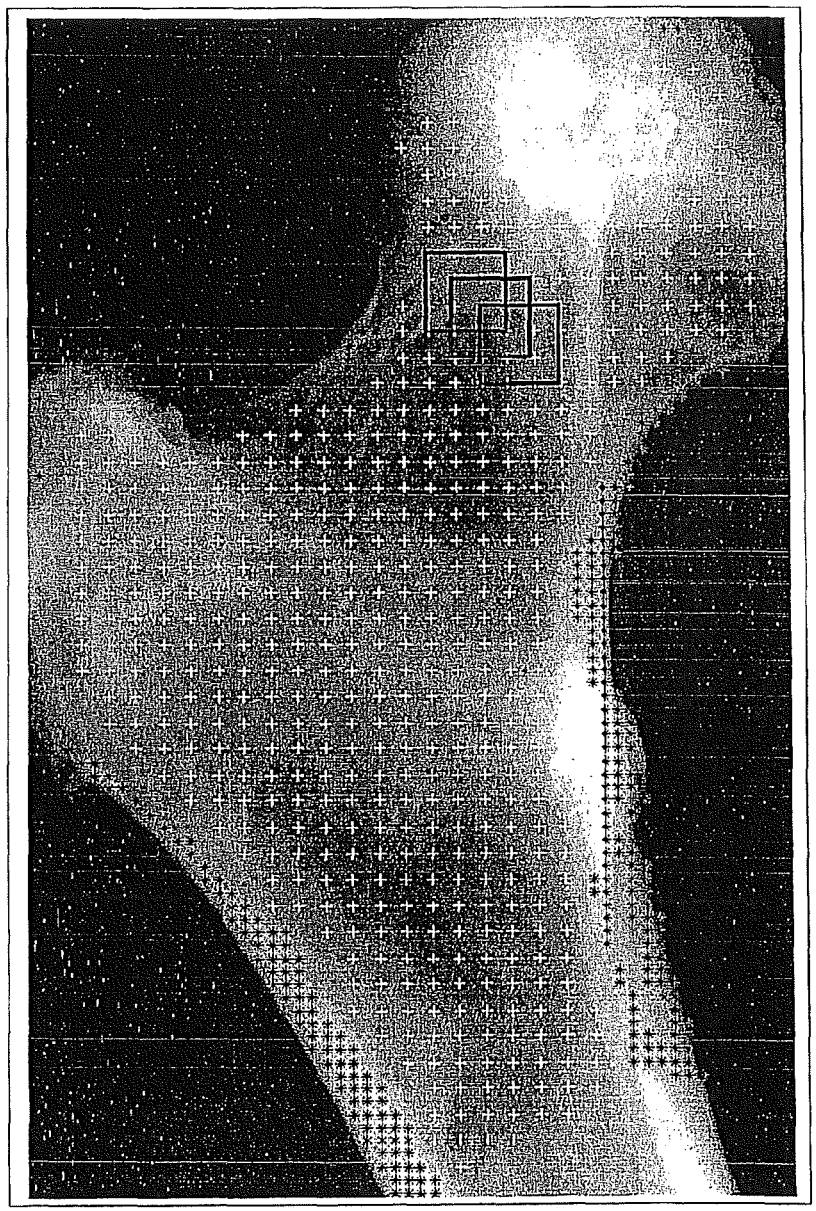
FIG. 16 depicts an example of a regular interval sampling field for microarchitecture (+) and a higher density sampling field for macro-anatomical features (*) on a femur radiograph. White rectangles are examples of overlapping window positioning.

Furthermore, two or more overlapping ROIs can also be defined and used to analyze any given image. In other words, bone density, microarchitecture, macro-anatomic and/or biomechanical (e.g. derived using finite element modeling) analyses can be applied within a region of predefined size and shape and position. This region of interest may also be referred to as a "window." Processing can be applied repeatedly within the window at different positions of the image. For example, a field of sampling points may be generated and the analysis performed at these points (FIG. 16). The results of the analyses for each parameter can be stored in a matrix space, e.g., where their position corresponds to the position of the sampling point where the analysis occurred, thereby forming a map of the spatial distribution of the parameter (a parameter map). The sampling field can have regular intervals or irregular intervals with varying density across the image.

The amount of overlap between the windows can be determined, for example, using the interval or density of the sampling points (and resolution of the parameter maps). Thus, the density of sampling points is set higher in regions where higher resolution is desired and set lower where moderate resolution is sufficient, in order to improve processing efficiency. The size and shape of the window would determine the local specificity of the parameter. Window size is preferably set such that it encloses most of the structure being measured. Oversized windows are generally avoided to help ensure that local specificity is not lost.

The shape of the window can be varied to have the same orientation and/or geometry of the local structure being measured to minimize the amount of structure clipping and to maximize local specificity. Thus, both 2D and/or 3D windows may be used, depending on the nature of the image and data to be acquired.

In another embodiment, bone density, microarchitecture, macro-anatomic and/or biomechanical (e.g. derived using finite element modeling) analyses can be applied within a region of predefined size and shape and position. The region is generally selected to include most or all of the anatomic region under investigation and, preferably, the parameters can be assessed on a pixel-by-pixel basis (e.g., in the case of 2D or 3D images) or a voxel-by-voxel basis in the case of cross-sectional or volumetric images (e.g., 3D images obtained using MR and/or CT). Alternatively, the analysis can be applied to clusters of pixels or voxels wherein the size of the clusters is typically selected to represent a compromise between spatial resolution and processing speed. Each type of analysis may yield a parameter map.

Parameter maps can be based on measurement of one or more parameters in the image or window; however, parameter maps can also be derived using statistical methods. In one embodiment, such statistical comparisons can include comparison of data to a reference population, e.g. using a z-score or a T-score. Thus, parameter maps can include a display of z-scores or T-scores.

3.1.4.1. Analysis and Selection of Parameter Maps

The parameter maps can represent individual parameters or combinations of parameters such as density, microarchitecture macro-anatomical parameters or biomechanical parameters, for example derived using finite element modeling, are useful in identifying regions or patches that have similar characteristics. For instance, depending on their position, shape, size, orientation, and extent particular regions or patches that exhibit similar characteristics (e.g., values at high or low ranges of the data set) typically represent regions of bone with different properties, for example areas of stronger or weaker areas. Therefore, parameter maps can be used to generate virtual fracture lines that aid in predicting areas of the bone that may be subject to an increased risk of fracture. One or more parameter maps can be selected by statistical analysis of results from in vitro mechanical loading tests or by other means (e.g. from cross-sectional or longitudinal studies in osteoporosis subjects, in particular those developing fractures). Selection can be based, for example, on patch location, shape, size, orientation and extent that best correlates with location of actual fracture lines and/or for having parameter values that are best correlated with fracture risk, the incidence of osteoporotic fractures or fracture loads.

3.1.4.2. Fracture Path Prediction

When there are multiple parameter maps that correlate well with fracture line, a multivariate regression model can be fitted to generate a composite parameter map derived from 2D or 3D data sets, e.g. x-rays, digital tomosynthesis, CT and MRI, using the techniques described herein and/or statistical methods known to those of skill in the art. A parameter map can be used to predict the overall bone strength or fracture risk or fracture load by analyzing the predicted fracture paths. A predicted fracture path is defined here as the hypothetical path where fracture would most likely to occur, if sufficient forces are applied in one or more particular directions.

Figure 17:
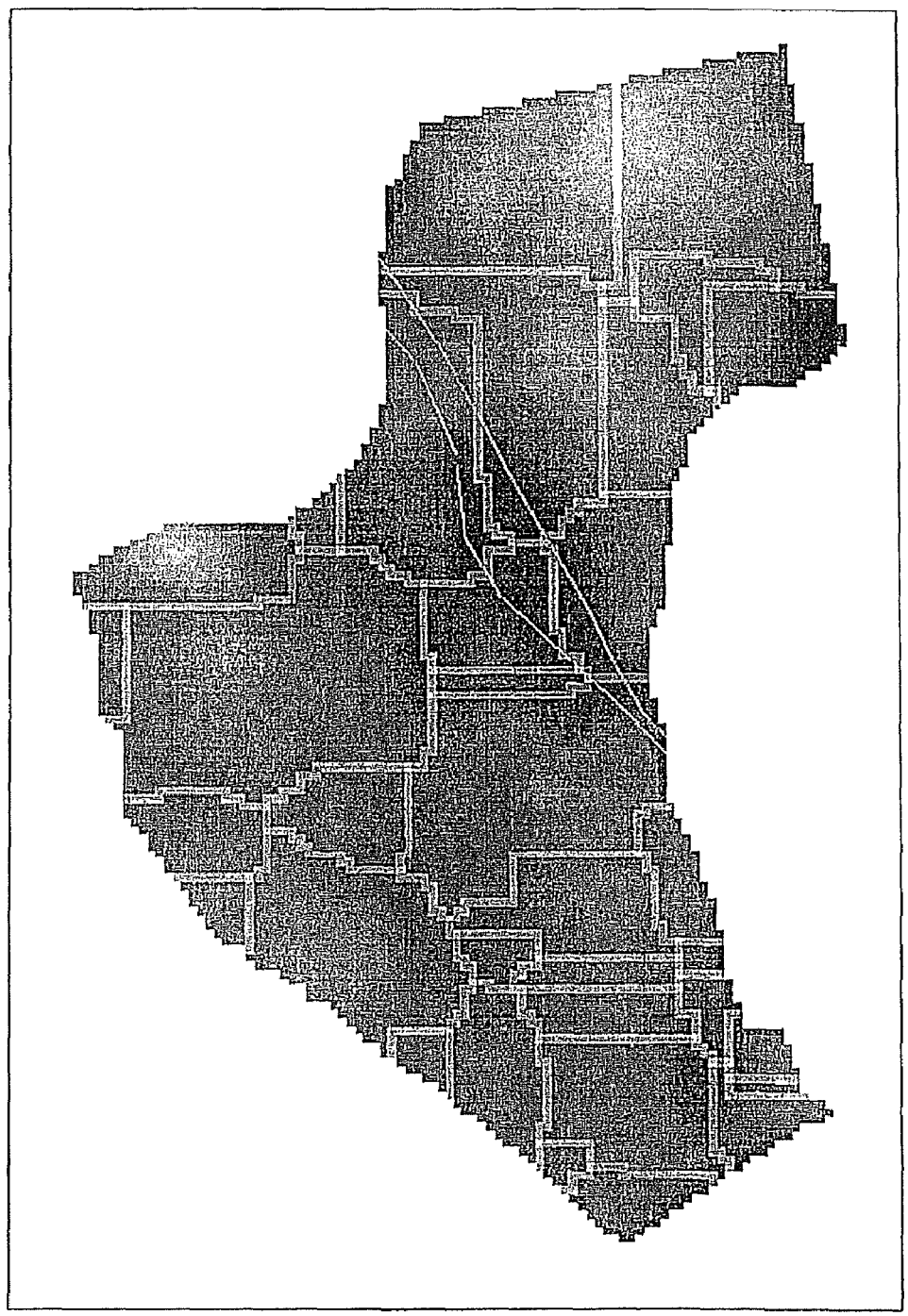
FIG. 17 depicts watershed segmentation boundaries superimposed on a parameter map. The two white lines are the actual fracture paths resulted from an in-vitro mechanical loading test.

In certain embodiments, a watershed segmentation can be applied to the selected or composite parameter map. Watershed segmentation can be applied to 2D images as well as to 3D (cross-sectional or volumetric data obtained, for example, from CT or MR). The boundaries of watershed segmentation generally form along the ridges on the parameter map, i.e., along the peak values. For a parameter that is positively correlated to bone strength or fracture load, i.e., higher values correspond to stronger bones, the inverse value of the parameter is used to generate the watershed boundaries so that the boundaries would form along valleys (local minimum) of parameter maps. The nodes of watershed boundaries can be identified and segmented to separate the watershed boundaries into segments (FIG. 17). Each of these segments can be assigned a strength value or fracture load value which is a composite value of one or more parameter maps underlying the segment. The length, orientation, and position of segments can be used as normalizing factors for the strength values.

The nodes and segments of the watershed boundaries may be labeled, traced, measured, and recorded in a form of data structure, for example, a graphical structure. The strength values and interconnect relationships are also stored for each segment. To identify the most likely fracture paths, a search strategy, for example, the depth-first search (Russell S., Norvig, P., Artificial Intelligence: A modern approach. 1995, NJ: Prentice Hall. pp. 77), is propagated through the data structure to determine the paths of least resistance from one surface of the bone to another opposite surface restricted by a predefined solid angle. Alternatively, an artificial neural network can be trained to predict fracture paths given the parameter maps as inputs.

3.1.4.3. Fracture Risk Prediction

Having predicted one or more fracture paths, additional processing may be performed, typically with a new processing grid that has high concentration of nodes along the predicted fracture paths with a different window size and/or shape. Macro-anatomical parameters such as cortical thickness can be evaluated (in two or three dimensional images) with higher resolution at the exits of fracture paths. Parameters that are the best predictors of fracture risk can be evaluated along the predicted fracture paths. These parameters, including density, microarchitecture, macro-anatomical measurements and biomechanical parameters, are selected by statistical analysis of results from in-vitro mechanical loading test or by other means, e.g. using cross-sectional or longitudinal studies in osteoporosis subjects, in particular those developing fractures, for being highly correlated to the magnitude of one or more mechanical properties of bone, for example in one or more particular loading force directions, or for being highly correlated with fracture risk, incidence of new fractures or fracture loads. The mechanical properties include but are not limited to yielding load, stiffness, and Young's modulus.

Figure 18:
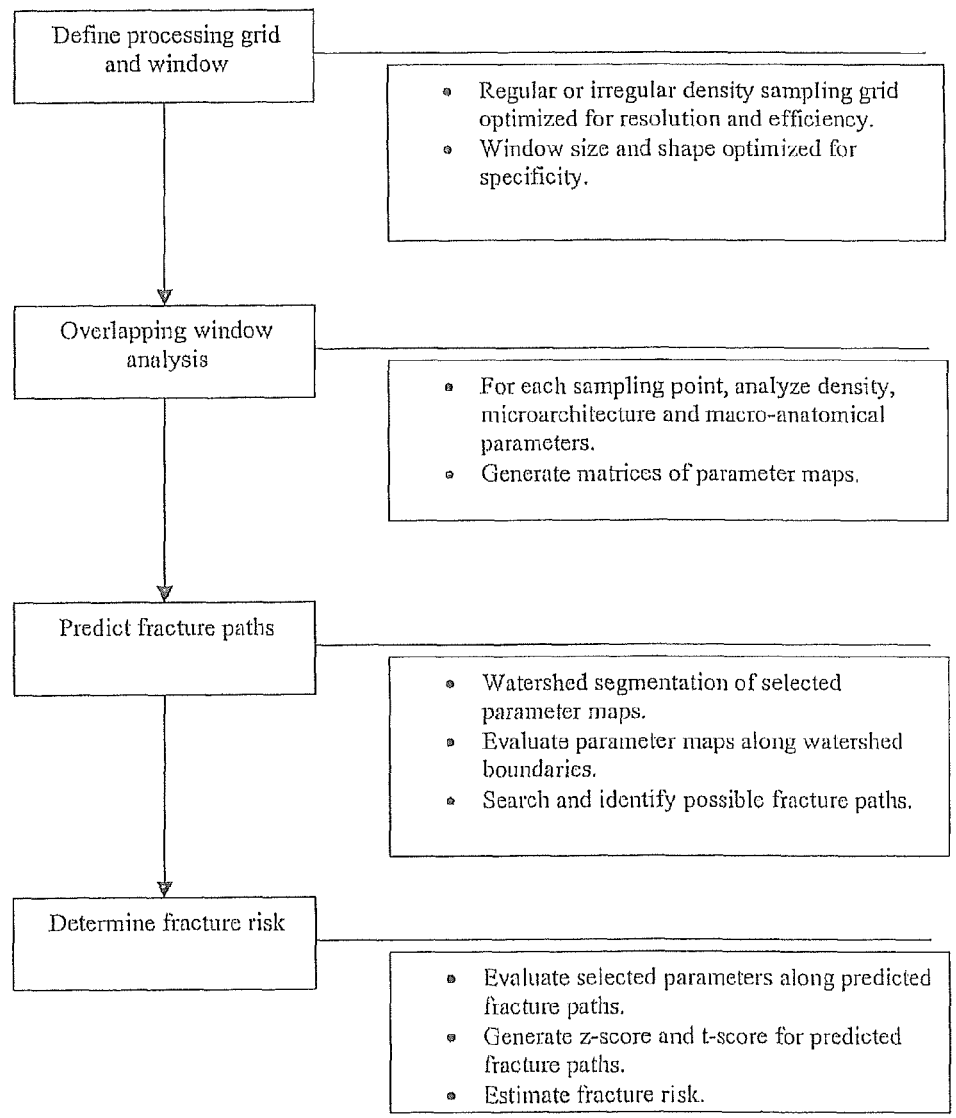
FIG. 18 is a flowchart depicting an exemplary process to determine fracture risk using overlapping window processing and fracture paths prediction.

The values of parameters along the predicted fracture paths may be compared against the statistical distribution of the population. The z-score and T-score of each parameter relates to the risk of fracture occurring in a particular predicted fracture path. Thus, a fracture risk score can be assigned to that fracture path. The predicted fracture paths can also be associated with the clinical definition of common fracture types. The overall fracture risk can then be evaluated by weighing fracture risk score of each predicted fracture path with the probability of a particular type of fracture occurring. FIG. 18 depicts an exemplary summary of this process.

3.1.5.0. Biomechanical Assessment

The features and values extracted from the processing of density, micro-architecture, macro-anatomical parameters can be used as the inputs for biomechanical modeling, for instance modeling using finite element analysis. Finite element modeling (FEM) can be used as a surrogate for the physical mechanical properties of bone or composite of bone and implants. Briefly, FEM involves the division of a structure or object into discrete shaped elements, where the mechanical behavior of each element can be described by precise mathematical equations. Structural finite element analysis (FEA), a particular subset of FEM, is the calculation of the mechanical behavior (stress and strain) at any point within the structure under specific loading conditions. The foundation of every finite element model is the two-dimensional or three-dimensional data of the object or structure Examples of microarchitecture and micro-anatomical features that can be used as input mesh for finite element analysis include but are not limited to the actual and derivation of image or data structures of trabecular structures, image or data structures of cortical bone, image, data structures of trabecular skeleton or parameter maps derived from overlapping window processing. As described herein, the input features can be obtained from 2D and/or 3D images. The application of simulated force can be in one or more directions, and is typically associated with the actual force components that would occur in a fracture incident. The finite element analysis provides an estimate of load and direction of fracture for each fracture incident scenario. Fracture risk is estimated by weighing the fracture loads with the probability of each fracture scenario occurring. Further, the fracture paths estimated by finite element analysis can be used as inputs to the analysis of density, micro-architecture, macro-anatomical features. For example, density, micro-architecture, macro-anatomical features can be measured in areas of fracture paths predicted by finite element modeling. Conversely, finite element analysis can be combined with additional image and clinical data to determine fracture risk by predicting if the bone would fracture, given the force components that would occur in a fracture incident.

Bone fracture risk can be evaluated using one or a composite of more than one dependent or independent results of analysis or statistical methods. An example of this combination is the weighted average score of density, micro-architecture, macro-anatomical, finite element analysis and clinical risks factors such as weight, height, history of fracture, family history of fracture, and the like.

Finite element modeling can be applied to all of the bony structures included in an image. Preferably, however, finite element modeling is typically applied in selected subregions. In certain embodiments, finite element modeling is applied in areas coinciding with or bordering with the predicted fracture path, for example based on micro-structural or macro-anatomical measurements. By combining biomechanical assessment of bone properties with density, micro-architectural and macro-anatomical assessment, the prediction of fracture risk and/or the correlation with fracture load can be improved. Finally, regional assessment of biomechanical properties can also improve the accuracy of the fracture path prediction.

Biomechanical assessment can also include more traditional approaches estimating levers and forces at the macro-anatomical level, e.g. measurement of moments, shear and compressive forces based on macro-geometric parameters of the bone and anticipated loads or stresses. These more traditional approaches can be combined with finite element modeling, measurements of density, bone structure, and macroanatomical parameters, e.g. cortical thickness, thereby improving assessment of bone strength and fracture risk and improving the correlation with fracture loads and, ultimately, incident new fractures.

As will be appreciated by those of skill in the art, the macroanatomical parameters that are measured can change depending on the region of interest to be measured. For example, when studying a portion of the spine, the user can combine bone structure measurements with macroanatomical measurements and/or FEA and/or other biomechanical measurements and/or bone mineral density. The actual macroanatomical measurements that are used in the spine can be, for example, the inner pedicle distance, the outer pedicle distance, the vertebral height (either anterior, central, posterior, left, right, or a combination thereof), the vertebral anterior-posterior diameter (taken either in the superior, middle, inferior, or another location), the vertebral right to left diameter (taken in either the superior, middle, inferior or another location), the vertebral diameter (taken in an oblique plane), the vertebral diagonal (using, e.g., internal cortex or external cortex), the thickness of the superior endplate (taken, e.g., anteriorly, centrally, posteriorly, from the left, from the right, or a combination thereof), or using the thickness of the inferior endplate (again taken, e.g., anteriorly, posteriorly, from the left, from the right, or a combination thereof).

Similarly, when studying the knee and tibia, the user can combine bone structure measurements with macroanatomical measurements and/or FEA and/or other biomechanical measurements and/or bone mineral density. However, as will be appreciated by those of skill in the art, the bone structures used for measurements when studying the knee and tibia region change due to changes in anatomy. Thus, in studying the knee and tibia region, suitable measurements are taken from, for example, the anterior-posterior diameter of the bone using the inner or outer cortex, or a combination thereof, the medial-lateral diameter of the bone using the inner or outer cortex, or a combination thereof, the cortical thickness in various locations, the standard deviation of cortical thickness, the subchondral bone thickness in various locations, and/or a combination thereof.

Cases may arise where the macroanatomical measurements are used to normalize bone structure or bone density measurements. For example, in the tibia, bone structure and/or bone density measurements could be altered if the patient has a tibia that is thick in the anterior-posterior dimension (e.g., thicker than average). The macroanatomical measurements are then used to normalize the tibial measurement by, for example, forming a ratio between the thick tibial measurement in the anterior-posterior direction and another measurement.

3.2.0.0. Soft Tissue

Variations in soft tissue thickness can be significant in analyzing and evaluating bone density and bone structure, macro-anatomical parameters and biomechanical parameters, e.g. those derived using finite element modeling, in x-rays. Accordingly, the invention also includes methods and devices for correcting for soft tissue in assessment of bone structure or dense tissue, particularly for diagnosing and/or predicting osteoporosis or other bone conditions.

In certain embodiments, the x-ray image is a dental x-ray image and such correction methods involve (a) interrogating at least a portion of a subject's mandible and/or maxilla with an x-ray detector; (b) producing an x-ray image of the interrogated mandible and/or maxilla; (c) obtaining data from the x-ray image regarding bone density or bone structure; (d) interrogating the surrounding soft tissue to determine soft tissue thickness; and (e) correcting the data obtained from the x-ray image by correcting for soft tissue thickness. Such study groups include: non-osteoporotic premenopausal, non-osteoporotic postmenopausal, osteoporotic postmenopausal patients. It will be apparent, although exemplified with respect to dental x-rays, that many of the methods described herein can be applied to other x-ray images, e.g. hip or spine x-ray images.

Soft tissue thickness measured in a subject can also be compared to reference soft tissue thickness obtained from a control population (e.g. age-, sex-, race-, or weight-matched normal subjects). Reference soft tissue thickness can be generated by measuring soft tissue thickness in healthy subjects with normal vascular, cardiac, hepatic, or renal function and no other underlying medical condition. Reference soft tissue thickness can be expressed as but are not limited to, mean and standard deviation or standard error. Reference soft tissue thickness can be obtained independently for patients 15-20, 20-30, 30-40, 40-50, 50-60, 60-70, 70-80, and 80 and more years of age and are preferably obtained separately for men and women and for race (e.g. Asian, African, Caucasian, and Hispanic subjects). Additionally, reference soft tissue thickness can be obtained for different subject weights within each age, sex, and racial subgroup.

Individual patients can be compared to reference soft tissue thickness. If patient's soft tissue thickness is elevated, a correction factor can be applied. The amount/magnitude of correction factor is influenced by the magnitude of increase in soft tissue thickness that can be influenced by the magnitude of fat, fibrous, and muscle tissue contribution. Clinical study groups can be evaluated to generate databases for further study or to generate more refined correction factors. Such study groups include: non-edematous non-osteoporotic premenopausal, non-edematous non-osteoporotic postmenopausal, non-edematous osteoporotic postmenopausal; edematous non-osteoporotic premenopausal, edematous non-osteoporotic postmenopausal, and edematous osteoporotic postmenopausal patients. In each study group the following procedures can be performed for comparison: dual x-ray absorptiometry ("DXA") of the spine, hip, or calcaneus, along with SOS and BUA measurements or quantitative computed tomography ("QCT"). Thus, correction for soft tissue thickness can also improve the accuracy and discriminatory power in the analysis of x-rays and other x-rays. Such methods can also be used to identify population with an increased or decreased risk of bone conditions such as osteoporosis.

4.0. Applications

The measurements of bone mineral density or trabecular architecture and/or macro-anatomical and/or biomechanical parameters, for example in the mandible or maxilla or in the hip or in the spine, can be used to derive an assessment of bone health in any subject. Additionally, the analysis and manipulation of data from x-rays allows for the assessment of bone health that in turn can be used to prescribe a suitable treatment regime. Efficacy of a treatment regime can also be assessed using the methods and devices described herein (for example, using measurements of bone mineral density or trabecular architecture and/or macro-anatomical and/or biomechanical parameters in the mandible or the maxilla or the hip or the spine taken at two separate time points T1 and T2 to detect any difference in bone mineral density or trabecular architecture).

In addition, the methods described herein permit, for example, fully automated assessment of the structural organization and architectural arrangement of trabecular bone and/or macro-anatomical and/or biomechanical parameters on standard hip radiographs as well as improved tools for monitoring progression of osteoporosis and therapeutic response. In certain embodiments, the methods involve binarizing and skeletonizing trabecular bone using morphological operators with detection of branch points and endpoints of the skeleton network and classification into free-end segments and node-to-node segments. In other embodiments, the methods involve measuring trabecular density, trabecular perimeter, trabecular bone pattern factor, segment count, segment length, angle of segment orientation and ratio of node-to-node segments to free-end segments based on the binarized and/or skeletonized images. In still further embodiments, the methods involve (a) measuring trabecular thickness using a Euclidean distance transform (see, also Example 3); (b) assessing trabecular orientation using a 2D Fast Fourier Transform; and/or (c) creating a bone structure index for diagnosing osteoporosis or for predicting fracture risk combining at least two or more of these structural parameters.

In certain embodiments, the radiograph is of a subject's hip. Furthermore, to help control the influence of radiographic positioning on the accuracy of bone structure and/or macro-anatomical and/or biomechanical measurements, the methods may include one or more of the following: evaluating the angular dependence of bone structure measurements in the hip, for example by comparing antero-posterior radiographs of the hip joint in healthy to osteoporotic patients (subjects) with the femur radiographs in neutral position and in various degrees of internal and external rotation or by obtaining radiographs of the hip with different degrees of tube angulation. Bone structure and/or macro-anatomical and/or biomechanical measurements can be compared between the different positions to determine which bone structure parameters show the least dependence on radiographic positioning and/or using a foot holder to fix the patients' foot in neutral position in case pair wise coefficients of variation between the results for the 0° neutral position and a 15° internal or external rotation position exceed 10% for the majority of the structural parameters measured.

In other embodiments, methods of monitoring bone structure and/or macro-anatomical and/or biomechanical parameters over time (e.g., longitudinally) are also provided, for example to assess progression of osteoporosis and/or response to therapy. In certain embodiments, the methods involve automated placement of regions of interest (ROI) in the hip joint, for example by creating and using a general model of the proximal femur that includes six defined regions of interest (ROI's).

The methods described herein, which allow, in part, for the measurement of bone structure are useful in both the diagnosis and treatment of osteoporosis. Ultimately, these techniques could help screen large numbers of women at risk for osteoporosis in a highly cost-effective and accurate manner using standard, widely available radiographic equipment without the need for expensive dedicated capital equipment. It is clear that a program of this type would be powerfully enabling for therapeutic intervention with new anabolic or anti-resorptive drugs that are needed to prevent the expected pandemic of osteoporotic fractures.

4.1. Kits

The invention also provides kits for obtaining information from images, for example for obtaining information regarding bone structure, micro-architecture, macro-anatomical and/or biomechanical parameters from an image such as a radiograph. In certain embodiments, the kit comprises one or more computer (e.g., software) programs, for example for receiving, analyzing and generating reports based on the image(s). In further embodiments, the kits can include calibration phantoms, for example calibration phantoms integrated or attachable—to a holder, hygienic cover, x-ray film and/or x-ray film holders.

The invention also provides for therapeutic kits, for example for treating osteoporosis or dental disease. In certain embodiments, the kits comprise a calibration phantom for use with one or more x-ray films, a computer software product, a database, a therapeutic drug and, optionally, instructions for use (e.g., instructions regarding positioning the calibration phantom while taking the x-ray, using the software to analyze the x-ray, dosages and the like. The therapeutic drug can be, for example, anti-resorptive or anabolic.

4.2. Diagnosis and Prediction

In yet another aspect, methods of diagnosing or predicting bone-related disorders (e.g., osteoporosis, Paget's Disease, osteogenesis imperfecta, bone cancers), periodontal disease or oral implant failure in a subject are provided, for example using any of the kits, methods and/or devices described herein. It will be apparent that these methods are applicable to any bone-related disorder including, for example, osteoporosis, bone cancer, and the like, as well as to periodontal disease and implant failure.

Osteoporosis alone is a major public health threat for 25 million postmenopausal women and 7 million men. In 1995, national direct expenditures for osteoporosis and related fractures were $13 billion. Changing demographics, with the growth of the elderly population, steadily contribute to increasing numbers of osteoporotic fractures and an incipient and potentially economically unmanageable epidemic of osteoporosis. Projections put the total cost of osteoporosis in the United States alone at more than 240 billion dollars per year in 40 years.

Less than 20% of the patients know they have the disease and many fewer receive physician directed specific therapy. A major impediment in successfully dealing with the impending osteoporosis epidemic is not a lack of treatment modalities but the inability to identify persons at risk and who require treatment. The limited access to osteoporosis testing is largely the result of the high cost of the currently available systems resulting in a small installed base limited to hospitals and specialty clinics.

The devices and methods described herein address these and other issues by providing inexpensive and reliable bone structural analysis screens and resulting diagnosis of bone condition and/or presence of disease. Indeed, while measurements of bone mineral density (BMD) are technically relatively easy to perform, low BMD accounts for considerably less than 100% of fracture risk although it is well established that progressive disruption of trabecular structure and architecture contribute in a major way to fracture risk in older individuals.

Thus, in certain embodiments, the methods comprise using a computer program to analyze bone mineral density or bone structure and/or macro-anatomical and/or biomechanical parameters of an image (e.g., x-ray image) and comparing the value or measurement obtained from the image with a reference standard or curve, thereby determining if the subject has a bone-related condition such as osteoporosis or thereby determining a subject's fracture risk. The image can also include a calibration phantom, for example a calibration phantom as described herein.

In certain embodiments, measurements of bone structure can be combined or correlated with measurements of macro-anatomical and/or biomechanical parameters (e.g., cortical thickness on a hip x-ray), for example using statistical or mathematical methods, to create an index for the severity of the disease. Subsequently, the index can be used for diagnosing osteoporosis or for predicting fracture risk combining at least two or more of these bone structure or morphological parameters.

4.3. Treatment

The methods and devices described herein can also be used to develop an appropriate treatment regime for a subject in need thereof. Additionally, the invention allows for the ongoing analysis of the efficacy of a subject's treatment regime.

Although estrogen deficiency after menopause is one of the most well documented causes of osteoporosis that can be prevented by hormone replacement therapy (HRT), HRT may also cause an increase (approximately 35%) in the risk of breast cancer in long-term users. *Lancet* (1997)350:1047-1059. Consequently, much effort has been devoted to developing alternative treatments for osteoporosis. Among those treatments, bisphosphonates are becoming increasingly recognized as the treatment of choice. Lin (1996) *Bone* 18:75-85; Liberman et al. (1995) *N Engl J Med* 333:1437-1443; Mortensen et al. (1998) *J Clin Endocrinol Metab* 83:396-402. Another new class of therapeutic agents recently introduced is the selective estrogen receptor modulators (SERMs). Delmas et al. (1997) *N Engl J Med* 337:1641-1647; Lufkin et al. (1998) *J Bone Min Res* 13:1747-1754. Anabolic therapies such as parathyroid hormone have also been suggested for treatment of osteoporosis. Roe et al. (1999) *J Bone Miner Res* 14(suppl1):S137, Abst#1019; Lane et al. (1998) *J Clin Invest* 102:1627-33.

The combined results of these and other studies suggest that effective treatments for osteoporosis can be developed once the condition is diagnosed. For instance, using any of the methods, kits, and/or devices described herein, the presence of osteoporosis in a subject can be diagnosed and that subject provided with appropriate therapy (e.g., one or more antiresorptive agents and/or one or more anabolic agents). Periodontal disease can be similarly diagnosed and treatments ranging from oral hygiene practices to surgery can be recommended. Over time, the methods and compositions described herein can be used to assess the efficacy of the selected treatment and the treatment regime altered as necessary. For example, a subject can be given a one-time or ongoing therapy and images evaluated after such therapy to monitor its effectiveness. Thus, in certain embodiments, treatment or monitoring of treatment of bone related disorders are provided.

4.4. Decision Trees

Thus, diagnosing, predicting, developing treatment regimes, assessing treatment efficacy and the like can be readily accomplished using the methods described herein. In certain aspects, these applications will be accomplished using algorithms or decision trees (also known as logic trees or flow charts). One exemplary decision tree is provided in regard to predicting bone problems. It will be readily apparent that such decision trees are equally applicable to other applications (e.g., designing treatment regimes, assessing treatment efficacy, etc.).

One exemplary method for predicting bone problems (e.g., osteoporoses, etc.), periodontal disease or oral implant failure employs a decision tree (also called classification tree) which utilizes a hierarchical evaluation of thresholds (see, for example, J. J. Oliver, et. al, in Proceedings of the 5th Australian Joint Conference on Artificial Intelligence, pages 361-367, A. Adams and L. Sterling, editors, World Scientific, Singapore, 1992; D. J. Hand, et al., Pattern Recognition, 31(5):641-650, 1998; J. J. Oliver and D. J. Hand, Journal of Classification, 13:281-297, 1996; W. Buntine, Statistics and Computing, 2:63-73, 1992; L. Breiman, et al., "Classification and Regression Trees" Wadsworth, Belmont, Calif., 1984; C4.5: Programs for Machine Learning, J. Ross Quinlan, The Morgan Kaufmann Series in Machine Learning, Pat Langley, Series Editor, October 1992, ISBN 1-55860-238-0). Commercial software for structuring and execution of decision trees is available (e.g., CART (5), Salford Systems, San Diego, Calif.; C4.5 (6), RuleQuest Research Pty Ltd., St Ives NSW Australia) and may be used in the methods of the present invention in view of the teachings of the present specification. A simple version of such a decision tree is to choose a threshold bone structure and/or macro-anatomical and/or biomechanical or bone mineral density reading at a particular anatomical landmark (e.g., edge of mandible or maxilla, the end of a tooth root, etc.). If a value is equal to or below the threshold bone data value, then more of the image is evaluated. If more of the image is below the threshold value, then a bone problem, periodontal disease or implant failure is predicted.

For example, a first level decision is made by the algorithm based on the most recent x-ray images obtained and analyzed as described herein is compared to initial thresholds that may indicate an impending or current bone- or periodontal-related event. For example, the algorithm may compare the current bone structure measurements (time=n) or a predicted bone structure measurement (time=n+1) to a threshold value. If the bone structure measurement is greater than the threshold value then a decision is made by the algorithm to suggest further future x-rays. If the bone structure measurement is less than or equal to the threshold level(s) then the algorithm continues with the next level of the decision tree.

The next level of the decision tree may be an evaluation of the subject's age and/or gender at time (n) that x-ray is taken, which is compared to a threshold bone measurement for "normal" subjects of that age and/or gender. For example, if the subject's bone measurement is greater than the threshold bone structure level for that particular age and/or gender, then a decision is made by the algorithm to prompt further monitoring in the future. If the information on bone structure is less than or equal to the threshold, then the algorithm continues with the next level of the decision tree.

The next level of the decision tree may be, for example, an evaluation of the subject's soft tissue (e.g., gum) thickness (n), which is compared to a threshold measurement. For example, if the soft tissue is significantly below or above the normal range of thickness, then a decision is made by the algorithm to examine more of the x-ray image or to predict a bone-related problem.

The decision tree could be further elaborated by adding further levels. For example, after a determination that a bone and/or periodontal events are possible, the subject can be x-rayed again to see if values have changed. Again, age, gender, weight, soft tissue thickness and the like can also be tested and considered to confirm the prediction.

In such decision trees, the most important attribute is typically placed at the root of the decision tree. In one embodiment of the present invention the root attribute is the current bone structure measurement(s). In another embodiment, a predicted bone structure measurement at a future time point may be the root attribute. Alternatively, bone mineral density and/or implant structure could be used as the root attribute.

Further, thresholds need not (but can) be established a priori. The algorithm can learn from a database record of an individual subject's readings and measurements. The algorithm can train itself to establish threshold values based on the data in the database record using, for example, a decision tree algorithm.

Further, a decision tree may be more complicated than the simple scenario described above. For example, if soft tissue of a particular subject is very thick, the algorithm may set a threshold for the bone measurements that is higher or lower than normal.

By selecting parameters (e.g., current or future bone information, etc.) and allowing the algorithm to train itself based on a database record of these parameters for an individual subject, the algorithm can evaluate each parameter as independent or combined predictors of disease and/or implant failure. Thus, the prediction model is being trained and the algorithm determines what parameters are the most important indicators. A decision tree may be learnt in an automated way from data using an algorithm such as a recursive partitioning algorithm. The recursive partitioning algorithm grows a tree by starting with all the training examples in the root node. The root node may be "split," for example, using a three-step process as follows. (1) The root node may be split on all the attributes available, at all the thresholds available (e.g., in a training database). To each considered split a criteria is applied (such as, GINI index, entropy of the data, or message length of the data). (2) An attribute (A) and a threshold (T) are selected which optimize the criteria. This results in a decision tree with one split node and two leaves. (3) Each example in the training database is associated with one of these two leaves (based on the measurements of the training example). Each leaf node is then recursively split using the three-step process. Splitting is continued until a stopping criteria is applied. An example of a stopping criteria is if a node has less than 50 examples from the training database that are associated with it.

In a further embodiment, at each level of the decision in the decision tree, the algorithm software can associate a probability with the decision. The probabilities at each level of decision can be evaluated (e.g., summed) and the cumulative probability can be used to determine whether disease and/or implant failure is predicted.

Receiver Operating Characteristic (ROC) curve analysis can be applied to decision tree analysis described above. ROC analysis is another threshold optimization means. It provides a way to determine the optimal true positive fraction, while minimizing the false positive fraction. A ROC analysis can be used to compare two classification schemes, and determine which scheme is a better overall predictor of the selected event (e.g., evidence of osteoporosis); for example, a ROC analysis can be used to compare a simple threshold classifier with a decision tree. ROC software packages typically include procedures for the following: correlated, continuously distributed as well as inherently categorical rating scale data; statistical comparison between two binormal ROC curves; maximum likelihood estimation of binormal ROC curves from set of continuous as well as categorical data; and analysis of statistical power for comparison of ROC curves. Commercial software for structuring and execution of ROC is available (e.g., Analyse-It for Microsoft Excel, Analyse-It Software, Ltd., Leeds LS12 5XA, England, UK; MedCalc®, MedCalc Software, Mariakerke, Belgium; AccuROC, Accumetric Corporation, Montreal, Quebec, Calif.).

Related techniques that can be applied to the above analyses include, but are not limited to, Decision Graphs, Decision Rules (also called Rules Induction), Discriminant Analysis (including Stepwise Discriminant Analysis), Logistic Regression, Nearest Neighbor Classification, Neural Networks, and Naïve Bayes Classifier.

All of these aspects of the invention can be practiced separately or in combination. Typically, the use of combinations of the embodiments listed above is more advantageous. Further, although preferred embodiments of the subject invention have been described in some detail, it is understood that obvious variations can be made without departing from the spirit and the scope of the invention.

EXPERIMENTAL

Below are examples of specific embodiments for carrying out the present invention. The examples are offered for illustrative purposes only, and are not intended to limit the scope of the present invention in any way.

Example 1

In Vivo Reproducibility and In Vivo Diagnostic Sensitivity

A. Dental X-Rays

In order to test in vivo reproducibility of data obtained from dental x-rays, the following experiment was performed. Subjects sat in a dental chair and an x-ray was taken of the area of the incisor teeth and of the molar teeth of the mandible. A calibration phantom step wedge was attached to the dental x-ray film. The dental x-ray film was exposed using standard x-ray imaging techniques for x-rays of the incisor area. The subjects walked around for 15 minutes at which point that test was repeated using the same procedure.

X-ray films were digitized on a commercial flat-bed scanner with transparency option (Acer ScanPremio ST). The regions of interest (ROIs) were placed manually at the same position with respect to the dental roots in all digitized x-rays of the same subject using the NIH Image software program (http://rsb.info.nih.gov/nih-image/Default.html). The reproducibility of the measurement of the average gray values inside the ROIs was determined as the coefficient of variation (COV=standard deviation of measurements/mean of measurements). Overall results are given as root mean square

TABLE 2

Reproducibility of measurements of average gray values in digitized dental x-rays

| Region | COV Subject A | COV Subject B | RMS |
|---|---|---|---|
| Incisor | 2.9% (n = 3) | 5.9% (n = 3) | 4.6% |
| Molar | 3.0% (n = 3) | 4.1% (n = 4) | 3.6% |
|  |  | All regions: | 4.2% | over both subjects. The data are summarized in Table 2.

$$\left( RMS = \sqrt{\sum_1^n x_i^2 / n} \right)$$

The data show that reproducibility is achieved that is already comparable with that of many ultrasound systems to diagnose osteoporosis.

B. Hip Radiographs

To test whether bone texture analysis in hip x-rays can detect differences between normal and osteoporotic bone, sample hip x-ray images were acquired in two patients with a Fuji FCR 5000 computed radiography system (Fuji Medical Systems, Stemford, Conn.). The first patient had normal bone mineral density in the hip as measured by DXA. In the second patient, femoral neck BMD measured by DXA was one standard deviation below normal.

For x-ray imaging, patients were positioned on the x-ray table in supine position, parallel to the long axis of the table. The patient's arms were placed alongside their body. Patient comfort was ensured with a pillow underneath the patient's neck. However, no pillows were used underneath the knees. The x-ray technologist checked that the patient lies straight on the table by looking from the head down towards the feet (which were placed in neutral position with the toes pointing up. The ray was centered onto the hip joint medial and superior to the greater trochanter.

Anteroposterior hip radiographs were acquired using the following parameters: Film-focus distance: 100 cm; tube voltage: 65 kVp; exposure: phototimer for automatic exposure or approximately 20 mAs for manual exposure; collimation: limited to the hip joint, including proximal femoral diaphysis; centering: over femoral head (see above); tube angulation: zero degrees. An aluminum step wedge (Bio-Quest, Tempe, Ariz.) was included in the images to calibrate gray values before further image analysis. Processing was performed using ImageJ, a Java version of NIH image (http://rsb.info.nih.gov/ij/).

Six regions of interest were selected manually at the approximate locations as shown in FIG. 9. Trabeculae were extracted through background subtraction. The resulting binarized images are shown in the Figures. In a next step, the trabecular bone in the selected regions of interest was skeletonized.

The binarized ROI's in the normal and the osteopenic patient were used to determine the trabecular density ratio (trabecular area vs. ROI area). The following bone structure measurements were obtained from the skeletonized ROIs; mean segment length, total skeleton length (normalized by ROI area), skeleton segment count (normalized by ROI area), and skeleton node count (normalized by ROI area). Results are shown in Tables 3 through 7.

TABLE 3

Trabecular Density Ratio (Trabecular Area/ROI Area)

|  | ROI A | ROI B | ROI C | ROI D | ROI E | ROI F |
|---|---|---|---|---|---|---|
| Normal | 0.473 | 0.482 | 0.514 | 0.494 | 0.476 | 0.485 |
| Osteopenia | 0.382 | 0.455 | 0.492 | 0.426 | 0.424 | 0.455 |
| % Osteopenia vs. Normal | 81% | 94% | 96% | 86% | 89% | 94% |

TABLE 4

Mean skeleton segment length

|  | ROI A | ROI B | ROI C | ROI D | ROI E | ROI F |
|---|---|---|---|---|---|---|
| Normal | 7.116 | 8.071 | 10.765 | 8.175 | 8.272 | 7.313 |
| Osteopenia | 7.146 | 9.877 | 10.004 | 6.699 | 8.607 | 9.750 |
| % Osteopenia vs. Normal | 100% | 122% | 93% | 82% | 104% | 133% |

TABLE 5

Total Skeleton Length (normalized by ROI area)

|  | ROI A | ROI B | ROI C | ROI D | ROI E | ROI F |
|---|---|---|---|---|---|---|
| Normal | 0.0736 | 0.0758 | 0.0906 | 0.0889 | 0.0806 | 0.0785 |
| Osteopenia | 0.0503 | 0.0589 | 0.0672 | 0.0584 | 0.0681 | 0.0543 |
| % Osteopenia vs. Normal | 68% | 78% | 74% | 66% | 84% | 69% |

TABLE 6

Skeleton segment count (normalized by ROI area)

|  | ROI A | ROI B | ROI C | ROI D | ROI E | ROI F |
|---|---|---|---|---|---|---|
| Normal | 0.0100 | 0.0094 | 0.0084 | 0.0109 | 0.0097 | 0.0107 |
| Osteopenia | 0.0070 | 0.0060 | 0.0067 | 0.0087 | 0.0079 | 0.0056 |
| % Osteopenia vs. Normal | 68% | 63% | 80% | 80% | 81% | 52% |

TABLE 7

Skeleton node count (normalized by ROI area)

|  | ROI A | ROI B | ROI C | ROI D | ROI E | ROI F |
|---|---|---|---|---|---|---|
| Normal | 0.0198 | 0.0210 | 0.0229 | 0.0244 | 0.0156 | 0.0240 |
| Osteopenia | 0.0090 | 0.0117 | 0.0132 | 0.0113 | 0.0088 | 0.0081 |
| % Osteopenia vs. Normal | 46% | 56% | 58% | 47% | 56% | 34% |

These results demonstrate that the evaluation of trabecular structure reveals significant differences between normal and osteopenic bone and that selective analysis of trabeculae oriented in certain directions in the different ROI allows for the assessment of structures critical for biomechanical stability of the proximal femur.

C. Spine Radiographs

To test whether bone texture analysis in spine x-rays can detect differences between normal and osteoporotic bone, sample spine x-ray images will be acquired in more than one patient. In the spine, the bone structure parameters can be measured in the L1, L2, L3 and L4 vertebral bodies unless obscured by superimposed ribs, iliac crest or bowel gas. The first patient will provide control data provided the patient has normal bone mineral density in the spine. In the second patient and subsequent patients, spine BMD will be measured.

Figure 22:
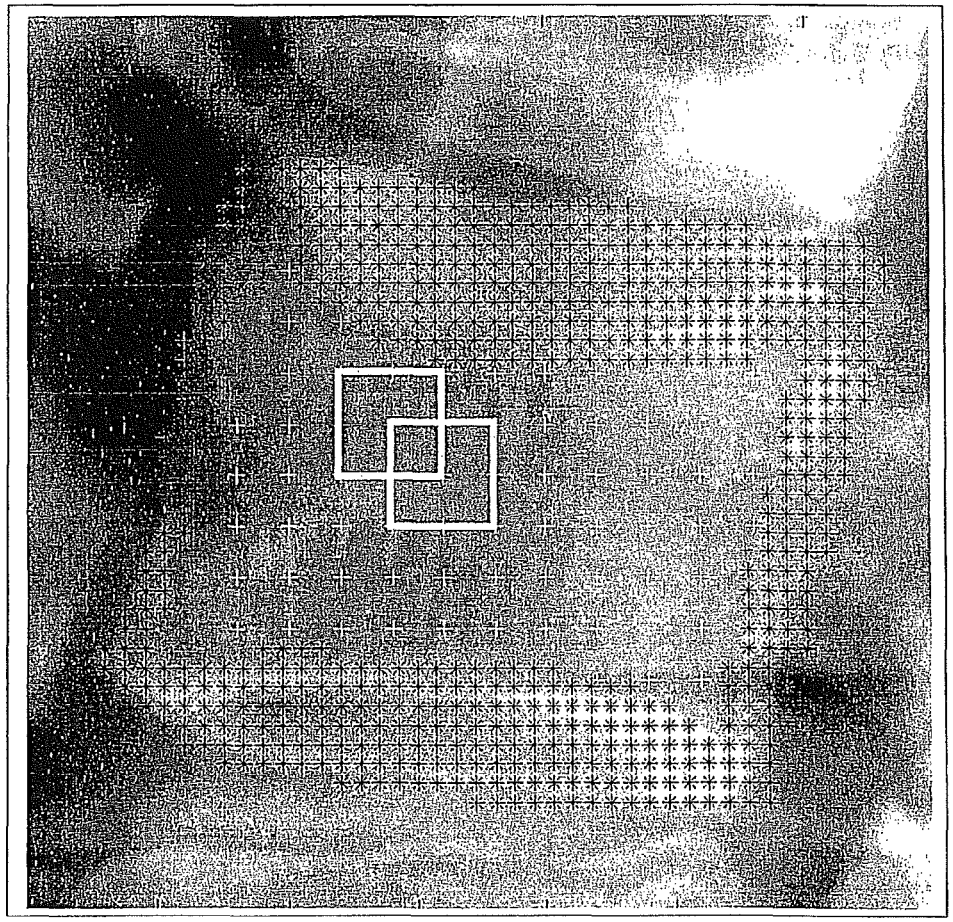
FIG. 22 depicts an example of a regular interval sampling field for microarchitecture (+) and a higher density sampling field for macro-anatomical features (*) on a spine radiograph. White rectangles are examples of overlapping window positioning.
Figure 24:
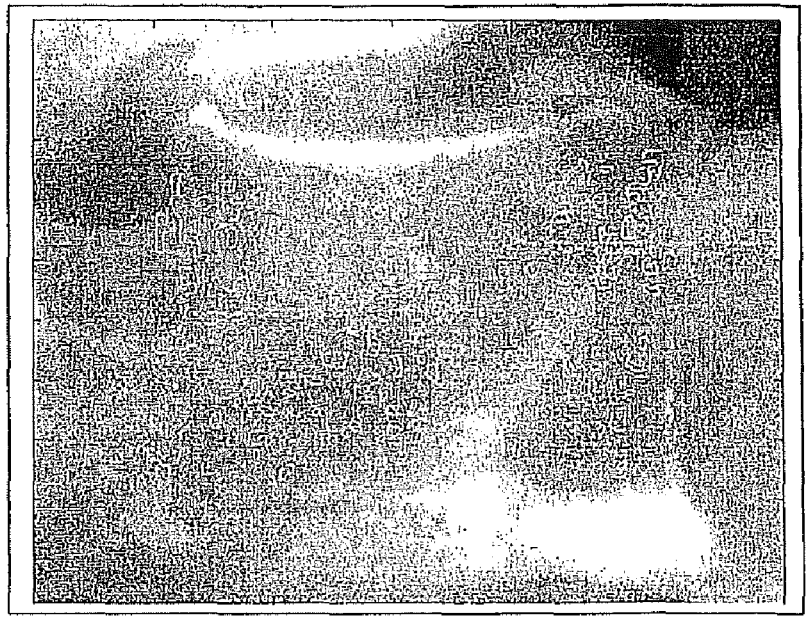
FIG. 24 depicts an example of an application of structure extraction and measurement for therapeutic monitoring using spine x-ray. White outline of extracted structure are show in (a) before treatment, and (b) after treatment.
Figure 24:
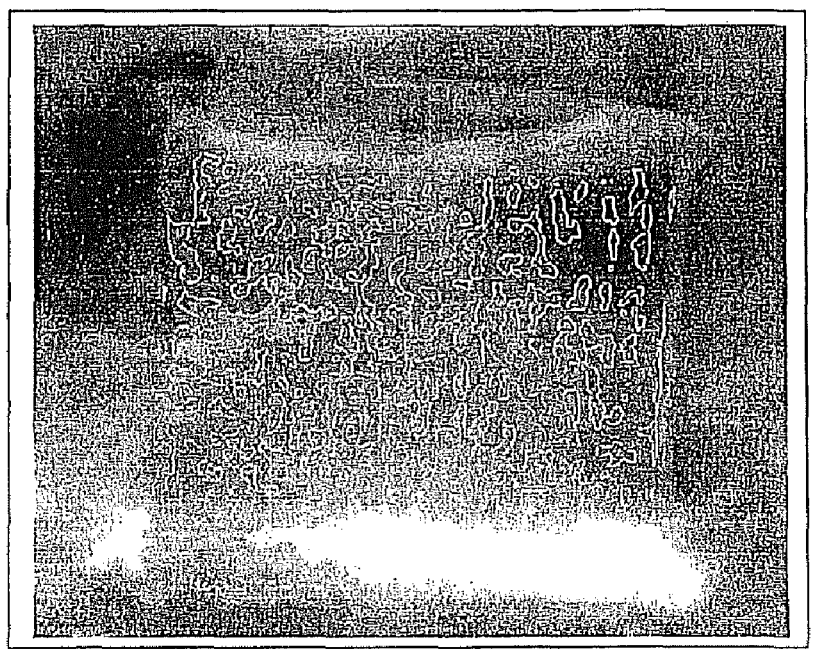

Regions of interest will be selected manually at the approximate locations as shown in FIG. 22. Trabeculae will be extracted through background subtraction. In a next step, the trabecular bone in the selected regions of interest was skeletonized. FIG. 24 depicts an example of an application of structure extraction and measurement for therapeutic monitoring using spine x-ray. White outline of extracted structure are show in (a) before treatment, and (b) after treatment.

D. Knee/Tibial Radiographs—Osteoporosis

To test whether bone texture analysis in knee and tibial x-rays can detect differences between normal and osteoporotic bone, sample x-ray images will be acquired in more than one patients. The first patient will provide control data provided the patient has normal bone mineral density or bone structure in the tibia or femur. In the second patient and subsequent patients, joint BMD or bone structure will be measured.

Figure 23:
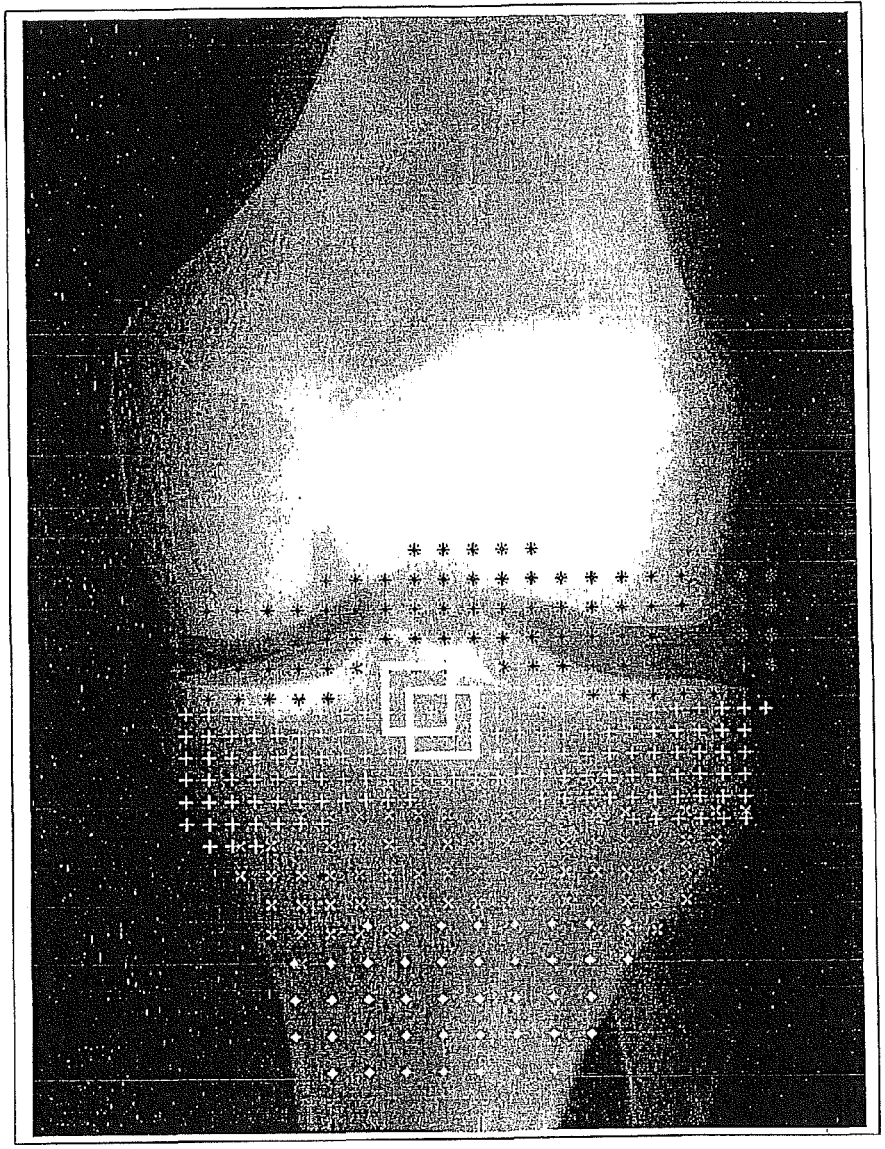
FIG. 23 depicts an example of a sampling field of varying density for microarchitecture (+, x, diamond) and a regular sampling field for macro-anatomical features (*) on a knee radiograph. White rectangles are examples of overlapping window positioning.

Regions of interest will be selected manually at the approximate locations as shown in FIG. 23. The ROI can, for example, be the region immediately below the tibial plateau subchondral bone. Trabeculae will be extracted through background subtraction. In a next step, the trabecular bone in the selected regions of interest is skeletonized.

D. Knee/Tibial Radiographs—Arthritis

To test whether bone texture analysis in knee and tibial x-rays can detect differences between normal patients and patients with arthritis, sample x-ray images will be acquired in more than one patients. The first patient will provide control data provided the patient has normal bone mineral density or bone structure in the tibia or femur. In the second patient and subsequent patients, joint BMD or structure will be measured.

Regions of interest will be selected manually at the approximate locations as shown in FIG. 23. The ROI can, for example, be the region immediately below the tibial plateau subchondral bone. Trabeculae will be extracted through background subtraction. In a next step, the trabecular bone in the selected regions of interest is skeletonized.

Example 2

Image Processing Techniques

Techniques to analyze structure of trabeculae in different regions of the femoral head, neck, and proximal shaft are developed in Matlab (The MathWorks, Inc., Natick, Mass.) on PC's. The following techniques (modules) are developed: algorithms for software analysis of density, length, thickness, and orientation of trabeculae in different regions of interest (ROI) in the radiograph and a technique for automated placement of these ROI.

Six regions of interest are selected in the proximal femur for bone microstructure evaluation. The size and shape of these ROI are designed to capture the local changes of trabecular density and structure (see, e.g., FIG. 9), and may reflect the location of the different compressive and tensile groups of trabeculae. Singh et al. (1970) J Bone Joint Surg Am. 1970. 52:457-467. Thus, a classification scheme based on statistical convergence of multiple parameters that would provide a high precision index for predicting hip fractures is developed.

Example 3

Bone Structure Analysis of Hip Radiographs

The trabeculae in the femur is extracted using the background subtraction method, essentially as described in Geraets et al. (1998) Bone 22:165-173. A copy of the image is blurred with a 15×15 Gaussian filter, and the result represents the non-uniform background. This background image is subtracted from the original image to obtain an image of trabecular structure. This image is then transformed into binary image of trabecular structure by applying a threshold value of 0. An example of the end result is shown in FIG. 10.

In a second step, parameters relevant to the geometry and connectivity of trabecular structure are measured on the trabecular skeleton or centerline. The skeletonization is performed using morphological hit-or-miss thinning for example as described in Soille, "Morphological image analysis: principles and application" Springer, 1998: p. 129-154. The branch points and end points of the skeleton network are detected, and the skeleton segments are classified as free-end segments and node-to-node segments.

One or more of the following parameters from the binarized and from the skeletonized ROI's are used: trabecular density; ratio of trabecular area to total ROI area; trabecular perimeter; star volume (Ikuta et al. (2000) J Bone Miner Res. 18:271-277; Vesterby (1990) Bone 11:149-155); trabecular bone pattern factor (Hahn et al. (1992) Bone 13:327-330); Euclidean distance transform; assessment of trabecular orientation using Fourier analysis; and orientation-specific trabecular assessment. Further, one or more of the following parameters can be measured in each ROI on the network of skeletonized trabeculae as a whole, all skeleton segments, and each type of segment: segment count; segment length; angle of segment orientation; and Interconnectivity Index (Legrand et al. (2000) J. Bone Miner Res. 15:13-19): normalized ratio of the number of node-to-node segments to free-end segments.

For example, in Euclidean Distance Transform each pixel on the binarized trabeculae is assigned a value equal to its Euclidean distance from the structure boundary. Thus, thicker trabeculae will have larger distance transform values in the center, thereby estimating trabecular thickness calculates the mean of the distance transform values along the trabecular skeleton (see FIG. 11). Further, multiplying this value by 2 provides a measurement of trabecular thickness.

Figure 12:
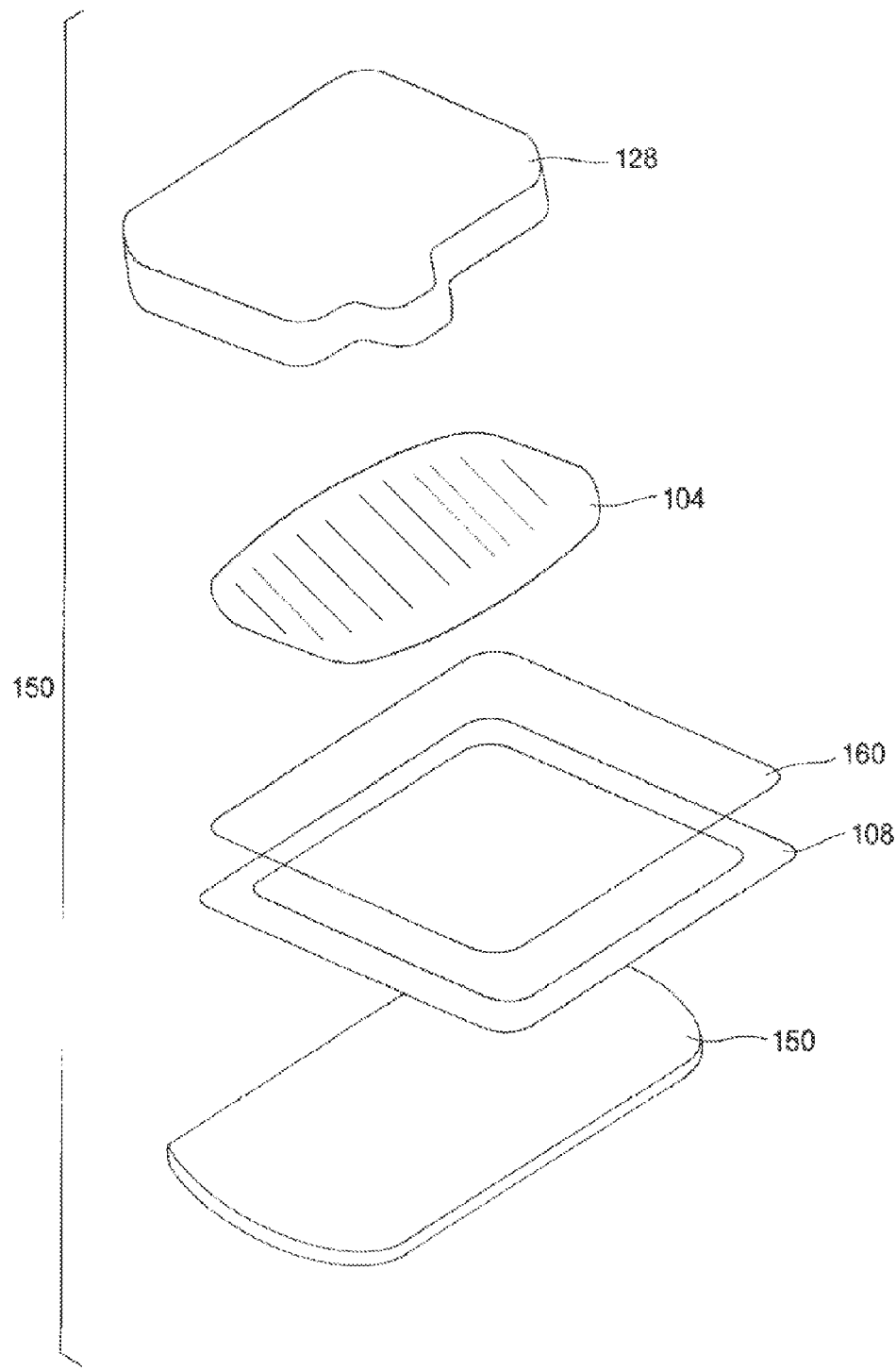
FIG. 12 shows an example of a hygienic cover holder that includes compartments for a calibration phantom and a fluid-filled bolus back.

Similarly, predominant trabeculae orientation may be evaluated using the 2D Fast Fourier Transform (FFT). A rectangular region is selected within each ROI and multiplied with a 2D Kaiser window before applying the transform (see FIG. 12, left). The log of the Fourier magnitude is taken to form an image representing the frequency domain of the ROI. The result is then filtered with a 5×5 Gaussian filter to reduce local variation. An example image is shown in FIG. 12, center. The Fourier image is subsequently thresholded at a fixed magnitude level. This binary image is resampled to a square image to normalize the length of the vertical and horizontal axes, and the direction and length of its major axis are determined (FIG. 12, right). The angles will be measured with respect to the axes of the femoral neck and shaft. The axes are determined by fitting lines to the two longest segments of the centerline of the binarized femur (see also FIG. 14). The ROI's are located such that they include the different groups of compressive and tensile trabeculae in the proximal femur that each can be characterized by a specific direction. A fully automated technique to evaluate the different quantitative structural parameters explained above for those trabeculae in each of the ROI that are oriented in the characteristic direction expected for the particular ROI is developed.

The orientation of each trabecular skeleton segment is found through the gradient of the line fitted to the skeleton points. Based on this orientation information, only those trabeculae are considered in the evaluation of the structure parameters that are approximately oriented in the characteristic direction for a particular ROI.

As will be appreciated by those of skill in the art, all measurements can be constrained by one or more desired orientation by measuring only segments within specified angle ranges. The statistics of watershed segments include: number of segments, total area of segments, average area of segments, standard deviation of segment area, smallest segment area, and largest segment area. These segments are, however, general in nature.

When evaluating the hip, additional parameters can be considered. Parameters include, for example, shaft angle, neck angle, diameter of the femur neck, the hip axis length, the largest cross-section of the femur head, the average thickness of the cortical region within a ROI, the standard deviation of cortical thickness within a ROI, or the maximum or minimum thickness of the cortical thickness within a ROI.

In contrast, when evaluating the spine, additional parameters to be considered include, for example, all parameters on vertical structures, all parameters on horizontal structures, vertebral cortical thickness, maximum vertebral height, minimum vertebral height, average vertebral height, anterior vertebral height, medial vertebral height, posterior vertebral height, maximum inter-vertebral height, minimum inter-vertebral height, and average vertebral height.

The knee and tibial region can be evaluated using the additional parameters of: average medial joint space width, minimum medial joint space width, maximum medial joint space width, average lateral joint space width, minimum lateral joint space width and maximum lateral joint space width.

As will be appreciated by those of skill in the art, the additional parameters listed for these exemplar anatomies above can include other parameters. Additionally, parameters can be evaluated for other anatomies not specifically set forth without departing from the scope of the invention.

Example 4

Multidimensional Classification

Example 3 describes a number of parameters that are measured to assess trabecular structure in different regions of the proximal femur. In this Example, the different structural parameters are combined in each section, and a single index is determined over all regions of interest.

A training set of hip x-ray images of a group of subjects are divided into the two categories "osteoporosis" and "no osteoporosis", based on previous DXA results. Subsequently, for all x-rays in the training set, the parameters listed in Example 3 are calculated for all regions of interest placed as described in Example 3, resulting in a set of m-dimensional prototype feature vectors $f_i=(f_{i1}, \ldots, f_{im})^T$ for the training set $I=\{I_i\}$, $i=1, \ldots, n$.

For each parameter a single scalar index value is calculated. All index values are combined into one n-dimensional feature vector. In one step, the system is trained with the data from clinical validation studies with premenopausal, postmenopausal healthy and postmenopausal osteoporotic subjects. The subject groups are preferably divided into a "fracture" and a "no fracture" category. The feature vectors calculated from the x-ray images are used as prototype patterns.

For each patient, a feature vector is calculated from the x-ray as calculated for the prototype patterns and an individual patient classified as category C if the majority of the k closest prototype patterns is of the category C. The distance d between the patient's feature vector $f=(f_1, f_2, \ldots, f_n)^T$ and a prototype pattern $p=(p_1, p_2, \ldots, p_n)^T$ is defined by the Euclidean norm $L_2$:

$$d(f, p) = L_2(f, p) = \sqrt{\sum_{i=1}^{n} (f_i - p_i)^2}$$

The optimum scale for the different parameters is also preferably determined. However, for some parameters differences in the index values between the categories is smaller than for others. Also, the optimum k will be determined. Increasing k is expected to improve the accuracy of the classification, but it has to be smaller than the number of prototypes in each category. The exact percentage value of the majority of the k closest prototype patterns that determines the classification provides a measure for the reliability of the classification. The higher the percentage of prototype patterns from a particular category C, the more significant the information provided by the classification is likely to be.

This classification approach is validated with a series of leave-one-out experiments using the 0° neutral position images of the femoral position study (see Example 8) and the baseline hip x-rays of the short-term in vivo reproducibility study. For these experiments, each subject is preferably used as a test case once. The training set for the system consists of the patterns calculated for all or most of the remaining subjects. The test case is correctly classified using this training set, and the diagnostic sensitivity and specificity of the combination of bone structure parameters is determined.

In addition to the measurements described above (which provide index values for the parameters "length of trabeculae", "direction of trabeculae and anisotropy", and "trabecular thickness"), additional measurements for other parameters in the classification system that have been explored in the past to study bone density and structure from x-ray, CT, and MR images such as: (1) mean pixel intensity; (2) variance of pixel intensity; (3) Fourier spectral analysis; (4) fractal dimension; (5) morphological parameters such as the trabecular area, trabecular periphery, total trabecular length, number of terminal and branch points, as well as similar parameters for the bone marrow can be used.

Example 5

Automated Placement of Region of Interest (ROI)

Figure 13:
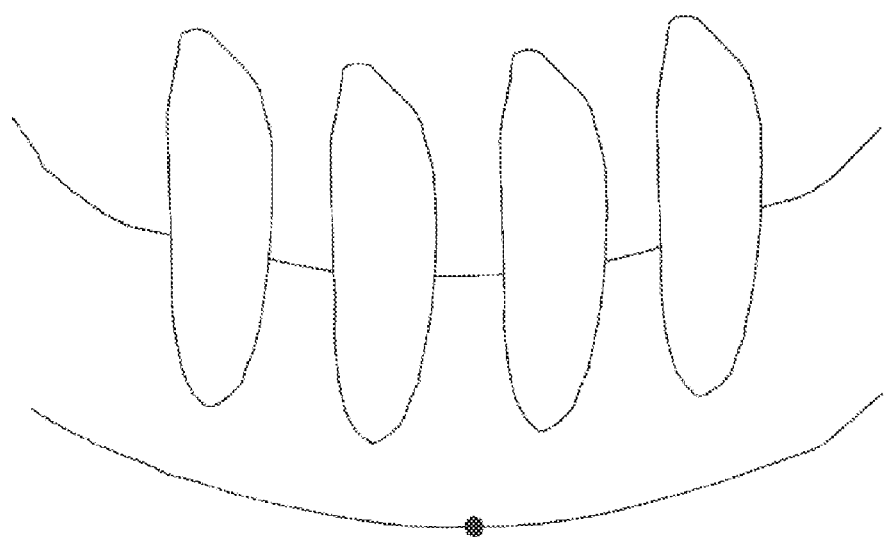
FIG. 13 shows an example of an anatomical region of interest (black dot), determined relative to the teeth or to the convexity/concavity of the mandible.

Analysis of x-rays (e.g., hip radiographs) may be facilitated by development of techniques that locate one or more regions of interest (ROI) used for the calculation of the structural parameters of the trabecular bone. For example, the general position of the femur can be located using a binary image of the hip radiographs thresholded at the appropriate gray value. In a typical hip radiograph, the femur is a bright structure extending from the pelvis. (FIG. 13). By thresholding the digitized radiograph at the typical femur intensity value, a binary image showing the femur is produced. The relatively thin structure of the femoral shaft can be extracted by applying a morphology operation on the binary image. The morphological top-hat filter (opening subtracted from input) with an upright rectangular structuring element segments the femoral shaft. The result is shown in FIG. 13 with outline of the binarized femur superimposed on the original radiograph. The region is cropped for further processing, preferably leaving enough room to include the femoral head.

Figure 14:
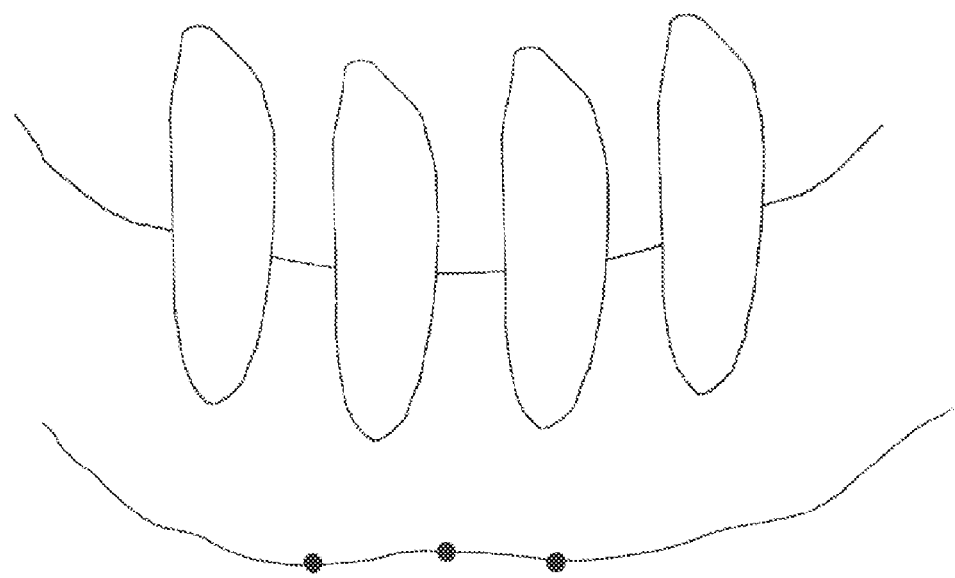
FIG. 14 shows an example of three anatomical region of interests (black dots), determined relative to the teeth or to the convexity/concavity of the mandible.

To position the set of predetermined ROI, a regularized active shape algorithm can be used (Behiels et al. (1999) Proceedings of the 2nd International Conference on Medical Image Computing and Computer-Assisted Intervention—MICCAI'99, Lecture notes in Computer Science 1679:128-137; Cootes (1994) Image and Vision Computing 12:355-366). A general model of the proximal femur is created by manually outlining the shape in a training set of typical hip radiographs to form a mean shape. The six predefined ROI are then embedded into this model. This mean model is scaled down 80%, isometrically along its centerline. This transformation is applied to the predefined ROI as well. The outline of the rescaled model is then used as the initial template and is positioned within the proximal femur in the input image. The control points of the contour are subsequently expanded outwards away from the nearest centerline point. The energy function to be optimized in this iterative process can take into account local features, such as gradient, intensity, deviation from the mean model, and curvature of contour segments. FIG. 14 illustrates the propagation of the initial control points towards the femur edge. When the iteration is completed, a deformation field for the model area is calculated. This deformation field is interpolated for the model ROI inside the boundaries of the femur model. The result is a new set of ROI that is adapted to the input image, but similar to the model ROI with respect to anatomical landmarks (see FIG. 9).

Example 6

Data Analysis

Patients are selected into one of three groups: healthy premenopausal (PRE); healthy postmenopausal (POST), and osteoporotic postmenopausal (OSTEO) women. All groups are studied by: (1) dental x-ray images of the periapical and canine region; (2) quantitative computed tomography of the spine and (3) hip; (4) dual x-ray absorptiometry of the spine and (5) hip; (6) single x-ray absorptiometry of the calcaneus, and (7) ultrasound of the calcaneus using standard techniques. A diagnosis of osteoporosis is made when at least one atraumatic vertebral fracture as determined by a semi-quantitative assessment of morphologic changes of the thoracic and lumbar spine on lateral conventional x-rays is observed.

The means and standard deviations of the different bone structure measurements (see above) and bone mineral density measurements (mandibular BMD, QCT spine, QCT hip, DXA spine, DXA hip, SXA calcaneus, ultrasound calcaneus) are calculated for each patient group. The Student's t-test (t-values and p-values) and percent decrement are used for comparing the different measurements for reflecting intergroup differences. Annual, age-related changes are expressed as percent changes relative to the predicted values at age 30 and as fractional standard deviation (SD) of PRE. Correlations with age along with p-values are also be reported. Odds ratios (for 1SD change in the measured parameter) and 95% confidence limits based on the age-adjusted logistic regression are calculated to measure the discriminative ability (for discriminating between the postmenopausal osteoporotic and the normal postmenopausal group) and the risk of osteoporotic fracture associated with the measured parameter. The pairwise comparisons of the discriminative abilities are tested using age-adjusted receiver operating characteristic (ROC) curve analysis.

Pairwise comparisons of all techniques are obtained by pooling all subjects (PRE, POST, OSTEO) and using Pearson's correlation coefficients (r), percent standard errors of the estimate (CV), and p-values for testing significance of correlations.

To compare measurements for their diagnostic ability, a kappa score analysis is performed on the normal postmenopausal women (POST) and the osteoporotic postmenopausal women (OSTEO). This is done by classifying every woman from the postmenopausal groups as osteopenic if her T-score with respect to the reference group (PRE) is less (or in case of structural parameters also greater) than 2.5. The T-score for an individual woman and a particular measurement is defined as the measurement minus the mean measurement of young normals (PRE) divided by the SD of the measurement in the PRE group. Note that the T-score is measuring the position of an individual woman with respect to the PRE group and is different from the Student's t-value.

Example 7

Longitudinal Monitoring of Bone Structure

Algorithms and software to match follow-up dental x-rays obtained at a time point $T_2$ relative to baseline x-rays of the mandible obtained at an earlier time point $T_1$ are developed. For purposes of monitoring of therapeutic response, bone structure parameters have to be measured at the same location of the mandible at different points in time. Thus, in order to compensate for differences in patient positioning and in order to find corresponding regions of interest (ROI's) for comparison of the results between baseline and follow-up examinations, it is desirable to register two dental x-ray images.

Due to possible slight differences in the projection angle of the x-ray beam on the film in the two images to be registered, an elastic matching step is preferably included. The first step, however, is a global affine transformation, for which the mutual information is used as a cost function. Wells et al. (1996) Medical Image Analysis 1:35-51. The mutual information $I_{M,N}$ of two images M and N is defined as $$I_{M,N} = \sum_{(m,n)} p_{MN}(m,n) \log\left(\frac{p_{MN}(m,n)}{p_M(m) p_N(n)}\right).$$

Here, the gray values occurring in the two images are regarded as random variables, and the mutual information provides a measure of the strength of the dependence between these variables. $p_M$ and $p_N$ are the distributions of M and N respectively, and $p_{MN}$ is the joint distribution of M and N. Maintz et al. (1998) SPIE Medical Imaging—Image Processing. These distributions can be approximated from the marginal and joint gray value histograms, more accurately with the use of a Parzen window function. Powell's method can be used as an optimization scheme to find the best affine transformation for N to match it with M. Press et al. ("Numerical Recipes in C." 2nd edition, 1992, Cambridge University Press.

This global transformation is followed by local elastic adjustments to improve the match. To achieve this, the conditional probability densities p(n|m) are estimated from the joint histogram of the globally registered images. The transformation vector field t(x) is then determined such that N(x−t(x)) is as similar to M(x) as possible by maximizing the local gray value correspondence, which for a fixed value of x is defined as $$c_x(t) = \int w(x'-x) p(N(x'-t)|M(x')) dx'.$$

Here, w is a window function whose width determines the size of the region that is used to compute t(x). To determine the window function, an approach similar to the one described in Warfield et al. "Brain Warping" 1999, Academic Press, p: 67-84 is used. A number of successively wider window functions $w_i$ are combined into a single window $$w = \sum_i W_i w_i,$$

where the weights $W_i$ are given as $$W_i = \frac{1}{\sum_i \det(Q_i)} \det(Q_i) \text{ with } Q_i = \int w_i(x'-x) \nabla N(x') \nabla N^T(x') dx'.$$

The exact location of the ROI after automatic placement in the baseline image for a particular patient is kept in a database. When the patient returns for a follow-up exam, the new image is registered with the baseline image, and thus transformed into the coordinate system of the baseline image. The bone structure in the registered follow-up x-ray can then be measured at exactly the same position as in the baseline image.

Example 8

Influence of Positioning of the Femur on Bone Structural Measurements

The effect(s) of the positioning of the femur on each parameter of the bone structure assessments is (are) examined. Hip x-rays are obtained in normal postmenopausal women and postmenopausal women with osteoporosis in neutral position and in various degrees of internal and external rotation.

The diagnosis of osteoporosis is made when at least one atraumatic vertebral fracture as determined by a semi-quantitative assessment of morphologic changes of the thoracic and lumbar spine on lateral conventional radiographs is observed. See, also, Genant et al. (1993) J. Bone Miner Res. 8:1137-1148.

Standard anteroposterior hip radiographs are obtained with the extremity at 30° internal rotation, 15° internal rotation, 0°, 15° external rotation, and 30° external rotation. These angles are achieved by placing the foot and ankle against a 30° or a 15° degree wedge in either internal or external rotation of the femur. The foot is secured against the wedge using Velcro straps.

The effect of positioning is assessed by calculating the pair wise coefficient of variation (CV %) between the results for the 0° position and the other positions for each individual subjects. The angular dependency will be expressed for each of the angles 30° internal rotation, 15° internal rotation, 15° external rotation, and 30° external rotation as the root-mean-square of these CV % values over all subjects. In general, parameters with the least dependency on angular positioning of the femur are selected.

If the pair wise coefficient of variation between the results for the 0° neutral position and the 15° internal or external rotation position exceed 10% for the majority of the structural parameters measured, a foot holder that fixes the patients' foot in neutral position can be used The foot holder is designed with a base plate extending from the mid to distal thigh to the heel. The base plate preferably sits on the x-ray table. The patients' foot is positioned so that the posterior aspect of the heel is located on top of the base plate. The medial aspect of the foot is placed against a medial guide connected rigidly to the base plate at a 90° angle. A second, lateral guide attached to the base plate at a 90° angle with a sliding mechanism will then be moved toward the lateral aspect of the foot and will be locked in position as soon as it touches the lateral aspect of the foot. The foot will be secured to the medial and lateral guide using Velcro straps. It is expected that the degree of involuntary internal or external rotation can be limited to less than 5° using this approach.

Example 9

Influence of X-Ray Tube Angulation on Bone Structural Measurements

The effect(s) of the positioning of the x-ray tube on each parameter of the bone structure assessments is (are) examined. Dental x-rays are obtained in normal postmenopausal women and postmenopausal women with osteoporosis. The diagnosis of osteoporosis is made when at least one atraumatic vertebral fracture as determined by a semi-quantitative assessment of morphologic changes of the thoracic and lumbar spine on lateral conventional radiographs is observed. See, also, Genant et al. (1993) J. Bone Miner Res. 8:1137-1148.

Standard anteroposterior dental radiographs are obtained in the incisor region of the mandible. The x-ray tube is aligned with an angle of 0°, 10°, 20°, 30°, and −10°, −20°, and −30° relative to the dental x-ray film. These angles are achieved with use of a goniometer applied to the metal tube located in front of the dental x-ray tube. The dental x-ray film is positioned at the posterior mandibular wall in the incisor region.

The effect of positioning is assessed by calculating the pair wise coefficient of variation (CV %) between the results for the 0° position and the other tube positions for each individual subject. The angular dependency will be expressed for each of the angles as the root-mean-square of these CV % values over all subjects.

The results indicate that a 10 degree tube angulation can result in a 12% error in apparent density.

A mechanical alignment system is then applied to the Rinn holder. For this purpose, an extension tubing is attached to the Rinn holder. The extension tubing is designed so that its inner diameter is slightly greater (and fits over) than the outer diameter of the dental x-ray system metal tube (FIG. 15). The dental x-ray system metal tube is then inserted into the extension tubing attached to the Rinn holder that reduces alignment error of the x-ray tube relative to the x-ray film. One group of patients then undergo two x-rays each of the incisor region. The results indicate that the short-term in-vivo reproducibility error of dental bone density and bone structure measurements is reduced with use of the mechanical alignment system by reducing x-ray tube angulation relative to the dental film and the anatomic landmarks in the mandible.

Example 10

Measurement of Bone Density, Bone Structure, Macro-Anatomical Parameters and Biomechanical Parameters and Selecting Therapy An x-ray image of a mandible or a hip or spine or other bone is analyzed using a computer program capable of assessing bone density, bone structure, macro-anatomical parameters, or biomechanical parameters, for example as described above. The computer program derives a measurement of one or more bone density, bone structure, macro-anatomical or biomechanical parameters of the trabecular bone. The measurement of the parameter(s) is compared against a database containing information on said one or more parameters in normal, healthy age-, sex-, and race matched controls. If the patient's measurement differs by more than 2 standard deviations from the age-, sex-, and race matched mean of normal, healthy subjects, a report is sent to the physician who then selects a therapy based on the measurement(s).

Example 11

Measurement of Bone Density, Bone Structure, Macro-Anatomical Parameters and Biomechanical Parameters and Monitoring Therapy One or more x-ray images (mandible, hip or spine or other bone) are obtained from a patient undergoing therapy for osteoporosis, for example using an anabolic or an antiresorptive drug at two different time points T1 and T2. The x-rays are analyzed using a computer program capable of assessing bone density, bone structure, macro-anatomical parameters, or biomechanical parameters. The computer program derives a measurement of one or more parameters of the bone for both time points T1 and T2. The measurement of the bone density, bone structure, macro-anatomical, or biomechanical parameter(s) at T1 and T2 is compared against a database containing information on said one or more parameters in normal, healthy age-, sex-, and race matched controls for each time point. If the results indicate that the patient has lost 5% or more bone between time points T1 and T2 despite therapy, a physician selects a different, more aggressive therapy.

Example 12

Measurement of Macro-Anatomical and/or Biomechanical Parameters

A hip radiograph is obtained using standard techniques and including a calibration phantom as described herein. The reference orientation of hip x-rays is the average orientation of the femoral shaft.

A. Edge-Detection

A global gray level thresholding is performed using a bi-modal histogram segmentation algorithm on the hip x-ray generates a binary image proximal femur.

Edge-detection of the hip x-ray can be used. Optionally, edge-detection methods are further refined by obtaining breaking edges detected into small segments and characterizing the orientation of each segment, thereby obtaining the outline of proximal femur. Each edge segment is then referenced to a map of expected proximal femur edge orientation and to a map of probability of edge location. Edge segments that do not conform to the expected orientation or are in low probability regions are removed. Morphology operations are applied onto the edge image to connect edge discontinuities. The edge image forms an enclosed boundary of the proximal femur. The region within the boundary is then combined with the binary image from global thresholding to form the final mask of the proximal femur.

Within a selected region of interest, edge detection is applied. Morphology operations are applied to connect edge discontinuities. Segments are formed within enclosed edges. The area and major axis length of each segments are then measured. The regions are also superimposed on the original gray level image and the average gray level within each region is measured. The cortex is identified as the segments that are connected to the boundary of the proximal femur mask, that has the greatest area, longest major axis length and has a mean gray level above the average gray level of all enclosed segments within the proximal femur mask. The segment identified as cortex is then skeletonized. The orientation of the cortex skeleton is verified to conform to the orientation map of proximal femur edge. Euclidian distance transform is applied to the binary image of the segment. The values of distance transform value along the skeleton are sampled and statistics (average, standard deviation, minimum, maximum and mod) measured.

As will be appreciated by those of skill in the art, measurements of macro-anatomical parameters described here can be applied to hip, spine or knee radiographs with modifications to adapt to the shape, scale and location of macro-anatomical features specific to the anatomical region.

The invention claimed is:

1. A method to derive information regarding one or more bone parameters from an image comprising:
   (a) obtaining image data of bone from a subject;
   (b) defining a region of interest from the image data;
   (c) defining within the region of interest at least first and second windows, wherein the first and second windows overlap;
   (d) analyzing information in the first window to determine at least a first value for a parameter, the parameter selected from the group consisting of bone microarchitecture, bone macroanatomy, biomechanical parameters and combinations thereof;
   (e) analyzing information in the second window to determine at least a second value for the parameter; and
   (f) generating a set of data at least in part from the first and second values.

2. The method of claim 1, wherein the information in the first window is further analyzed to determine a third value of a second parameter; wherein the information in the second window is further analyzed to determine a fourth value of the second parameter, and wherein the set of data is generated based at least in part on the first, second, third and fourth values.

3. The method of claim 1, further comprising generating a field of sampling points of the image, the sampling points being distributed at regular intervals in the image, and the first window being located at a first sampling point of the field of sampling points, and the second window being located at a second sampling point of the field of sampling points.

4. The method of claim 1, further comprising generating a field of sampling points of the image, the sampling points being distributed at irregular intervals in the image, and the first window being located at a first sampling point of the field of sampling points, and the second window being located at a second sampling point of the field of sampling points.

5. The method of claim 1, wherein the parameter is bone micro-architecture.

6. The method of claim 1, wherein the parameter is bone macro-anatomy.

7. The method of claim 1, wherein the image is two-dimensional.

8. The method of claim 7, wherein image is an x-ray image.

9. The method of claim 1, wherein the image is three-dimensional.

10. The method of claim 1, wherein the image is an electronic image.

11. The method of claim 1, wherein the subject is an osteoporosis subject.

12. The method of claim 1, further comprising creating a parameter map based at least in part on the values associated with the parameter.

13. The method of claim 12, further comprising:
   (a) generating multiple parameter maps;
   (b) generating a composite parameter map from the multiple parameters maps of step (a); and
   (c) analyzing the composite parameter map.

14. The method of claim 12, further comprising:
   analyzing the parameter map, wherein the analysis is watershed segmentation analysis or Markov random field analysis.

15. The method of claim 12, further comprising:
   (a) generating a finite element model from the parameter map; and
   (b) applying simulated force vectors to the finite element model.

16. The method of claim 13, further comprising:
   (a) predicting a fracture path using the composite parameter map; and
   (b) evaluating one or more selected bone parameters along the predicted fracture path.

17. The method of claim 14, further comprising:
   (a) predicting a fracture path using the analyzed parameter map; and
   (b) evaluating one or more selected bone parameters along the predicted fracture path.

18. The method of claim 1, further comprising
   diagnosing a bone disease based on the generated set of data and
   selecting and administering a suitable treatment to said subject based on said diagnosis.

* * * * *